US007311400B2

(12) United States Patent
Wakil et al.

(10) Patent No.: US 7,311,400 B2
(45) Date of Patent: Dec. 25, 2007

(54) DETERMINING CLINICAL REFRACTION OF EYE

(75) Inventors: Youssef Wakil, Houston, TX (US); Vasyl V. Molebny, Kiev (UA); Sergiy Molebny, Houston, TX (US); Ioannis Pallikaris, Crete (GR)

(73) Assignee: Tracey Technologies, LLC, Houston, TX (US)

( * ) Notice: Subject to any disclaimer, the term of this patent is extended or adjusted under 35 U.S.C. 154(b) by 827 days.

(21) Appl. No.: 10/475,153

(22) PCT Filed: Apr. 16, 2002

(86) PCT No.: PCT/US02/12141

§ 371 (c)(1),
(2), (4) Date: Oct. 15, 2003

(87) PCT Pub. No.: WO02/083078

PCT Pub. Date: Oct. 24, 2002

(65) Prior Publication Data

US 2005/0057723 A1    Mar. 17, 2005

Related U.S. Application Data

(60) Provisional application No. 60/284,364, filed on Apr. 16, 2001.

(51) Int. Cl.
*A61B 3/10* (2006.01)
(52) U.S. Cl. .................. 351/205; 351/222; 351/246
(58) Field of Classification Search ............. 351/205, 351/212, 222, 246, 247
See application file for complete search history.

(56) References Cited

U.S. PATENT DOCUMENTS 3,290,927 A    12/1966 Gambs .................... 73/80

(Continued)

FOREIGN PATENT DOCUMENTS

JP            63242219         10/1988

(Continued)

OTHER PUBLICATIONS

Wang Li et al, "Comparison of a ray0tracing refractometer, autorefractor, and computerized videokeratography in measuring pesudophakic eyes.", XP002377279; US National Library of Medicine, Bethesda, MD; Feb. 2002.

(Continued)

*Primary Examiner*—Huy Mai
(74) *Attorney, Agent, or Firm*—Benjamin Aaron Adler

(57) ABSTRACT

Eye refraction is measured to achieve desired quality via a selected vision characteristics. A characteristic of vision is selected to correlate to the desired quality of vision from a group of vision characteristics comprising acuity, Strehl ratio, contrast sensitivity, night vision, day vision, and depth of focus, dynamic refraction over a period of time during focus accommodation, and dynamic refraction over a period of time during pupil constriction and dilation. Wavefront aberration measurements are used to objectively measure the state of the eye refraction that defines the desired vision characteristic. The measured state of refraction is expressed with a mathematical function enabling correction of the pre-selected vision characteristic to achieve the desired quality of vision. The mathematical expression function may be a Zernike polynomial having both second order and higher order terms or a function determined by spline mathematical calculations. Pre-selected vision characteristics may be determined using ray tracing technology.

32 Claims, 55 Drawing Sheets

U.S. PATENT DOCUMENTS

| | | | |
|---|---|---|---|
| 4,190,332 A | 2/1980 | Body et al. | 351/211 |
| 4,465,348 A | 8/1984 | Lang et al. | 351/211 |
| 4,691,716 A | 9/1987 | Tanne | 128/774 |
| 4,778,268 A | 10/1988 | Randle | 351/203 |
| 4,796,989 A | 1/1989 | Fukuma et al. | 351/212 |
| 5,148,205 A | 9/1992 | Guilino et al. | 351/159 |
| 5,258,791 A | 11/1993 | Penney et al. | 351/211 |
| 5,293,871 A | 3/1994 | Reinstein et al. | 128/660.06 |
| 5,414,478 A | 5/1995 | van Gelderen | 351/212 |
| 5,418,714 A | 5/1995 | Sarver | 364/413.13 |
| 5,581,405 A | 12/1996 | Meyers et al. | 359/571 |
| 5,589,897 A | 12/1996 | Sinclair et al. | 351/223 |
| 5,722,427 A | 3/1998 | Wakil et al. | 128/898 |
| 5,841,511 A | 11/1998 | D'Souza et al. | 351/212 |
| 5,847,804 A | 12/1998 | Sarver et al. | 351/206 |
| 5,875,019 A | 2/1999 | Villani | 351/211 |
| 5,953,100 A | 9/1999 | Sarver et al. | 351/206 |
| 6,000,800 A | 12/1999 | Webb et al. | 351/211 |
| 6,004,313 A | 12/1999 | Shimmick et al. | 606/5 |
| 6,082,856 A | 7/2000 | Dunn et al. | 351/160 |
| 6,086,204 A * | 7/2000 | Magnante | 351/212 |
| 6,199,986 B1 | 3/2001 | Williams et al. | 351/221 |
| 6,234,631 B1 | 5/2001 | Sarver et al. | 351/212 |
| 6,382,795 B1 | 5/2002 | Lai | 351/212 |
| 6,382,797 B1 | 5/2002 | Bille et al. | 351/212 |
| 6,409,345 B1 | 6/2002 | Molebny et al. | 351/212 |
| 6,428,168 B2 * | 8/2002 | Sarver et al. | 351/212 |
| 2003/0011745 A1 | 1/2003 | Molebny et al. | |

FOREIGN PATENT DOCUMENTS

| | | |
|---|---|---|
| UA | 98105286 | 7/1998 |
| WO | PCT/US99/23327 | 7/1999 |

OTHER PUBLICATIONS

Salchow D J et al; "Comparison of objective and subjective3 refraction before and after laser in situ keratomileusis" XP002377278. US National Library of Medicine (NLM), Bethesda, MD Jun. 1999.

Corneal Topography The State of the Art by James P. Gills, Donald R. Sanders, Spencer P. Thornton, Robert G. Martin, Johnny L. Gayton, Jack T. Holladay—Chapter 5—The EyeSys 2000 Corneal Analysis System by Spencer P. Thornton, M.D. FACS and Joseph Wakil, M.D. Mee.

EyeSys 2000 Corneal Analysis System: The Ultimate in Corneal Topography from the Proven Leader (Brochure). Copyright EyeSys Technologies, Inc., 1995.

EyeSys Vista: Hand-Held Corneal Topographer (Brochure).

Ophthalmic Terminology: Speller and Vocabulary Builder—Third Edition—by Stein, Slatt, and Stein.

Contact Lenses: Update 1—Chapter 4—Corneal Topgraphy by J. James Rowsey and David J. Schanzlin (Copyright 1986 by Little, Brouwn and Company).

Contact Lenses—Chapter 17—Measurement of Corneal Curvature: Keratometer (Ophthalmometer) by Oliver H. Dabezies, Jr. and Jack T. Holladay (Copyright 1984 by Little, Brown and Company.

A Comprehensive Guide to Fitting Contact Lenses with EyeSys Pro-Fit Contact Lens Fitting Software by Beth A. Soper, C.O.A. (EyeSys System 2000—Version 3.1).

M.S. Smirnov. Measurement and wave aberration of the eye. Biofizika (Biophysics USSR), 6, pp. 687 through 703 (previously pp. 776-794, 1961). English translation of: p. 690 translation of the last paragraph continuing onto p. 691, and on page 691 $1^{st}$, $2^{nd}$ and $3^{rd}$ full paragraphs.

Van de Brink. Measurement of the geometrical aberrations of the eye. Vision Res. 2, pp. 233-244, 1962.

N.M. Sergienko. Oftalmologicheskaya optika (Ophtalmic Optics). Moscow, Meditsina, 1991, 142 pages. English translation of: p. 30-32 text of the last paragraph referring to Figure 19 continuing onto pp. 31 and 32, and first full paragraph of p. 32.

R.H. Webb, C.M. Penney, and K.D. Thompson. Measurement of ocular local wavefront distortion with a spatially resolved refractometer. Applied Optics. 31, pp. 3678-3686, 1992.

S.G. El Hage and Bemi F. Contribution of the crystalline lens to the spherical aberration of the eye. J. Opt. Soc. Am. 63, pp. 205-211, 1973.

J. Liang, B. Grimm, S. Goelz, and J. F. Bille, Objective measurement of wave aberrations of the human eye with the use of a Hartmann-Shack wave-front sensor. J Opt. Soc. A. A 11, pp. 1949-1957, 1994.

J. Liang and D.R. Williams. Aberrations and retinal image quality of the normal human eye. J Opt. Soc. Am. A 14, pp. 2873-2883, 1997.

J. Liang, D.R. Williams and D.T. Miller. Supernormal vision and high resolution retinal imaging through adaptive optics, J. Opt. Soc. Am., A 14, pp. 2884-2892, 1997.

T. Seiler, P.J. McDonnell, "Excimer laser photorefractive keratectomy", Surv. of Ophthalm., 40, pp. 89-118, 1995.

Eye Sys Technologies brochure, EyeSys Software The power that drives high performance corneal topography. EyeSys Technologies Inc., 1995.

W.D. West, OD. Corneal Topography: It's not just for surgeons anymore. Eyecare Technology, Jul./Aug. 1995.

* cited by examiner

Refraction Sphere

Cylinder Sphere

- CIRCLE OF DEPTH OF FOCUS
- CIRCLE OF LEAST CONFUSION (DIAMETER, d)
- CIRCLES OF DEPTH OF FOCUS (DIAMETER, d) EQUAL TO X% x d = D
- DEPTH OF FOCUS
- CONOID OF STURM

Refractive Error

Spherocylindrical Correction

Custom Correction

DETERMINING CLINICAL REFRACTION OF EYE

RELATED APPLICATION

The present invention relates to prior co-owned pending provisional application Ser. No. 60/284,364 filed 16 Apr. 2001 and incorporated by reference herein for all legitimate purposes as if fully set forth.

TECHNICAL FIELD OF THE INVENTION

The invention relates to methods of determining the clinical refraction of the human eye, and in particular to the use of algorithmic methods to objectively measure refractive characteristics of the eye and then to determine using one or more algorithms the clinical correction whether in terms of sphere, cylinder and axis or otherwise to favorably correlate the correction to manifest refraction as would be determined according to subjective clinical determination and preserve or improve the quality of vision.

BACKGROUND OF THE INVENTION

Some have used Zernike polynomials to calculate wavefront measurements of refraction aberrations of an eye and have used second order terms of the Zernike polynomial expansion for defining the aberration wavefront from which the refractive be used to derive spherical correction and orthogonal and oblique astigmatism terms can be used to derive cylinder and axis correction. Subjective eye examinations typically use a device such as a phoropter to provide a patient with choices among proposed sphero-cylindrical corrections. Different lenses with stepwise varied magnification spherical magnification and cylindrical magnification are alternately placed in the field of vision and the patient is asked to subjectively select which one provides the best vision. The cylindrical lenses are rotated to determine the angular orientation of the astigmatism. Corrective prescriptions are typically provided in terms of spherical correction (+/−diopter) and cylindrical correction (+/−diopter at an angle) for providing vision corrections such as external spectacle lenses, contact lenses, implanted lenses, corneal ablation with Eximer laser surgery (laser vision correction).

Objective measurements of refraction of the eye have been accomplished using various technologies. Modern objective measurement technology makes measurements from which wavefront aberrations are determined and expressed in terms of mathematical functions useful for approximating the shape or slope of the wavefront contrasted to a wave front that would be produced by an eye with theoretically perfect refraction. Curve fitting using Zernike polynomial expansion has become one standard for mathematically expressing an approximation for the refraction aberration wavefront. From the approximation thus determined, correction to the vision is mostly produced according to sphero-cylindrical corrections. Or as is recently possible with custom laser vision correction.

SUMMARY OF THE INVENTION

It has been discovered that defining the clinical refraction or the correction of an eye using Zernike Polynomial calculation of the wavefront produces inaccuracies in certain real eye situations. While simple cases of wavefront aberrations may be addressed by other techniques, there are significant drawbacks in more complicated cases. The present invention provides a method for diagnosing the refractive state of the eye using objective measurement of refractive characteristics of an eye and correlating such objectively measured characteristics to subjectively desired quality of vision. For example, a particular objectively diagnosed state of the eye may correlate to a subjectively desired quality of vision that could be obtained by using sphero-cylindrical optical corrections to target an objectively measured characteristic. Before producing a corrective solution the sufficiency of aberration data is examined using a set of criteria that may be selected from both known criteria as well as newly proposed criteria such as a cross-section of least confusion (sometimes referred to as the "circle of least confusion" because the cross-section will be a circle for well formed eyes and sometimes referred to as "C.O.L.C."). The criteria selected is used to determine the "best possible" corrective refraction for obtaining the desire quality of vision. The quality of vision is the cumulative result of the total refraction of the eye under many different real life conditions. The desired quality of vision may be different for different primary needs of individual patients. Other objectively measured characteristics of refraction can also be correlated to subjectively desired characteristics or quality of vision and are found to be useful as measurement criteria for determining correction appropriate for obtaining the desired quality of vision. For example these characteristics or criteria include, acuity, Strehl ratio, contrast sensitivity, night vision, day vision, and depth of focus. Dynamic refractometry or refraction measured repeatedly or continuously over a period of time, including near to far and far to near accommodation over time, pupil constriction and dilation over time, and selected combinations of these characteristics, also provides characteristics useful to assess quality of vision. A test phase plate may be produced and examined with the patient's eye to confirm the patient's better vision or the patient's subjectively desired quality of vision and if needed refine the correction prior to implementing the correction for the patient that might be difficult to reverse, such as implants, ablation and laser surgery.

BRIEF DESCRIPTION OF THE DRAWINGS

The foregoing objects, advantages, and features, as well as other objects and advantages, will become more apparent with reference to the description, claims and drawings below, in which like numerals represent like elements and in which:

DETAILED DESCRIPTION OF THE PREFERRED EMBODIMENTS

Figure 1:
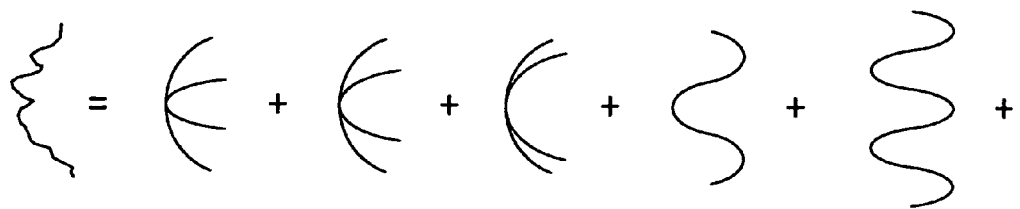
FIG. 1 is a schematic representation of a wavefront "equated" to the sum of components of best fit curves as determined using Zernike polynomial expansion.

It has been discovered that defining the clinical refraction or the correction of an eye using Zernike Polynomial calculation of the wavefront can produce inaccuracies in certain real eye situations. The use of Zernike Polynomials as a mathematical language for defining refractive characteristics may continue to be useful. (See FIG. 4) Wavefront measurement expressed in terms of low order Zernike polynomials may be used in simple cases to produce acceptable analysis in correlating with the quality of vision for that patient. One aspect of the invention is to improve the accuracy and usefulness of Zernike Polynomial calculations by using selected higher order expansion terms that are not currently used in typical wavefront aberration determinations. (See FIG. 5.) For example in complicated cases where a wavefront aberration is expressed in terms of a Zernike polynomial using only second order terms (i.e., lower order) when used to direct correction, does not produce the desired quality of vision. (See FIGS. 6 and 7.) It has been found that selected higher order Zernike polynomial terms can be applied to improve the analysis to direct the desired correction to facilitate obtaining the patient quality of vision desired. (See FIGS. 5 and 8.) Where the eye is significantly distorted as with significant point to point variations in the aberrations, other more adequate mathematics such as using splines mathematics or other ways of interpolation are more suitably applied.

Another aspect of the present invention is to provide a method for objective measurement of refractive characteristics of an eye to predict corrective actions, to change the objectively measured refractive characteristics of the eye to obtain desired quality of vision by the patient. An aspect of the method is to use statistically valid testing and correlation between objective eye refraction or eye aberration testing results and subjective eye testing results for the same sample of patients to predict corrective measures to obtain subjectively desired quality of vision based upon objective testing. For example, objective measurements of the refractive state of the eye may be used to predict appropriate spherocylindrical optics to correct the refraction errors of the eye to obtain a quality of vision determined by minimizing the cross-section of least confusion or circle of least confusion as determined by ray tracing analysis. This analysis is evidenced by retinal spot diagrams which sow where each light beam directed into the eye is focused onto the retina represented bt a grid where the center represents the "deal" focal point conjugate to the patient's fovea when fixating on a visual target. A significant characteristic of the refraction corrections to provide a desired quality of vision might can also include measurements of the Strehl ratio or other measured criteria that indicate the patient's contrast sensitivity and to direct corrective efforts to produce a high Strehl ratio or a newly determined ratio of light concentration per unit area as an indication of a desired quality of good contrast sensitivity for the patient. For example, this can be presented as a contrast sensitivity index ranging from 0.0 to 1.0 (or 0% to 100%) where 0.0 is low contrast and 1.0 is high contrast. Other examples of objective criteria for determining desired visual quality might include improved depth of focus, improved night vision, improved binocular vision, improved dynamic refraction, such as refraction over time during near-to-far and far to near focus accommodation, improved vision during dark to light and light to dark dynamic pupil contraction and dilation adjustment over time, and combinations of the foregoing criteria.

According to one aspect of the invention, wavefront aberration is measured and expressed in terms of a Zernike polynomial of low order (second order) defocus and astigmatism. A test plate is produced according to the Zernike expression and is applied to test the effectiveness of the aberration data for producing a desired quality of vision. If the results are good with the test plate as in a simple case of a nearly normal eye then vision correction may be made, whether laser surgery, implants, external corrective lenses, or otherwise, based upon the measured aberrations as expressed with the Zernike polynomial. If the test plate is produced and applied to the patient's eye without obtaining good results as in a more complicated case, such as an eye experiencing post operative problems, the aberration data may be used to calculate an expression of the wavefront in terms of a higher order Zernike polynomial, or in terms of another mathematical expression, appropriate for the severity of the aberrations to produce a test plate applied to the patient's eye to obtain the desired quality of vision. Again if the test plate provides a desired quality of vision, then vision correction may be made, whether with laser surgery, implants, external corrective lenses, or otherwise, based upon the measured aberrations as expressed with the higher order Zernike polynomial terms or other mathematical expression such as Taylor series polynomial expansion, splines mathematical interpolation or otherways of interpolation. According to yet another aspect of the invention, before a test plate is produced, the effectiveness and sufficiency of the aberration data are examined using a set of criteria (the previously known criteria and newly proposed criteria such as cross-section of least confusion, Strehl ratio, contrast sensitivity, depth of focus, dynamic focus accommodation, refraction during dynamic pupil contraction and dilation, binocular refraction, and etc.) test plates are thus produced with greater success in providing the desired quality of vision and proven correction to the vision of the eye is made with greater accuracy and at a lower cost.

Reference is made to FIG. 1 that is a rudimentary schematic representation of a summing of curve components defined by polynomial expansion terms to approximate the total wavefront aberrations of a measured refraction of an eye. Interpreting the data of the wavefront aberrometry and search for their correspondence to the global refraction parameters are of significance for clinical use.

Figure 2:
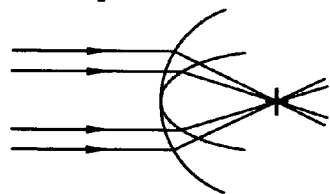
FIG. 2 is a schematic diagram of determination of an idealized eye refraction sphere and cylinder measurement assuming point focus on the retina.

Reference is also made to FIG. 2 which is a schematic depiction of the expansion of Zernike polynomial terms. It is observed that the terms piston and tilt merely define tilt of the of the wavefront aberration of the eye, and the second order terms (lower order terms) of defocus corresponds to a spherical component and the two astigmatism terms correspond to cylindrical components at orthogonal and oblique angles. These are nominally the terms provided when vision is tested using a phoropter and also corresponding to the present standard for prescriptions for corrective lenses.

Along with the increasingly accurate spatially resolved measurement of aberration using ray tracing technology, software has been developed enabling the investigation of the influence of the first 28 Zernike polynomials on the quality of vision and on the global refraction parameters, being point spread function, spherical and cylindrical components of refraction. The result has been defining the equivalent refraction power of the eye as inversely proportional to the equivalent focus length, their dependence was investigated on the content of higher-order Zernike coefficient. Position of the focus was determined as a point on the optical axis of the eye, nearest to the energy center of the smallest beam cross-section. It has been found that the aberrations like coma, trefoil, pentafoil, and etc. do not influence the focus location, because at averaging, they result in equal positive and negative sums. Position of the focus is defined mainly by the coefficient Z3, Z4, and Z5. Higher-order spherical (Z12 and Z24) and cylindrical (Z11, Z13, Z23, and Z25) modes influence mainly the size of point spread function and dispersion along the optical axis, being not determinative for position of the focus in real eyes, in which the ratio of higher-to-lower modes was up to 0.01-0.2.

Corrected formulas according to the present invention provide global refraction parameters taking into account higher-order aberrations that do not change essentially the principal concepts.

Figure 5:
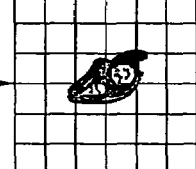
FIG. 5 is a schematic depiction of the use of second order and higher order Zernike polynomial terms to define aberrations from which correction is determined for optimizing the Point Spread Function("PSF") of an eye.
Figure 5:
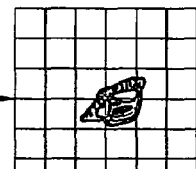
Figure 5:
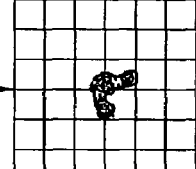
Figure 5:
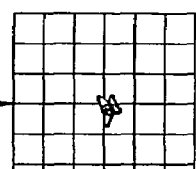

Zernike polynomials take a calculate/estimate wavefront measurement of the eye and break it down into its distinct discrete polynomial shapes under a "best-fit" algorithm. Sphere (defocus) and cylinder (astigmatism) are typically used to produce sphere and cylindrical corrective lenses, corrective implants, corrective laser surgery or other corrective actions and those are just two of the 28 terms of the Zernike polynomial expansion up to sixth order. With reference to FIG. 5, It has been found that the point spread function might be optimized by the use also of other higher order terms that also may comprise spherical and cylindrical components of refractive aberrations of the eye.

Figure 3:
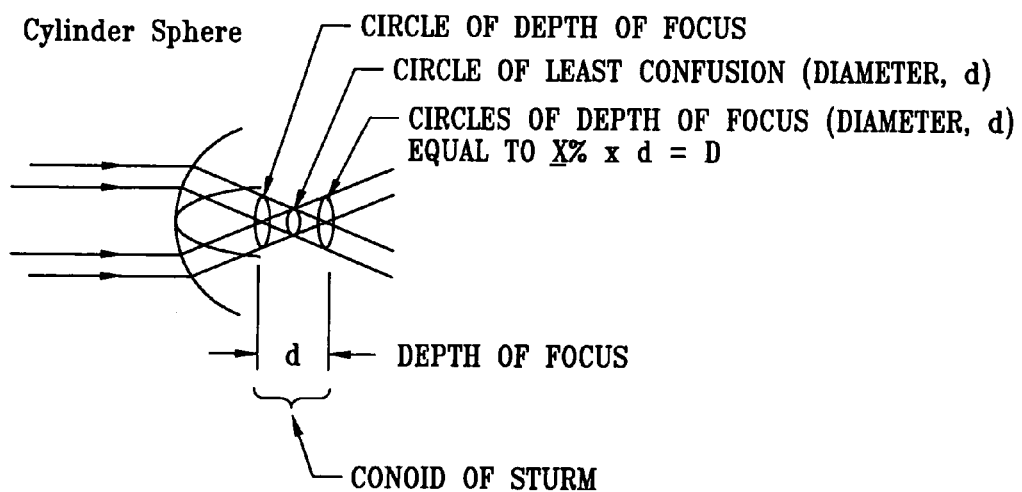
FIG. 3 is a schematic diagram of ray tracing determination of sphere-cylindrical optics to correct the refraction errors of the eye by targeting a "circle of least confusion" or the smallest beam cross-sectional area as the determinant of the best possible refraction (having discovered that the assumption of a focus point on the retina is often erroneous as a determinant of the subjectively desired quality of vision) and also showing a conoid of Sturm useful for identifying depth of focus.
Figure 4:
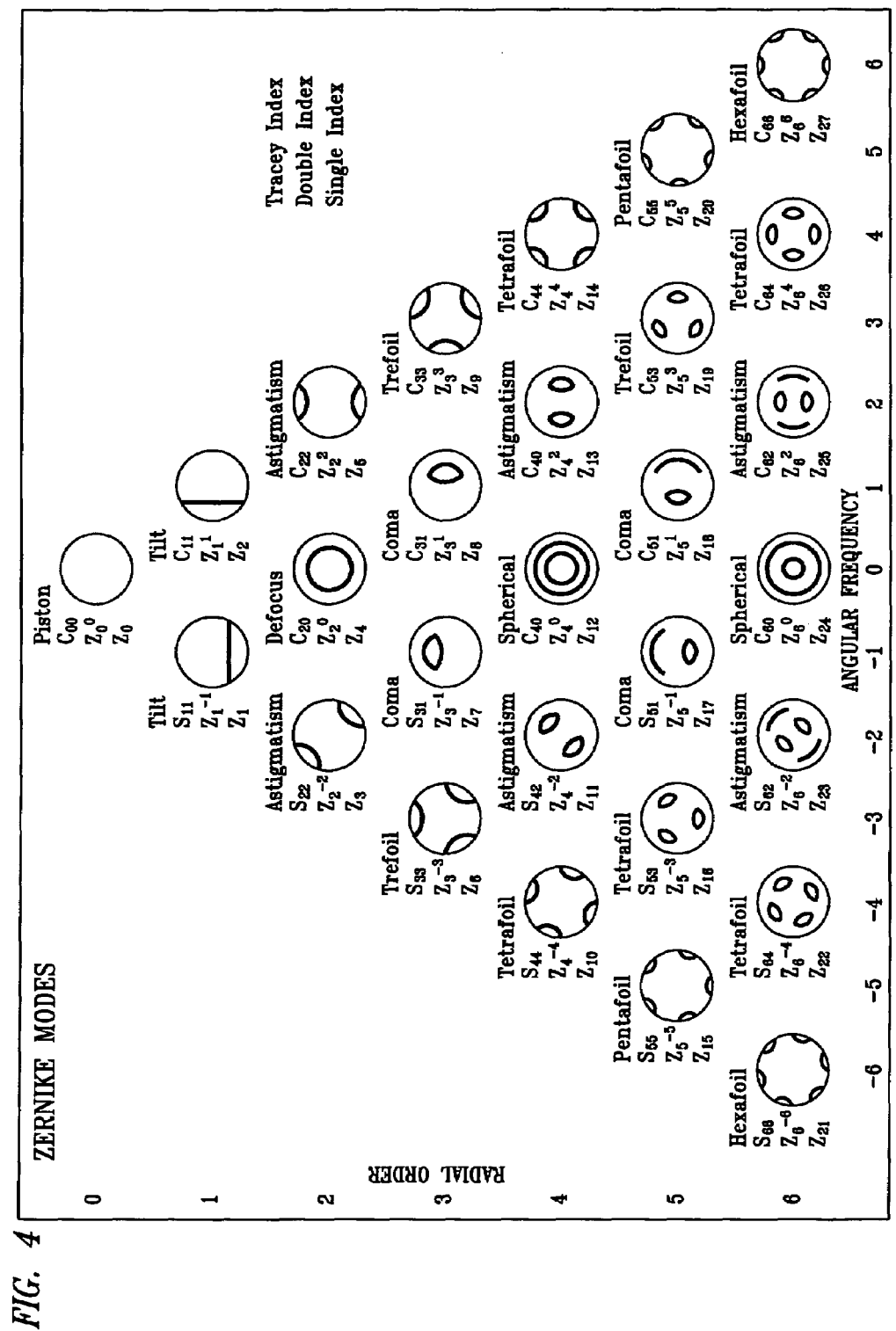
FIG. 4 is a schematic depiction of a Zernike Polynomial expansion including 28 terms obtained through the sixth order of the expansion.

Reference is made to FIGS. 3 and 4. The present invention provides refractive correction using objectively determined sphero-cylindrical optics to correct the refractive errors of the eye by targeting the circle of least confusion as the determinant of the best possible refraction. Thus, the algorithmic solution is to objectively measure refraction, and then beginning with the Zernike polynomial analysis to determine expression terms for sphere and cylinder. Next, based upon measurements made using a spatially resolved aberrometer disclosed more fully herein below and other measurements to ray trace the optics of the eye, to find the smallest beam cross-section (for a spherical eye this smallest beam area may be termed "the circle of least confusion") in three dimensional resolution. From the Zernike polynomial expression of the measured wavefront aberrations, corrections may be determined considering the circle of least confusion as the target criteria for obtaining the desired quality of vision by the patient being maximum acuity. The correction to the vision is calculated in an algorithmic, iterative form either using only sphero-cylindrical optical components to achieve the best-fit to the smallest circle of least confusion. The corrected results will be the ultimate objective refractive correction for the patient in spherocylindrical terms. This creates a new standard of care in auto-refraction technology. Those skilled in the art based upon the disclosure herein will understand that greater complexity of the expression of the aberrations may be required in highly distorted eyes so that higher order terms or other custom mathematical expressions of the wavefront aberrations may be obtained according to the present invention and from which expressions correction may be directed to achieve the desired quality of vision by the patient.

One aspect of the invention is to choose the spherocylindrical values in diopters to better match the manifest refraction or whatever other characteristic of vision desired. Deriving them just from the three coefficients by Zernike modes $Z_3$, $Z_4$, $Z_5$ using formulas that follow has been found to be inadequate for many purpose:

$$SphEq = -\frac{4C_4}{R^2}$$

$$Cyl = \frac{4}{R^2}\sqrt{C_3^2 + C_5^2}$$

$$Axis = \frac{1}{2}\arctan\frac{C_3}{C_5}$$

-continued
$$Sph = SphEq - \frac{1}{2}Cyl$$

where $C_1$—are coefficients in microns by non-normalised modes $Z_1$, R—is radius of scan in millimeters.

Calculation of sphero-cylindrical correction is based on the consideration that one wants to compensate for the total spherical and cylindrical errors through the entire scan area. According to one aspect of the invention it was discovered that not only $Z_4$, $Z_3$ and $Z_5$ contribute to these errors but also higher order terms $Z_{24}$, $Z_{11}$, $Z_{13}$, $Z_{23}$ and $Z_{25}$. A way to incorporate them into new formulas is as follows:

$$SphEq = -\frac{4(C_4 + C_{24})}{R^2}$$

$$Cyl = \frac{4}{R^2}\sqrt{(C_3 + C_{11} + C_{13})^2 + (C_5 + C_{13} + C_{25})^2}$$

$$Axis = \frac{1}{2}\arctan\left(\frac{C_3 + C_{11} + C_{23}}{C_5 + C_{13} + C_{25}}\right)$$

$$Sph = SphEq - \frac{1}{2}Cyl$$

According to another aspect of the invention, by using the sphero-cylindrical values, one can give either a) the minimal size to the spot on the retina created by the wide beam of light coming through the entire aperture of the pupil (point spread) or b) the maximal value to the Strehl ratio.

For this purpose software adds or subtracts some value of spherical error in diopters (for example 0.1 diopters, the drawing figures show 0.5 diopter increments or5 0.1 steps)to the terms used to calculate and display the retinal spot diagrams. User can stop this process whenever he/she thinks it's time to stop, that is, whenever he/she thinks that the maximal Strehl ratio or minimal point spread is achieved. These observations can be used to determine the contrast sensitivity r other characteristics of the quality of vision.

In FIG. 3 it will also be observed that the circle of least confusion generally corresponds to the a central body of a conoid of Sturm with apexes projecting toward the cornea and away from the cornea. The length of the conoid of Sturm from apex to apex is a measure of depth of focus because there is sufficiently high density of the beams or points of focus concentrated throughout a portion of thereof in either direction from the C.O.L.C. to provide adequate quality of vision. By testing of a statistically valid sample of patients the depth of vision for a desired quality of vision may be refined in terms of comparing the diameter of the COLC to the cross-sectional diameter of the spot diagram at the apexes of the conoid of Sturm or at a distance from the plane of the COLC to some other point within the conoid of Sturm that produces a depth of focus that is more representative of acceptable quality of vision to the sampling of patients.

It has also been found that using ray tracing technology advantages can be obtained in determining characteristics of refraction that are useful for determining quality of vision.

The ray tracing technology is used to take continuous measurements with rays or beams of light scanning the entire pupil within about 30 milliseconds. The refraction can therefore be tested dynamically over a period of time such as during dynamic eye accommodation of focus from near to far and from far to near. Such dynamic testing has been found to be useful for determining characteristics of vision during accommodation for focusing on objects near to far and far to near and also for insuring a more accurate determination at the maximum and minimum extreme conditions. By requiring the patient to concentrate on the "moving" target there is no inadvertent relaxation as sometimes occurs when the target is static. Also it has been found that the dynamic capabilities of the ray tracing technology allows dynamic testing of refraction over a period time for pupil constriction and dilation due to changed illumination conditions from scotopic (low light) conditions to mesotopic (medium light) conditions to photopic (bright light) conditions. It has been discovered that essentially all of the characteristics of quality of vision that are statically tested can also be tested dynamically tested using this concept.

With the advent of modem refractive surgery, it has become increasingly important to understand the physics of vision. The goal of "perfect vision" is an elusive one today. More often than not; perfect vision is obtained by chance and not calculation. New diagnostic instrumentation such as corneal topography have enabled today's refractive surgeons to more greatly appreciate the detail and variability of the cornea's shape and hence its refractive power. With the cornea providing roughly 70% of the refractive power of the eye it is a critical element, but not the entire picture. Fundamentally, refraction is the core of refractive surgery and the reason it is called refractive surgery in the first place. Refraction is the "Gold Standard" which is the ultimate measure of the clinical results. Simply put; a goal of refractive surgery is to successfully change the refractive status of our patients. Therefore, without an exact understanding of a patient's refraction optimum visual results will not be obtained.

The input alone of refractive correction desired is by itself one of the largest errors in the refractive correction procedure. It is certainly not an exact science, yet. As with corneal topography, the keratometer is obsolete by a device that makes no assumption of sphero-cylindrical optics and describes point-by-point detail of the cornea's surface both within and outside of the optical zone. With full appreciation of both optical and shape characteristics of the cornea, keratometric analysis is rudimentary and only a crude summary of corneal optical performance. The time has come to look at the entire refraction of the eye with the same level of objective measure and detail. With this greater detail in analyzing the refractive status of the eye to include higher order aberrations as opposed to only sphere and cylinder, it will be possible to better understand and measure the quality of vision problems in the refractive patient. Predictably, in viewing a refractive map of the entrance pupil that colors the refractive power of the entire eye on a point-by-point basis as opposed to the basic refractive numeric summary of sphere, cylinder and axis will have at least as much clinical impact as the corneal topography maps of the mid-1990's.

To measure refraction on a spatially-resolved basis requires the ability to look at the wavefront aberrations of the eye on a point-by-point basis within the pupil. The problem with the human eye is that it is not possible to just remove the patient's retina and place a CCD chip there to see how the eye is focusing the light passing through it. Instead, we must analyze light that is directed into the eye focused onto the retina creating a secondary light source. This secondary light source yields reflected light from the retinal surface which is projected out the exit pupil for analysis. There are three basic principles that apply to this measurement: aberroscopy, Hartmann-Shack wavefront sensing and ray tracing refractometry.

The aberroscope principles generally require an image of a rectilinear grid projected into the eye, which is focused as a distorted image of the grid onto the retina. This two-dimensional image on the retina contains distortions directly related to the non-homogenous optics of the eye and when this image is viewed through basically a direct ophthalmoscope (small aperture optics) a digital image is captured via a CCD camera which is then subject to a great amount of digital image processing to evaluate the distortions of the grid image on the retina and calculate the aberrations responsible for the pattern change. This technique is limited by the resolution of the aberroscope grid pattern in resolving points within the entrance pupil. Secondly, this technique acquires all its sample points in a single measurement requiring intensive data processing which is quite time consuming and leaving the system vulnerable to data confusion since highly aberrated eyes can cause distortions in the image which can easily create a cross-cross phenomena of the data points leaving the system unable to measure these problem eyes.

The Hartmann-Shack lenslet array is a device that measures the slope changes of the distorted wavefront as it exits the eye. This technology utilizes a beam of light entering the eye and reflecting from the retina as a secondary light source. As the reflected light travels retrograde through the eye it is subject to the eye's aberrations and projects out through the exit pupil striking a lenslet array, which is a grid of tiny lenses each of which focuses a small part of the wavefront onto a CCD imaging chip. The location of each of the lenslet's focusing point on the CCD is an indication of the slope of that specific part of the wavefront. The spatial resolution of this system is limited by the number of lenslets in the array and the sensitivity of this system is limited by the focal length of the lenses used in the lenslet array. There is a trade-off between the greater number of lenses desired and the greater light gathering power, or aperture, of each lens desired. The focal length of the lenslet array must also be selected and fixed. In other words, the design much like the aberroscope is limited to the selection of the lenslet array and once selected fixes the resolution and sensitivity of the unit. There is no programmable flexibility. Also, since the CCD imaging system must digitize the image of each lens in the array and then process its location before calculating the aberration there is a great deal of computation involved. The most significant problem with this design is its limited dynamic range. For example, these systems can typically measure higher order aberrations of only +/−2.0 D around a basic auto-refractor sphere and cylinder measurement. This device, like the aberroscope, is a single measurement at a time requiring significant computation, therefore susceptible to the same problem of data confusion with highly aberrated eyes and will fail to measure a significant fraction of the patient population, especially the problem patients post-operatively.

The ray-tracing refractometer as described more fully below with reference to FIGS. 4-15, uses the fundamental thin beam principle of optical ray tracing to measure the refractive power of the eye on a point-by-point basis. The simplicity of measuring one point in the entrance pupil at a time objectively is unique to this device. Both the aberroscope and Hartmann-Shack lenslet array systems measure the entire entrance pupil at once and all data points simultaneously making these systems easily susceptible to data points cross crossing with a highly aberrated eye, much like with Placido rings when they come together at points of extreme corneal topography changes. The ray-tracing refractometer system is designed to very rapidly fire a series of very small parallel light beams one at a time, within microseconds into the eye much like bullets out of an old-fashioned Gattling gun. These "bullets" of light pass through the entrance pupil of the eye in an infinite selection of software selectable patterns. Therefore, the ray-tracing refractometer system can actually probe particular areas of the aperture of the eye not only the entire aperture at once as the other technologies. Secondly, by design the ray-tracing refractometer system can register where each "bullet" of light strikes the retina as the fovea is represented by the conjugate focal point of the system from the patient's fixation. There are semiconductor photodetectors that are able to detect the location of where each ray of light strikes the retina and provide raw data actually measuring the (x,y) error distance from the ideal conjugate focus point. Hence, this raw data is a direct measure of the refractive error for that point in the entrance pupil and can very easily provide refractive correction needed with only simple computational processing. The speed of this system is tremendous. For example, 64 points within a 6 mm pupil can be measured in approximately 30 milliseconds. The ray-tracing refractometer can easily measure a large dynamic range of aberrations and maintain high-resolution detail of each sampled point. This should provide for a significant advantage when measuring a physiologic system, such as the eye, which can easily have a tremendous range of refractive errors. Additionally, since each point is sequentially measured there is never any confusion of which entrance pupil location registers with the retinal spot detected. As the ray-tracing refractometer system is practically a direct measure of the point spread function of the eye with its retinal spot detection, it can then easily provide for full calculation of wavefront deformation and modulation transfer function of the eye including the creation of a custom ablation map for the cornea.

In summary, all three of the above technologies can provide measurement of the aberrations of the eye on a spatially resolved basis, but the broader dynamic range, strong accuracy and reproducibility and added flexibility through simple software selection of desired data points for measurement sets the ray-tracing refractometer technology apart from both aberroscopy and Hartmann-Shack lenslet array.

FIG. 4 shows a schematic functional view of a ray-tracing refractometer device and method for synchronous mapping of the total refraction non-homogeneity and components thereof according to one aspect of the present invention. A polarized light source 120 and preferably a laser light source directs a polarized light beam 122 along a polarized light beam path nominally coincident with a central eye axis. The light beam is provided to a beam shifter 124 that is controlled to rapidly shift light beam 122 to any of a plurality of spatially offset parallel light beam paths 126. The mechanism for light beam shifting will be discussed more fully below in connection with FIGS. 6 and 7. Beam shifter 124 provides a polarized probing beam 126. It will be understood that a plurality of such probing beams can be produced by beam shifter 124 within a few milliseconds as, for example, 65 spatially offset parallel polarized probing beams can be produced within 12 milliseconds. For example, only one of the probing beams may be coincident with central axis 121, another of the plurality of offset polarized probing is depicted as 127. It will be understood that, for purposes of clarity, the 65 or more parallel polarized probing beams are not depicted in FIG. 4. Each of the probing beams 126, as well as the plurality of beams 127, pass through a beam splitter 128 to the eye 130 under investigation. Each probing beam 126, 127 impinges upon the cornea 131 at a plurality of impingement points as, for example, point 132 corresponding to probing beam 126 and impingement point 133 corresponding to probing beam 127, is representative of a plurality of impingement points.

The total refractive eye aberration for a thin beam of light entering at impingement point 132 is determined by locating point 136 on the retina and determining the spatial position 138 of that illuminated point on the retina 136 relative to the fovea 134 aligned along central axis 121. This position may be indicated relative to central axis 121 by coordinates ($dx_1$, $dy_1$). Light impacting the retina is backscattered off the retina. The backscattering is not a reflection per se and therefore the entering beam 126b is depolarized by the retinal surface. The backscattered light, having its optical axis represented by path 126c, is non-polarized light. The light 126c is directed in beam splitter 128 along path 126d to a polarizing beam splitter 140. Beam splitter 140 is a polarizing beam splitter so that it reflects non-polarized light and allows polarized light to pass through it. Thus, beam 126d is directed along path 126e through a lens 142 that focuses it along path 126f to a first photo detector 144. As will be discussed more fully below with respect to FIGS. 5, 6 and 11 photo detector 144 may be provided with a further beam splitter 94 and x and y photo detection arrays 88 and 89 to determine the position ($dx_1$ and $dy_1$). From this position and based upon the standard length of the eye, the total refraction characteristics can be calculated in a total refraction calculator 146. The total refraction calculator 146 may, for example, be circuitry and/or computer software within a multifunction computer 148.

Returning now to FIG. 4 each of the plurality of offset probing beams of which 127a is a sample, passes through beam splitter 128 and impinges upon the anterior surface of the cornea 131 at a plurality of impingement points of which 133 is a representative sample. Entering at impingement point 133, the beam 127b is projected due to the total refractive characteristics of the eye along the path of beam 127 to a point 150 on the retina 135 of eye 130. The backscattered light 127c from the retina 135 is projected back out through the eye aperture and is directed by beam splitter 128 along path 127d to the polarizing beam splitter 140, where it is directed along path 127e through lens 142 and onto a first photodetector 144 for determining the offset location 152 represented by ($dx_2$, $dy_2$) away from central axis 121. Through the rapid and repeated operation of beam shifter 124, a plurality of times within a fraction of a second, an entire grid pattern of impingement points, see, for example, the grid pattern of FIG. 13 As will be more fully discussed below, mappable data, with respect to the total eye aberration is provided at the total refraction calculator 146.

Synchronously with each of the polarized probing beams 126a and the plurality of additional beams 127a, the component of aberration caused by aberrations in the cornea surface 131 may simultaneously be determined. Because beams 126a and 127a are polarized light, they will partially reflect off of the cornea surface 131 as a polarized light beam 154a, in the case of probing beam 126a, at an impingement point 132 and as reflected polarized light 153a in the case of probing beam 127a and at impingement point 133. Because the light reflects from the cornea at an angle corresponding to the angular position of the anterior cornea surface 131 at the point of impingement 132, reflected beam 154a diverges from beam 126a, depending upon the refractive characteristics of the cornea 131 at the impingement point. Beam 154 is directed by beam splitter 128 to polarizing beam splitter 140 along path 154b. The beam 154b passes through polarizing beam splitter 140 because it is polarized light that was reflected from the cornea surface and travels along path 154c so that its position may be detected by a second photodetector 156. To facilitate determination of the reflective angle of beam 154 off of the cornea, the distance from the cornea to a semitransparent scattering screen 158 is a known quantity so that the offset distance 160 of the beam 154c impacting scattering screen 158 is indicative of the topography of the cornea surface 131.

The scattering screen 158 causes, the light beams 154c and 153c, to scatter, as schematically depicted with scattering diagrams 155 or 157. The position 160 or 159, with respect to the optical centerline 161, is imaged by a lens 162 onto the second photodetector 156. Once again, the second photodetector 156 may comprise an array of x and y photodetectors using a beam divider to determine the x-y position 160 for the reflected light from the cornea. This information is provided to a cornea cause refraction calculator 164.

The data from both total refraction calculator 146 and from he cornea cause refraction calculator 164 is fed into a comparator 168 and also to memory 170. The comparator information produces data, including the total refraction for each point, the cornea cause refraction for each impingement, i.e., for each shifted probing beam and may also determine the component of the refraction aberration due to components of the eye other than the cornea. From this information, a map of refractive characteristics of the eye is reconstructed in a map reconstruction unit 172. The reconstruction map produced at 172 may be displayed at a display 174, such as a CRT screen or a color printout. All of the total refraction calculator 146, the cornea cause refraction calculator 164, the comparator 168, the memory 170, the map reconstruction unit 172 and the display 174 may be separately provided or alternatively may be included in a computer system and display screen and/or printer schematically represented by system dash lines 148 in FIG. 4

FIG. 5 is an enlarged schematic view of a portion of the device for synchronous mapping of the total refraction and its component parts, better schematically depicting the paths of the probing beams 126a and 127a, as well as the backscatter light path 126c, 126d, 126e and 126f to a photodetector 146. The photodetector 146 is shown comprising an x component detector 88 and a y component detector 89. Further, the beams respectively directed or passing through the polarizing beam splitter 140 are more clearly depicted and the points of impingement on the semitransparent light scattering screen 158 are more clearly demonstrated.

The semitransparent light scattering screen 158 may, for example, be milk glass or translucent fluorescent light cover material having a substantially homogeneous characteristics so that polarized light beams impacting at any point produce the same relative intensity and same relative diffusion by which the position of such light beams may be detected with position sensor 156. The second position sensor 156, although not depicted, may also be constructed similarly to position sensor 146 so that x component sensor array 88 and y sensor component array 89 are used in combination to get an x-y position sensor.

Figure 6:
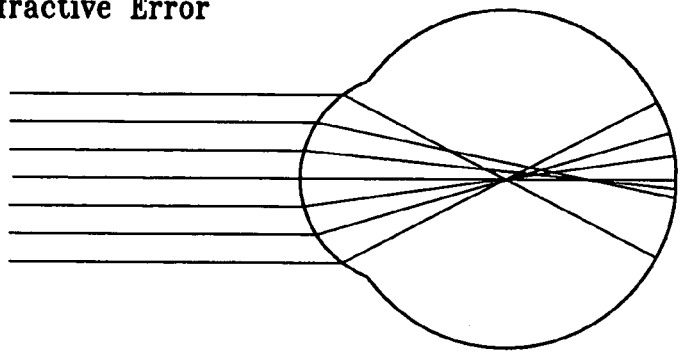
FIG. 6 schematically depicts an eye with refractive error as determined using ray tracing technology.

FIG. 6 schematically depicts the optical channels of one embodiment of the total aberration portion of the refractometer of the subject invention. A spatially defined parallel beam input channel 59 extends from a light source such as a laser or other low diffusion light source up to the eye of a patient 98. In one preferred embodiment a 650λ laser was employed. Along the spatially-defined parallel beam input channel is a cylindrical telescope 62 including two lenses 64 and 66. Light from the cylindrical telescope enters the deflector 68. The deflector 68 is preferably an acousto-optical deflector electronically controlled by a control unit such as a computer. Alternatively a galvanometric mirror deflector or the like could be used. Two coordinate deflectors or angular direction mechanisms may be used as a deflector 68. A reflection mirror or mirror prism 70 reflects the light beam through a telescopic system 72, including preferably, but not necessarily, a lens 74, an entrance aperture 76, lenses 78 and 79 and an exit aperture or field stop 80. The polarized light beam passes from the field stop 80 to collimating lens 82 and is deflected by mirror 71 and passes transparently through beam splitter 100 and interferential beam splitter 92 en route to the eye 98.

Light sources placed in front of the eye are used to align the visual axis of the eye with the optical axis of the instrument. Preferably a plurality of orthogonally placed light emitting diodes (LEDs) 102, for example emitting at a λ of 940 mm could be employed. Light produced by LEDs 102 is reflected off the cornea and imaged by camera 112. When the reflected light aligns with preset targeting parameters, the instrument is in the proper alignment and therefore in the permissive mode for firing of the spatially resolved parallel beams formed along channel 59.

The illuminated eye is then ultimately imaged by camera 112 as the image passes through the beam splitter prism 92 and is redirected at beam splitter 100 to pass through optical elements 104, 106, 108 and 110 to finally fall upon the CCD camera 112.

A retinal spot position detecting channel 99 is used to detect the position of reflected spots from the retina of eye 98 created by the input channel and includes a interferential polarization beam splitter 92 that directs non-polarized reflected light from the retina of eye 98 to a position sensor.

In one embodiment of a photodetection position sensor as shown in FIG. 6 there is a beam splitter 94 that splits the image directing one component of the nonpolarized retina image through an optical lens 90 to a "x-coordinate" photodetector 88 and directs another component of the image through optical lens 91 to a "y-coordinate" photodetector 89. Preferably, the orthogonally placed photo detectors 88 and 89 are high resolution linear array photodetectors and the position measurement created on those detectors may be used directly to provide XY coordinates for the measurement of the position of reflected spots on the retina of eye 98. Instead of using linear array detectors, an actual XY matrix photo detector or a CCD detector with its own objective lens can be used to replace the beam splitter 94 lenses 90 and 91 and the linear array photodetectors 88 and 89. One benefit of the linear arrays is that they provide for a large range of aberration detection that exceeds the range of a simple quadrant photodetector. For example, a typical quadrant photodetector may be useful for detecting aberrations of a range of about ±3 diopters while linear arrays can accommodate a range of approximately ±10 diopters. Another option is to use lateral position sensing detectors. The drawback of using a quadrant detector is in the dependence on the shape and size of the light spot imaged on its surface. Multi-element detectors like 1D or 2D arrays (linear arrays or CCD) as well as lateral position sensing detectors are free of this drawback. In yet another embodiment, the photo detector may be a 2-dimensional or x-y photodetection matrix or a CCD sensory matrix.

Figure 14:
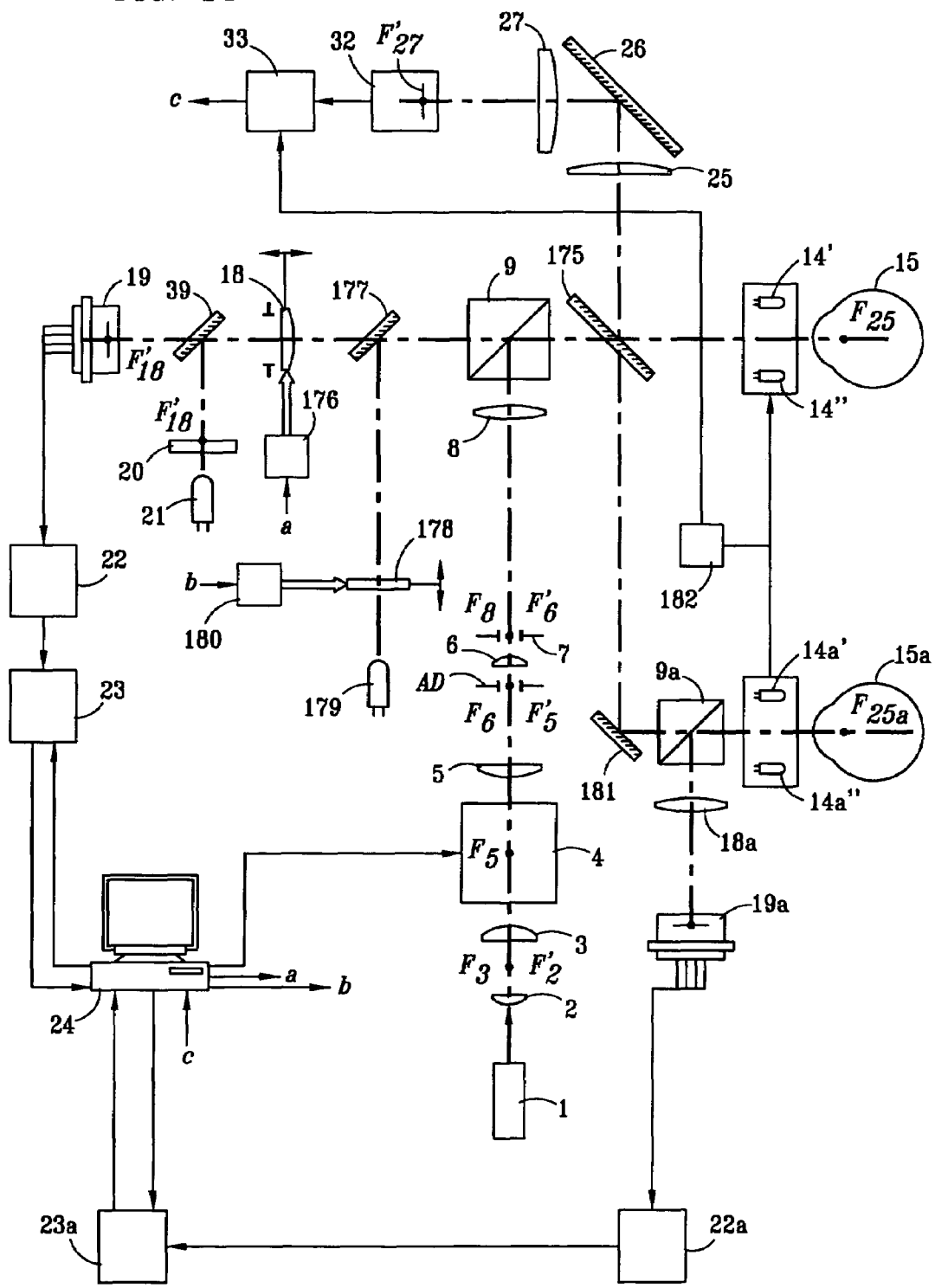
FIG. 14 is a schematic illustration of the operation of another embodiment of a device for measuring the total transverse aberration of a laser beam on the eye retina.

Details of the embodiment depicted in FIG. 6 are further explained with reference to FIG. 14 below. The position of a spot of targeting light reflected back from a reflection spot on the fovea of the retina can be determined using reflection beam splitter 94 to direct a first portion of the reflected nonpolarized light from the retina spot through lens 90 to an x-direction linear array photodetector 88 for measuring changes in position only in one direction, for example in a x-direction. A second portion of the reflected nonpolarized light, substantially identical to the first portion, is directed through lens 91 to a y-direction linear array photodetector 89 for detecting changes in position only in a direction at ninety degrees to the first direction, for example the y-direction. The change in the x-y position is measured by calculating the position of the center of light intensity of the light spot projected on the linear array 88 (x direction) and linear array 89 (y direction).

Light source 96 and condenser lenses 77 and 79 enable homogeneous irradiating of the linear arrays 88 and 89, thus checking their homogeneity at servicing. Light emitting diode 96 and condenser lenses 77, 79 form a wide beam for calibrating photodetectors 88 and 89. If any of the elements is out of tolerance, its output can be corrected at signal processing procedures.

A fixation target channel 85 preferably comprises a light source. In a preferred embodiment the light source is a green 565 λ LED 84. The light may be transmitted through lenses 74 and 75 and directed by prism 86 and through beam splitter 100 which has wavelength differentiating optical coatings. Fixation target is positioned on the optical element 106. The light beam from LED 84 passes through lenses 104 and 108 and fixation target 106 and is reflected off of the mirror 110. The fixation target light passes back through the lens 104 and is redirected by beam splitter 100 at 90 degrees out toward the eye for the patient to visualize the image as coming from the location of the surface 110 which image can be moved from near fixation to far fixation or adjustable anywhere in between and this may be used for changing the eye accommodation over a period of time and simultaneously taking a series of measurements including spatially resolved aberration refraction measurements as well as pictures on the CCD camera 112. This produces a time lapse imaging of the eye and measurements of the aberration refraction as it cycles through different fixation target distances. The different target fixation distances may be automatically moved or adjusted from near to far using electro mechanical adjustment means that may be synchronized with the measurements and/or images taken on a time lapse basis.

The instrument described herein was developed to provide a total aberration refractometer able to accurately and quickly provide a refractive map of either emmetropic or ametropic eyes without accommodation error.

Figure 7:
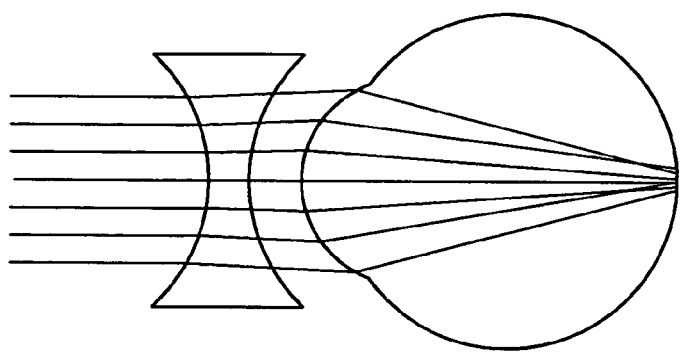
FIG. 7 schematically depicts the eye with refractive error as measured in FIG. 6 and with refractive correction applied as determined using sphero-cylindrical components of correction.

FIG. 7 shows a functional diagram of another embodiment of the subject instrument for measurement of the total aberrations in the eye and total refraction non-homogeneity. A light source whose radiation is used for the ray tracing of the eye is provided, as for example, by laser 1. A telescopic expander comprising for example lenses 2 and 3 provides a normal functioning of a two-coordinate acousto-optic deflector 4 preferably consisting of two single-coordinate deflectors. A telescopic laser-beam narrower is formed by lenses 5 and 6 with an aperture stop or diaphragm AD located at the common foci of the lenses 5 and 6. A field stop or diaphragm 7 is placed at the back focus of lens 6 so that its image formed by the telescopic narrower in the back-pass is located between the single-coordinate deflectors. With this placement, the redistribution of the light illuminance in the light spot on the pupil is minimized when the angular position of the laser beam is varied at the exit of the single-coordinate deflectors. The front focus of a collimating lens 8 is aligned with the center of the field stop or diaphragm 7 to ensure telocentric passage of rays through interferential polarizing beam splitter 9.

An ametropia compensator is schematically depicted as a varifocal group of lenses 10 and 11, adjustable to compensate for the patient's eye ametropia. One of the lenses is mounted on a movable base connected to actuator drive 38. An accommodation controller is schematically depicted as lenses 16 and 17 that constitute a varifocal group of lenses for accommodation control of the patient's eye.

An objective lens 18, at whose focal point the photosensitive surface of a position-sensitive photodetector 19 is located, is intended to form an image of the irradiated retina in the plane of the photosensitive surface of the position-sensitive photodetector. The photosensitive elements of the photodetector are connected through a preamplifier 22 and an analog-to-digit converter 23 to a computer 24. A beam coupler 39 is movably mounted between the objective lens 18 and the photodetector 19 to optically conjugate the plane of the test-target or plate 20 with the photosensitive surface of the first photodetector 19 as well as with the fovea surface. The plate 20 is needed to ensure the fixation of the patient's gaze. Located behind the plate 20 is a light source or radiator 21 serving to illuminate the plate.

Elements 25 through 30 comprise a microscope whose objective lens consists of lenses 25 and 27 together with mirror 26. A plate 29 with first coordinate-grid is preferably located at the back focal plane of a lens 27. A lens or a group of lenses 30, the front focal point of which coincides with the back focal point of the lens 27, comprises an eyepiece of the microscope. The beam splitter 28 serves to optically couple the retinal plane with the photosensitive plane of a TV camera 32 connected to the computer through a video signal conversion and input board, alternatively termed a frame grabber board, 33.

By means of a mirror 12 provided with an opening, the optical axis of the microscope is aligned with the optical axes of the ray tracing channel (elements 1-11) and the photoelectric arrangement for measuring the transverse ray aberration on the retina (elements 16-19).

In a preferred embodiment, four light-emitting diodes (LEDs) 14 are installed in a cross-wise configuration in front of the patient's eye. Each LED is preferably located in the same plane as each other LED, at an equal distance from the optical axis and perpendicular with the axis. The microscope and the LEDs comprise a system for the visual and television positioning of the instrument relative to the patient's eye. The microscope is installed so that the front focal plane of lens 25 coincides with the plane, where imaginary or virtual images of the LEDs 14, mirrored by the anterior corneal surface, are located.

Before the total refraction measurement process is commenced, the instrument is positioned relative to the patient's eye and the instrument is calibrated using the optical calibration unit 34-36. Movably mounted between the lens 11 and the LEDs 14 is a mirror 13 which serves to join the optical axes of the instrument and the optical calibration unit 34-36. In one preferred embodiment of an optical calibration unit, it comprises a meniscus or cornea simulator 34, liquid medium or vitreous simulator 35, and retina simulator 36. The retina simulator 36 is preferably movably mounted so that it can be moved along the optical axis by means of actuator or drive 37.

The instant measuring instrument incorporates a computer 24 or like device for controlling the acousto-optic deflector 4, analog-to-digital converter 23, and actuators or drives 37 and 38. The computer 24 or like device or devices may perform additional duties including, for example, mathematical processing and data storage, calculation and display of aberration parameters and the ocular refraction characteristics as well as provide setting measurement modes and implementation of automatic instrument alignment.

The instrument for measurement of the total eye refraction, in its preferred embodiment, functions in the following way. The light beam emitted, for example by laser 1, is expanded, collimated and directed to the acousto-optic deflector 4, which changes its angular position in accordance with the corresponding computer program. The telescopic narrower 5 and 6 reduces the beam thickness to the requisite magnitude. The center of the stop or diaphragm 7 is a point of angular "swinging" of the beam exiting from the telescopic narrower. Due to its positioning in the front focal plane of the lens 6, the aperture stop or diaphragm AD has its image in the back focal plane of the lens 8 which is aligned with the eye pupil. Further, because the stop or diaphragm 7 is positioned in the front focal plane of the collimating lens 8, angular swinging of the laser beam with the angle vertex located on the stop or diaphragm 7 is converted into parallel shifting of its optical axis after passing the lens 8.

If the patient's eye is ametropic, the axial movement of the lens 10 (or 11) converts the telocentric beam into a beam which diverges (in the case of myopia), or converges (in the event of hyperopia), so that the image of the diaphragm 7 is optically conjugated with the retina. This also ensures parallelism of the rays reflected by the retina in the zone in front of the beam splitter 9, which is necessary for its normal functioning.

The light entering the eye 15 of the patient is polarized in the plane shown in FIG. 7. Only that component of the returning beam depolarized by interaction with the retina is allowed by the beam splitter 9 to pass to the first photodetector 19. This protects the first photodetector from the polarized light reflected by the surfaces of the lenses 10 and 11 and by the cornea or the eye and which can produce an illuminance incompatible with determining the total refraction according to normal functioning of the instrument.

Lenses 16 and 17 and the objective lens 18 produce an image of the illuminated area of the retina in the plane of the first photodetector 19. In FIG. 7 the foci locations are designated as follows: $F_3$, $F_5$, $F_6$, $F_8$, $F_{25}$, and $F_{30}$, designating points of front foci of the corresponding lenses while $F_2'$, $F_5'$, $F_6'$, $F_{18}'$, and $F_{27}'$, designating points of back foci of the lenses.

Figure 8:
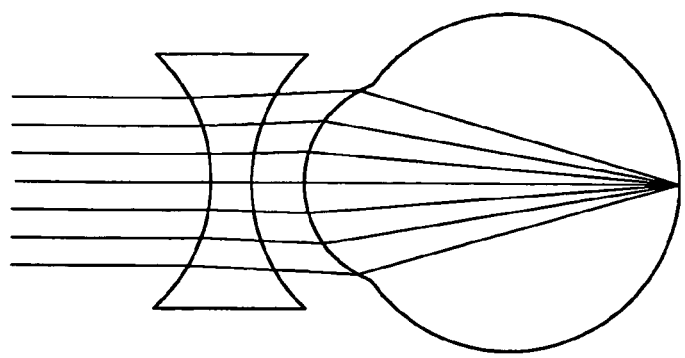
FIG. 8 schematically depicts the eye with refractive error as measured in FIG. 6 and with refractive correction applied to obtain a characteristic of maximum acuity as determined using components of correction defined with higher order Zernike or "custom" curve fitting to determine the correction to be applied to obtain the maximum acuity as the desired quality of vision.

In one more embodiment, presented in FIG. 8, the function of ametropia compensator is combined in the component 18 that is an objective lens for the photodetector 19. In this embodiment, target object 20 and photodetector 19 are positioned at equal distances from the lens 18. LED 21 irradiates the target object 20. The lens 18 is positioned by the patient in such a way that a clear image of target object 20 is seen. In this position, focal planes of the photodetector 19 and the eye 15 are conjugated. Positioning of the lens 18 can be implemented with the electric drive 176. This positioning can be done automatically. Accommodation control is executed with another target object 178, irradiated by the LED 179, and positioned by an electronic drive 180. Both drives, 176 and 180, are connected with computer 24. Accommodation target object 178 is coupled with optical axis by the mirror 177. Colors of LEDs 21 and 179 should be different for their easy identification. For example, conjugation is made with red LED 21, and accommodation follows with green LED 179.

Figure 9:
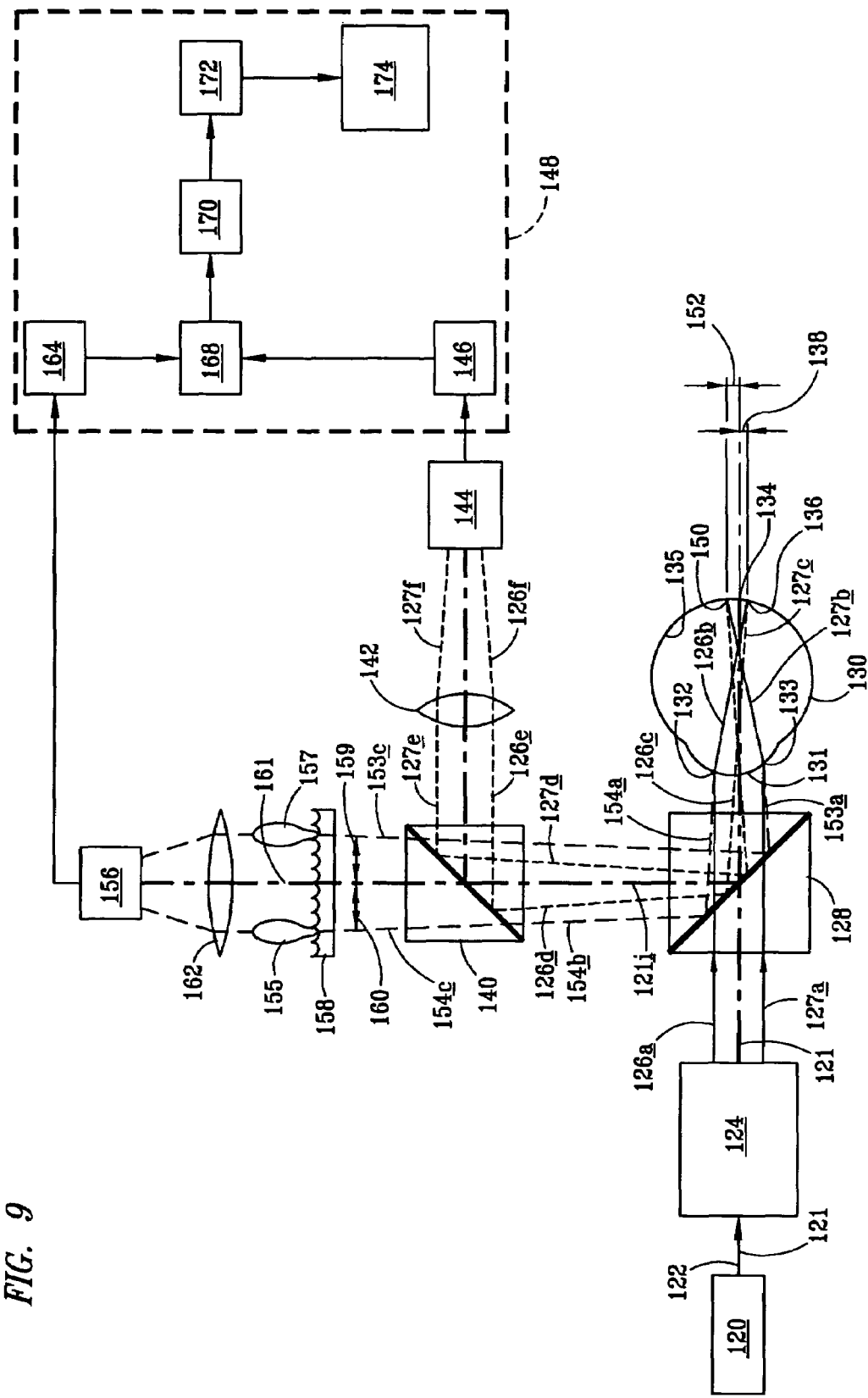
FIG. 9 is a functional schematic drawing of a device for synchronous mapping of the total refraction non-homogeneity of the eye and its refractive components.

Still another embodiment of the invention, schematically shown in FIG. 9 and based generally on the configuration presented in the FIG. 8, enables simultaneous investigation of both eyes 15 and 15a. According to the design shown in FIG. 9 this embodiment beneficially contains an additional channel for the second eye 15a. The implementation is such that the common laser probing is used for both eyes due to two beam splitters 175 and 181. Optical and electrical components 9a, 14a, 18a, 19a, 22a, and 23a have the same roles as the corresponding components 9, 14, 18, 19, 22, and 23 at measurement of the first eye 15. Control unit 182 switches the infrared LEDs 14 beam splitters 175 and 181. Optical and electrical components 9a, 14a, 18a, 19a, 22a, and 23a have the same roles as the corresponding components 9, 14, 18, 19, 22, and 23 at measurement of the first eye 15. Control unit 182 switches the infrared LEDs 14 and 14a to alternatively get irradiated first and second eye 15 and 15a respectively. In this way, images of the eyes can be displayed simultaneously, for example, on the left and right parts of the monitor's screen. Described implementation enables separate adjustment and advantageously provides simultaneous measurements on both eyes.

In the various embodiments of FIGS. 7, 8, and 9 the laser beam is positioned by the computer and the acousto-optic deflector so as to enter the pupil within the requisite refraction measurement zone. If the optical system of the eye has aberration refraction, the light image of the stop or diaphragm 7 on the retina is displaced from the axis, which results in the corresponding displacement of the illuminated zone image on the photosensitive surface of the position-sensing photodetector 19.

Figure 10:
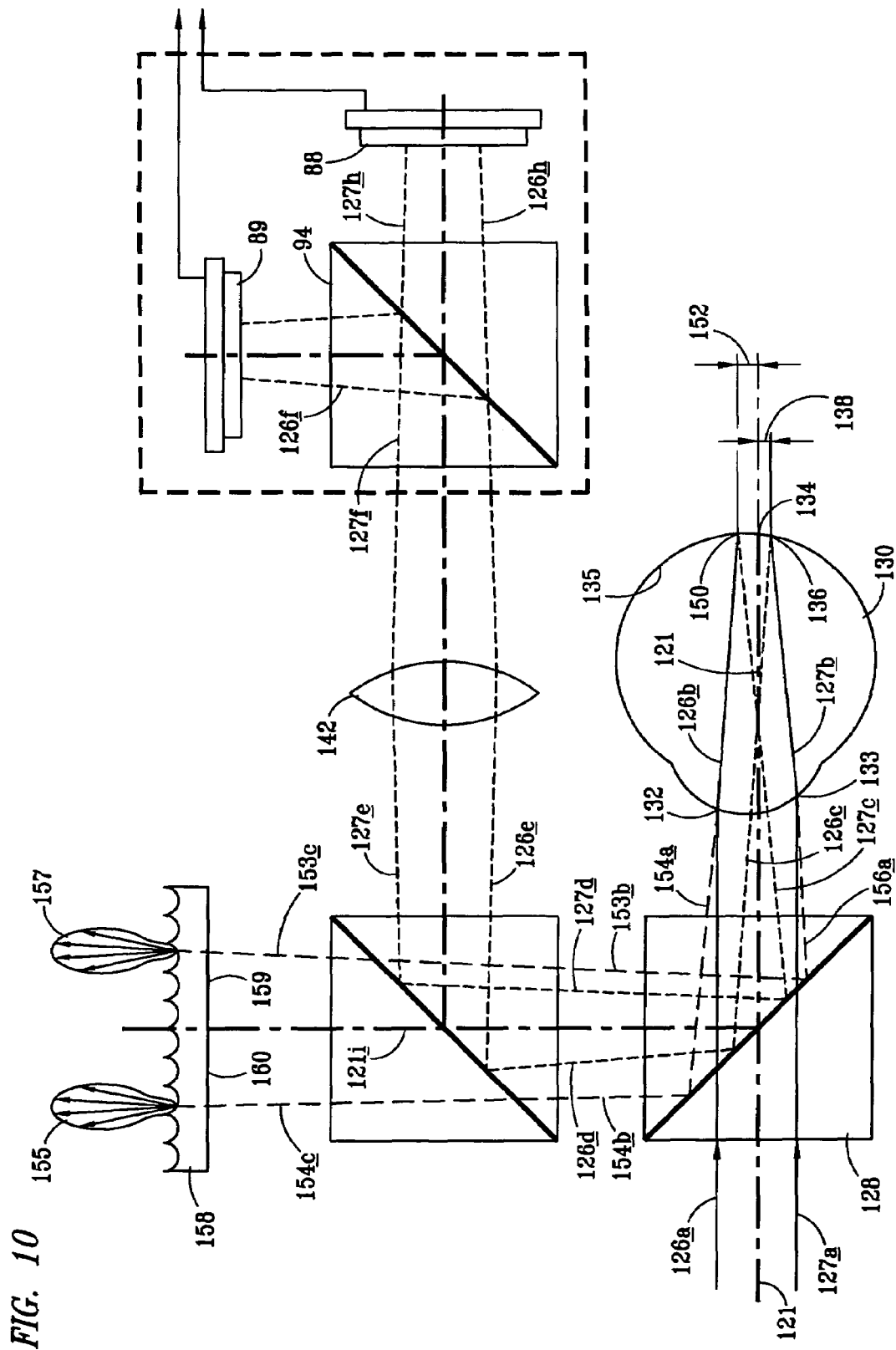
FIG. 10 is a schematic depiction of an eye under investigation in which the theoretical aspects of the total eye refraction determination and also the corneal component of refraction may be more fully understood.

If photodetector 19 is a four-quadrant photodiode, as, for example, that shown diagrammatically in FIG. 10, having quadrants 1, 2, 3 and 4, an aberration displacement of the light spot δx, δy on the retina can be given by the formula:

$$\delta x = \frac{\beta}{2}\left[\frac{(U_1 + U_4) - (U_2 + U_3)}{U_1 + U_2 + U_3 + U_4}\right] \cdot b,$$

$$\delta y = \frac{\beta}{2}\left[\frac{(U_1 + U_2) - (U_3 + U_4)}{U_1 + U_2 + U_3 + U_4}\right] \cdot b,$$

where

Figure 11:
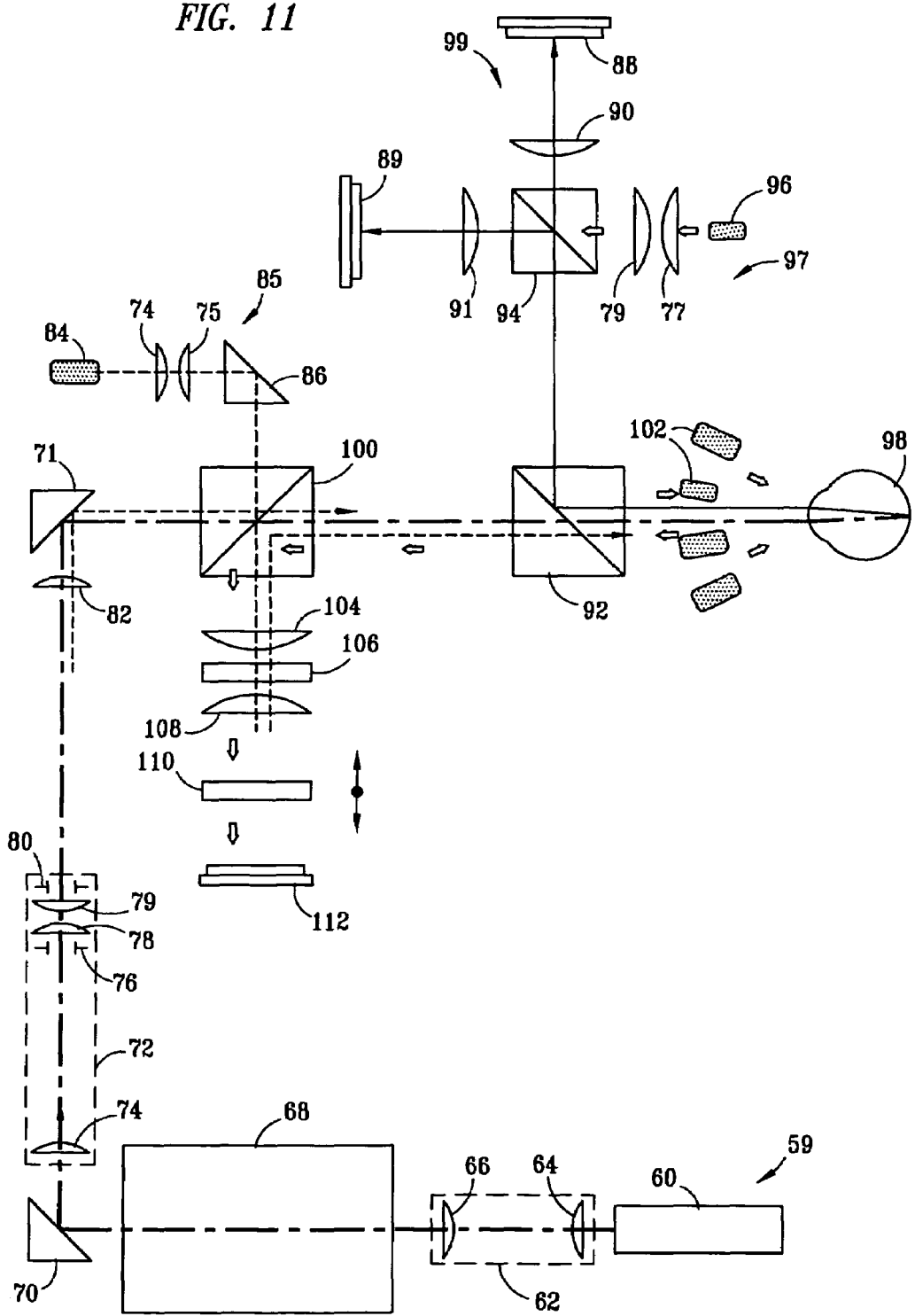
FIG. 11 is a schematic diagram of a preferred alternative embodiment of an aberration refractometer employing ray tracing technology useful according to certain aspects of the present invention.

If photodetector 19 is a lateral position sensing detector, as shown in FIG. 11, having a pair of x-direction electrodes 1 and 2, and a pair of Y-direction electrodes 3 and 4, an aberration displacement of the light spot δx, δy on the retina can be described as follows:

$$\delta x = \beta\left[\frac{U_1 - U_2}{U_1 + U_2}\right] \cdot a,$$

$$\delta y = \beta\left[\frac{U_3 - U_4}{U_3 + U_4}\right] \cdot a,$$

where β is the transverse magnification between the planes of photodetector and retina, $U_1$, $U_2$, $U_3$ and $U_4$ are the signals coming from the electrodes, 1, 2, 3 and 4 correspondingly, and a is a scaling coefficient depending on the electrical parameters of the lateral detector.

Figure 12:
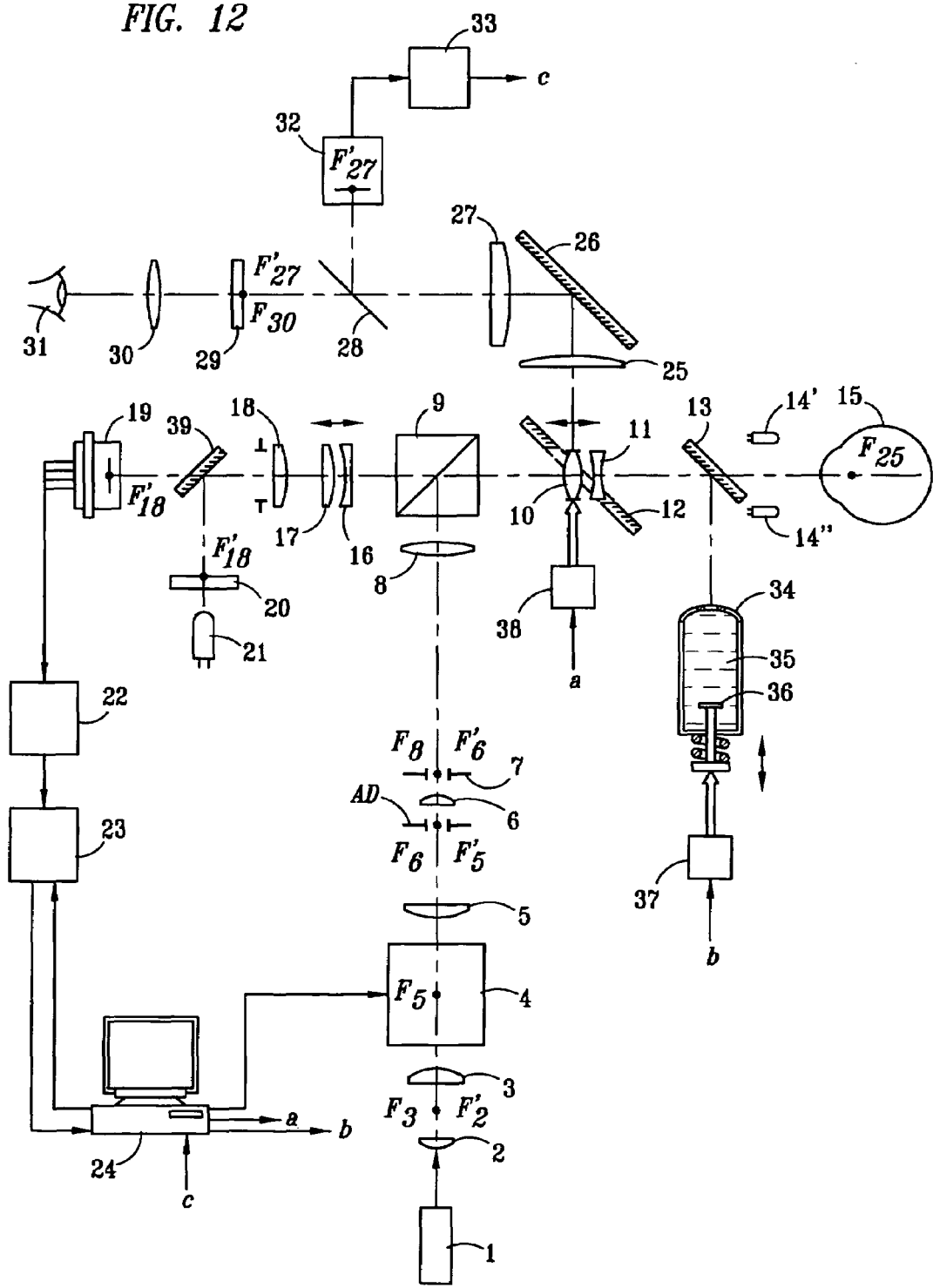
FIG. 12 is a functional schematic diagram of an instrument for measuring total aberration refraction.

The principle of operation relating to the positioning the instrument in relation to the patient's eye is illustrated in FIG. 12. The collimating system 50 corresponds to the elements 39, 18 and 17, 16 of FIG. 7 (if the eye is accommodated at a finite distance). Point A is the light radiator and gaze fixation point and is formed by the elements 20 and 21 in FIG. 7. The mirror 56 with an opening corresponds to element 12 of FIG. 7. The microscope objective lens 52 is comprised of the elements 25-27 of FIG. 7 while the microscope objective image plane 54 (FIG. 7) corresponds to the element 29 (FIG. 7). $B_1$ and $B_2$ are light radiators corresponding to the LED 14 of FIG. 7. $B'_1$ and $B'_2$ are primary images of the radiators while $B''_1$ and $B''_2$ are secondary images of the radiators.

As can be seen from FIG. 12, the fixation of the gaze on the point A, located on the optical axis of the instrument, does not guarantee the coincidence or alignment of the visual axis of the eye and the optical axis of the instrument because the eye sees the point A on the fovea even when Δ≠0. The fixation of the gaze on the point A is ensured only when the above axes are parallel.

Taking into account that the largest contribution to the optical power of the eye is made by the anterior surface of the cornea, the visual axis line is assumed to be the line passing through the fovea center and the vertex of center of curvature of the front surface of the cornea. If the radiator $B_1$ is positioned in front of the patient's eye, then, due to reflection of the light from the anterior or front surface of the cornea, this surface functioning as a convex mirror, forms an imaginary or virtual image $B'_1$ of the radiator, located symmetrically to the axis in accordance with the laws of geometric optics.

When several radiators, such as for example, $B_1$ and $B_2$, are positioned in front of the patient's eye symmetrically to the optical axis of the instrument (FIG. 12), their secondary images $B''_1$ and $B''_2$ will be shifted in the image plane of the microscope objective lens aside from the axis if Δ≠0.

Thus, to make the optical axis of the instrument and the visual axis of the eye coincide, two conditions must be satisfied: the patient's gaze is fixed on the point A and the images $B''_1$ and $B''_2$ are centrally positioned in relation to the axis of the objective lens 52. The positioning can be checked using the coordinate grid provided on the plate 29 (FIG. 4) or using the monitor screen when the TV channel is utilized. When the image of the eye is aligned at all points with concentric locations on the grid or the TV screen, the measurement controller is armed for taking a spatially resolved set of refraction measurements. The operator can than activate the measurement that can take only a few milliseconds. The measurements are "grabbed" in the grabber board and stored for producing an aberration refraction map as in FIG. 15. The measurements can also be activated automatically when the proper alignment is detected. Further, according to one embodiment of the invention, a plurality of measurements can be made sequentially during the occurrence of a predetermined event, such as through a sequence of movement of the eye target from a "near" accommodation distance to a "far" or infinity accommodation distance. A plurality of measurement images can be captured or automatically grabbed and stored over a time period or while any other changes are occurring for which eye measurements might indicate a dynamic change in the refraction of the eye.

The coincidence of the points $B''_1$ and $B''_2$ with the surface or plane 54 is indicative of setting the fixed working distance between the instrument and the eye which is the result of the focusing of the images $B''_1$ and $B''_2$ on the surface 54.

The point of gaze fixation is created by locating the mirror 39 (FIG. 7) on the optical axis of the instrument. The radiators 14' and 14" play the part of the radiators $B_1$ and $B_2$ shown in FIG. 12.

Another embodiment of eye instrument alignment can be implemented using manually or automatically operated measurement of the pupil edges; forming a figure, approximately a circle. Its center does not coincide usually with the center of symmetry of four reflexes, two of which $B''_1$ and $B''_2$ are shown in FIG. 12. This non-coincidence can be taken into consideration at further signal processing.

The calibration of the instant aberration refraction instrument may be effected using the optical calibration unit. The optical calibration unit can be made to incorporate known aberrations at the corresponding cornea simulator 34 measurement points. For example, the aberration may be determined by the computer using special optical design programs. If, for example, the front surface of the lens 34 is ellipsoidal, then the aberration refraction at all the points of the pupil is equal to zero.

When an ametropy compensator is used, nonparallel laser beams will enter the optical calibration unit. This will result in a standard aberration of defocusing; to compensate for this aberration, the retina simulator can be moved along the optical axis by means of the actuator 37 to the focus point. Thereby, the fovea can be optically conjugated with the retina simulator.

Systematic errors of measurements of the transverse aberration will be evidenced by the deviation of the measurement results from the estimated data. Such determinable systematic errors can be taken into account when measuring actual total ocular aberrations.

The calibration by comparison with the optical calibration unit is preferably performed automatically before measuring the ocular aberrations by locating the mirror 13 on the optical axis of the instrument.

Figure 13:
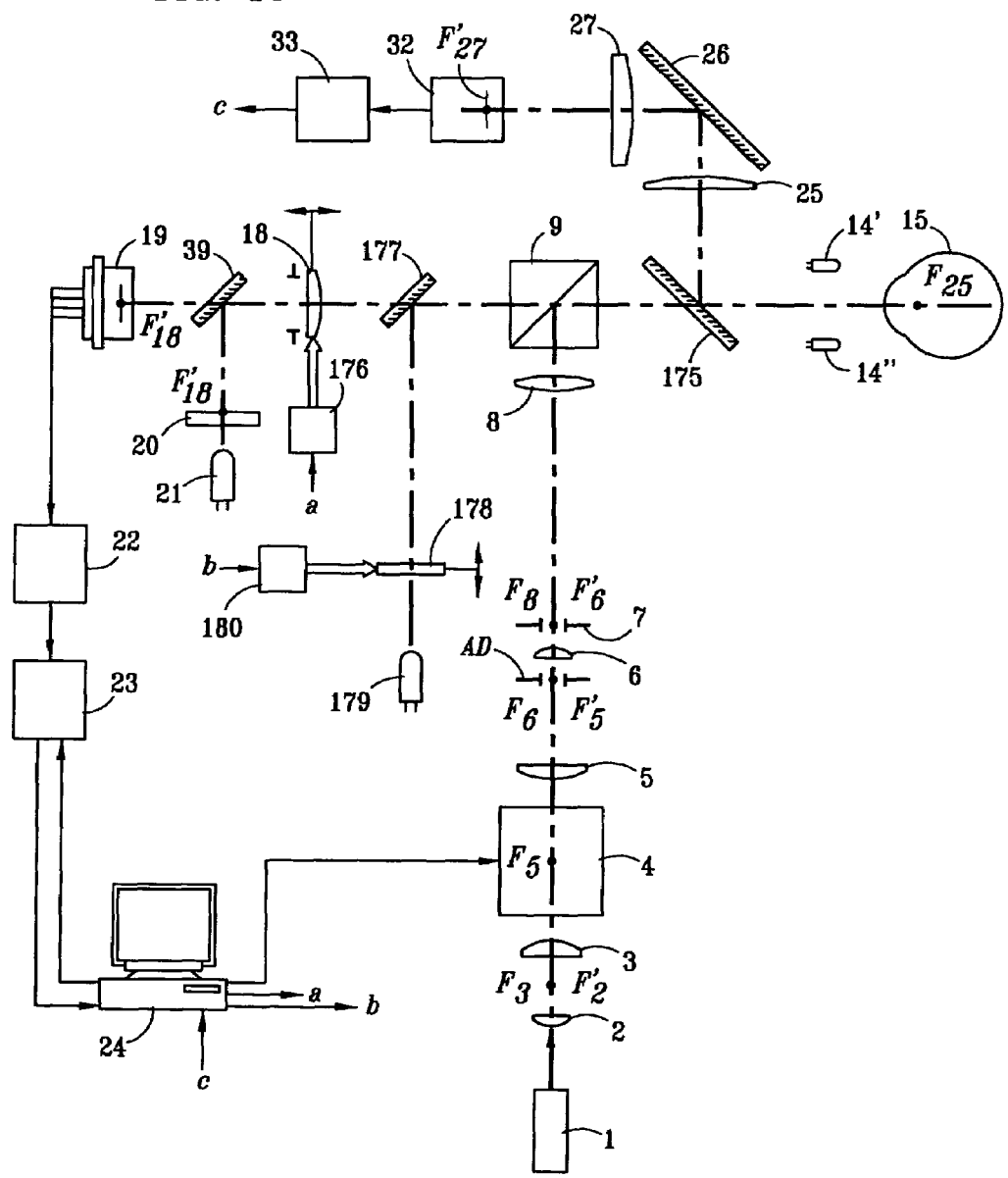
FIG. 13 is a schematic illustration of the operation of one embodiment of a ray tracing device for measuring the total transverse aberration of a laser beam on the eye retina.

Prior to the ray tracing of the patient's eye the mirrors 13 and 39 are withdrawn from the light path entering the eye and then the light passes to the photodetector. The aberration displacement of the image of the light spot on the fovea is measured at a set of points on the cornea corresponding to an ocular ray tracing grid chosen by the operator. An example of a grid or an allocation of measurement points on the pupil is shown in FIG. 13.

The data on measurement of the transverse aberrations on the retina $\delta x (\rho, \phi)$ and $\delta y (\rho, \phi)$ are used for further calculations of the coefficients of the Zernike polynomials by means of the least squares method in order to approximate the function of the total wave aberration of the eye. The wave aberration function is then used to calculate the local total refraction at any point of the pupil. In addition, the approximation makes it possible to determine or reconstruct the nature of local aberration refraction in that small axial zone of the pupil, where it is impossible make accurate direct measurement of refraction.

In one experiment conducted using this instrument in which five replicate tests were performed and the results averaged, the laser beam total aberration on the retina at 65 points of the pupil was been performed in within 12 milliseconds with no more that 5 mW of light radiation entering the eye.

Figure 15:
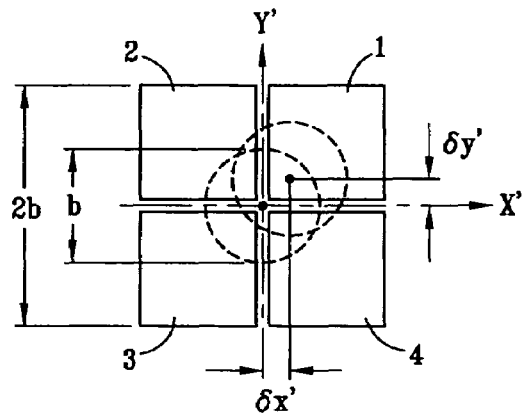
FIG. 15 is a schematic illustration of the operation of yet another embodiment of a device for binocular measuring of the total transverse aberration of a laser beam on the eye retina of both of a patient's eyes substantially simultaneously.
Figure 16:
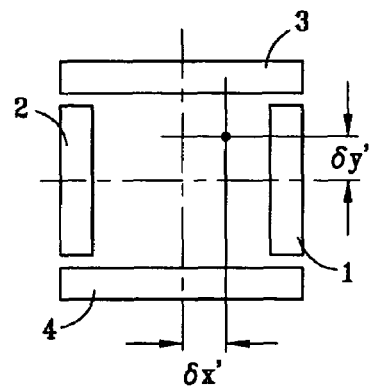
FIG. 16 is a schematic illustration of the operation of the lateral position sensing detector having a pair of X direction electrodes and a pair of Y direction electrodes.
Figure 17:
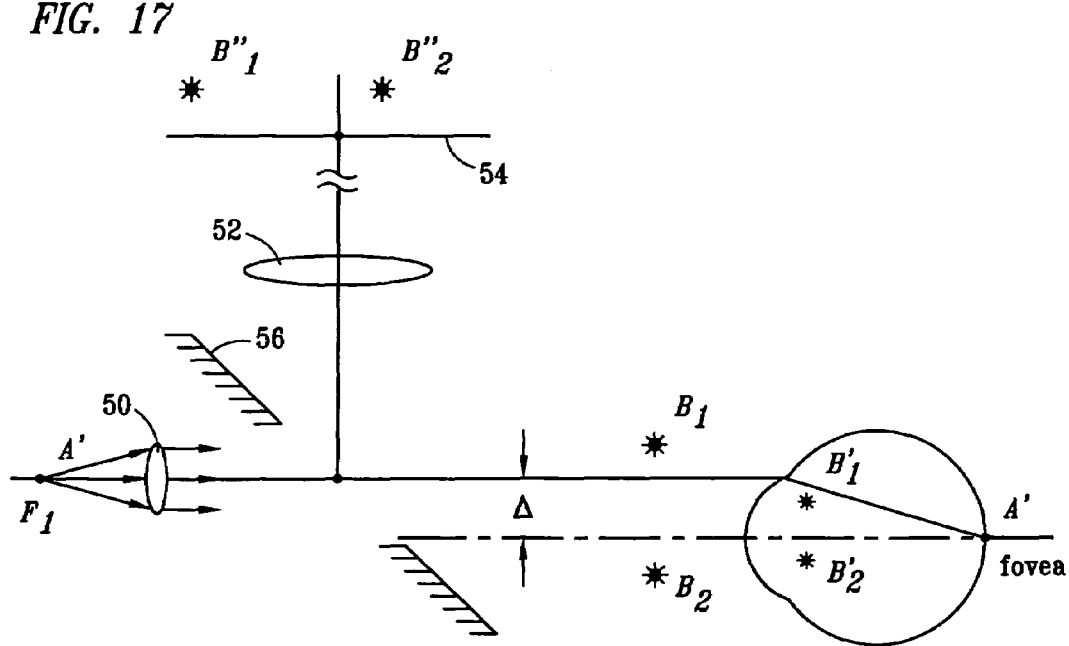
FIG. 17 is a schematic illustration of the principle of operation of the means for positioning the measuring device in relation to the patient's eye.
Figure 18:
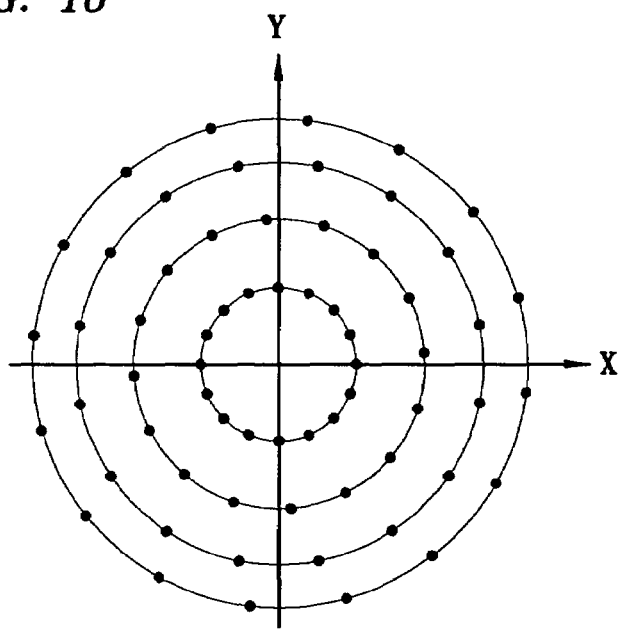
FIG. 18 is an example of a map showing the location of ocular refraction measurement points, constructed with the aid of a computer.
Figure 19:
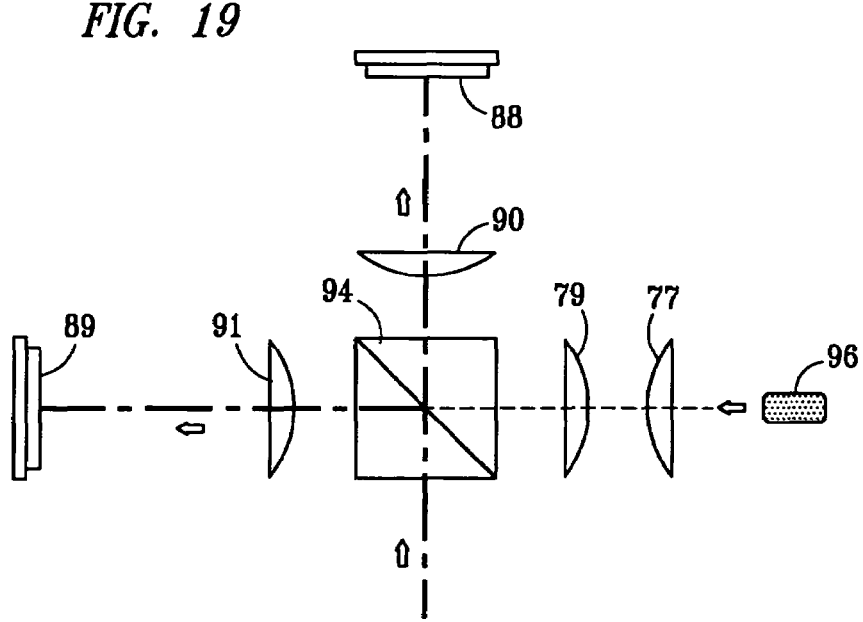
FIG. 19 is a schematic illustration of a photodetector using linear array detector components.
Figure 20:
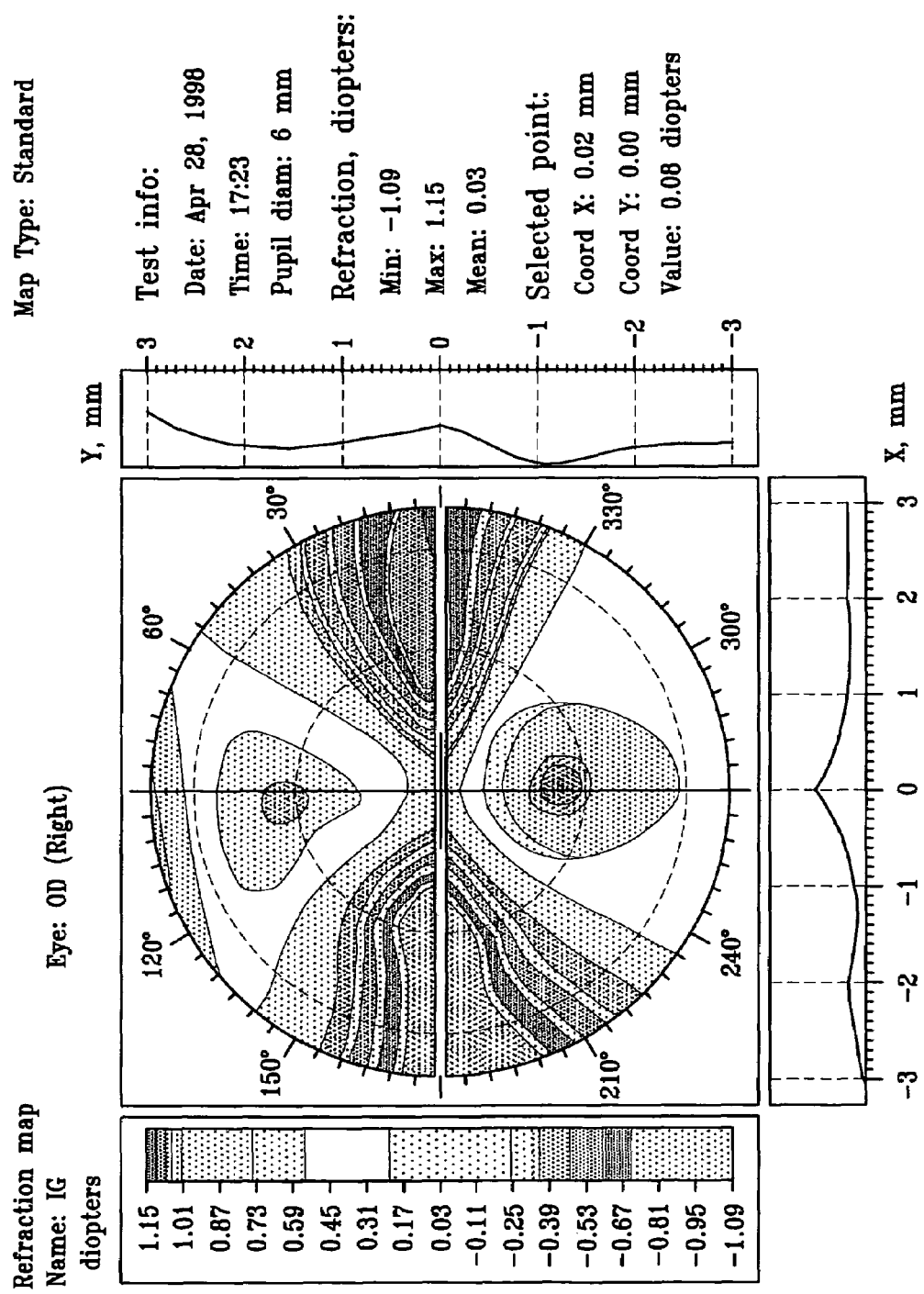
FIG. 20 is an example map showing the total aberration refraction of the eye, under consideration, constructed with the eye total aberration refractometer portion of the subject invention.

FIG. 15 is an example of an ocular aberration refraction map constructed with the use of the total eye aberration refractometer portion of the invention.

The extremely fast measurement permits the computer control program to cause a plurality of spatially resolved aberration measurements to be made in a very short period of time. The control program in one embodiment automatically activates a plurality of measurements coordinated with a series of adjusted accommodation fixation distances and automatic determination of proper eye alignment to receive a series of data measurements from the retinal spot position detecting channel. A series of refraction measurements for a dynamic eye refraction system is produced. Spatially resolved refraction measurements can be automatically programmed and automatically made during a variety of dynamic changes overtime such as varying accommodation or during normal functioning of the eye under a variety of predetermined conditions and internal or external changing conditions such as light illumination (scotopic, mesopic, and photopic).

Figure 21:
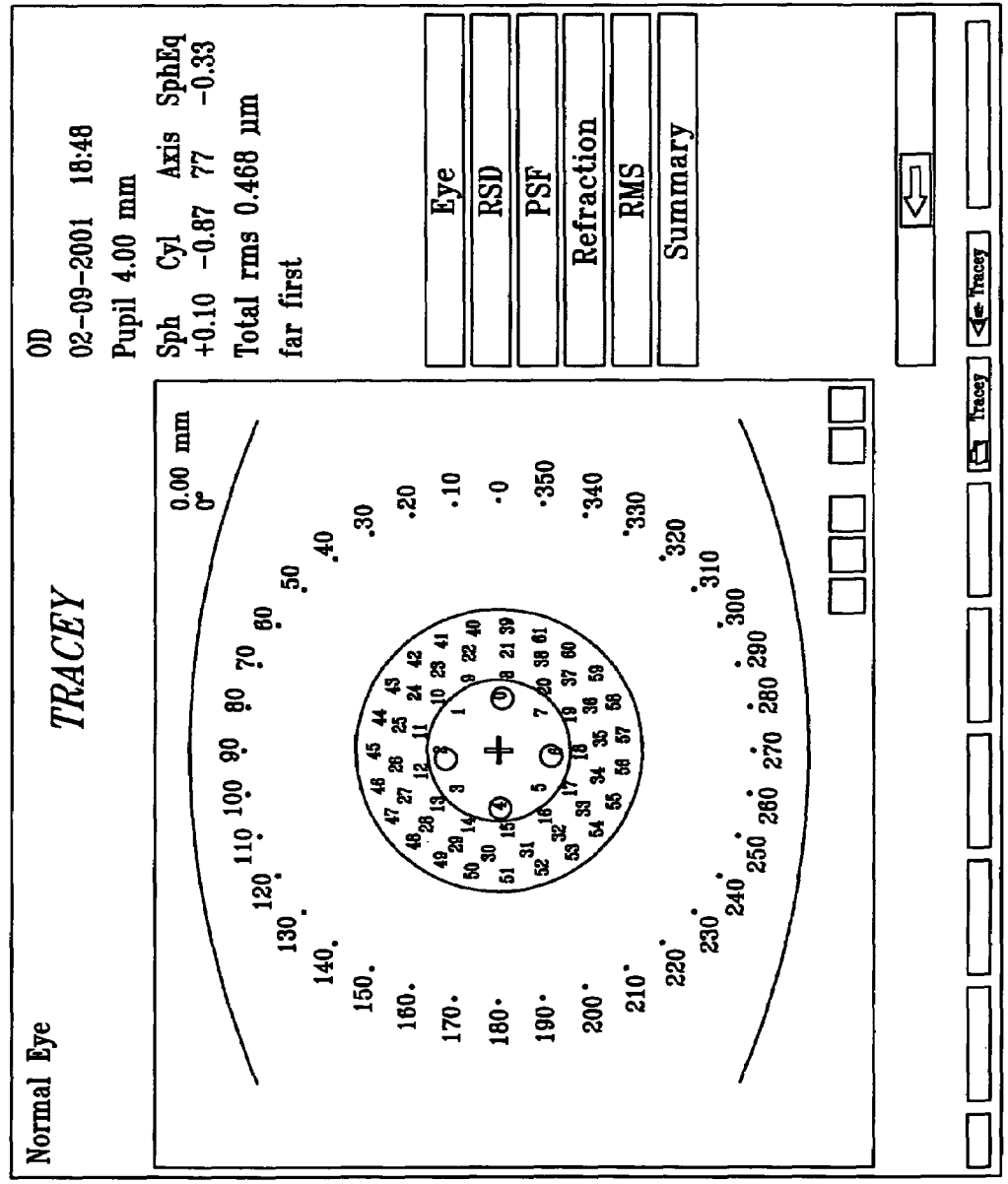
FIG. 21 is the pupil of a normal eye with beam points of entry used to produce retinal spot diagrams with ray tracing technology.

FIG. 21 is the pupil of a normal eye with beam points of entry used to produce retinal spot diagrams with ray tracing technology.

Figure 22:
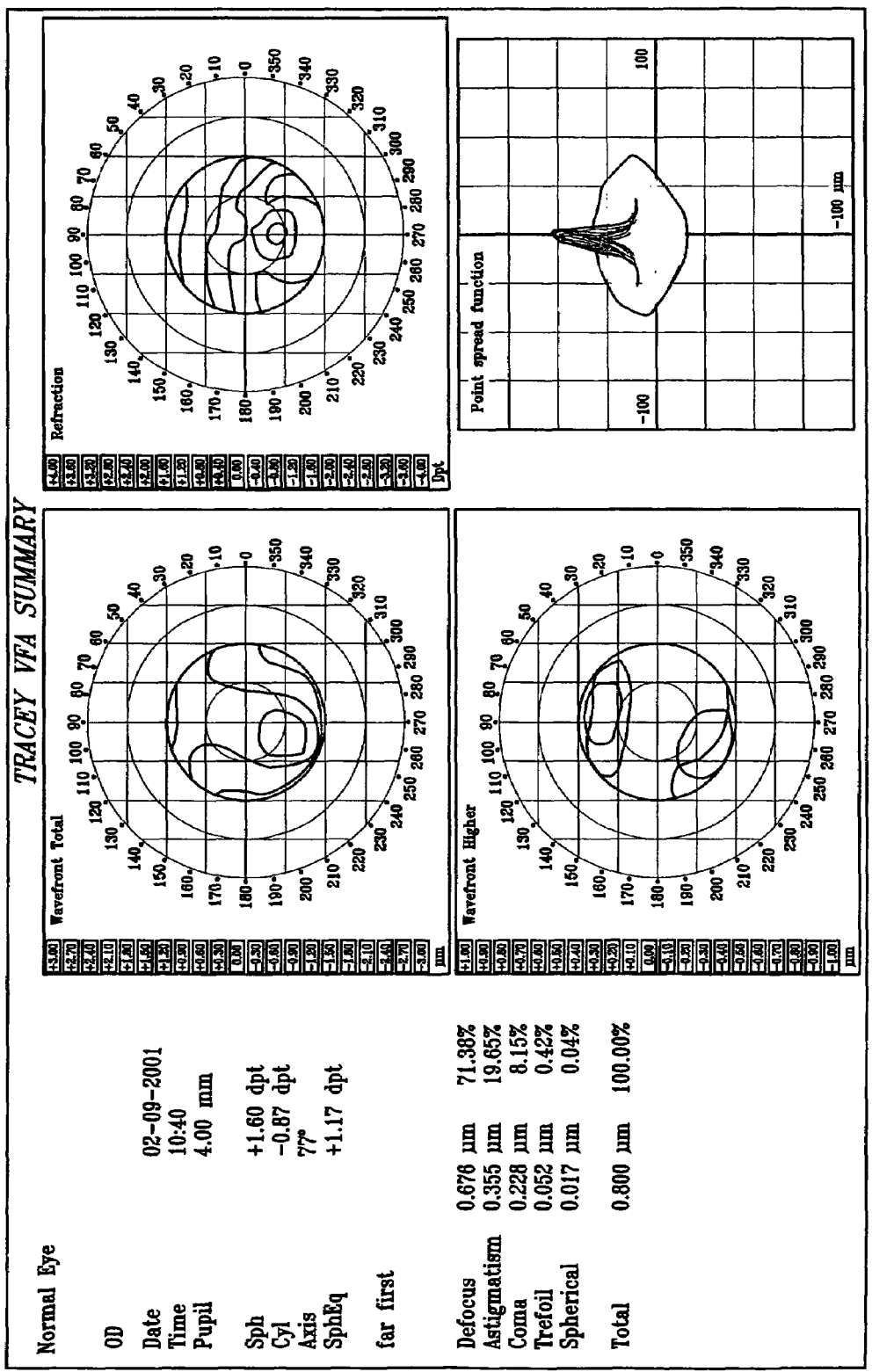
FIG. 22 shows diagrams of wavefront refraction, wavefront total, wavefront higher order distortions, and point spread function.

FIG. 22 shows diagrams of wavefront refraction, wavefront total aberration, wavefront higher order distortions, and point spread function as determined with ray tracing technology for a normal eye with some small degree of aberration including both defocus and astigmatism components. The color coding indicates based upon the scale shown at the left, the severity and location of the aberration.

Figure 23:
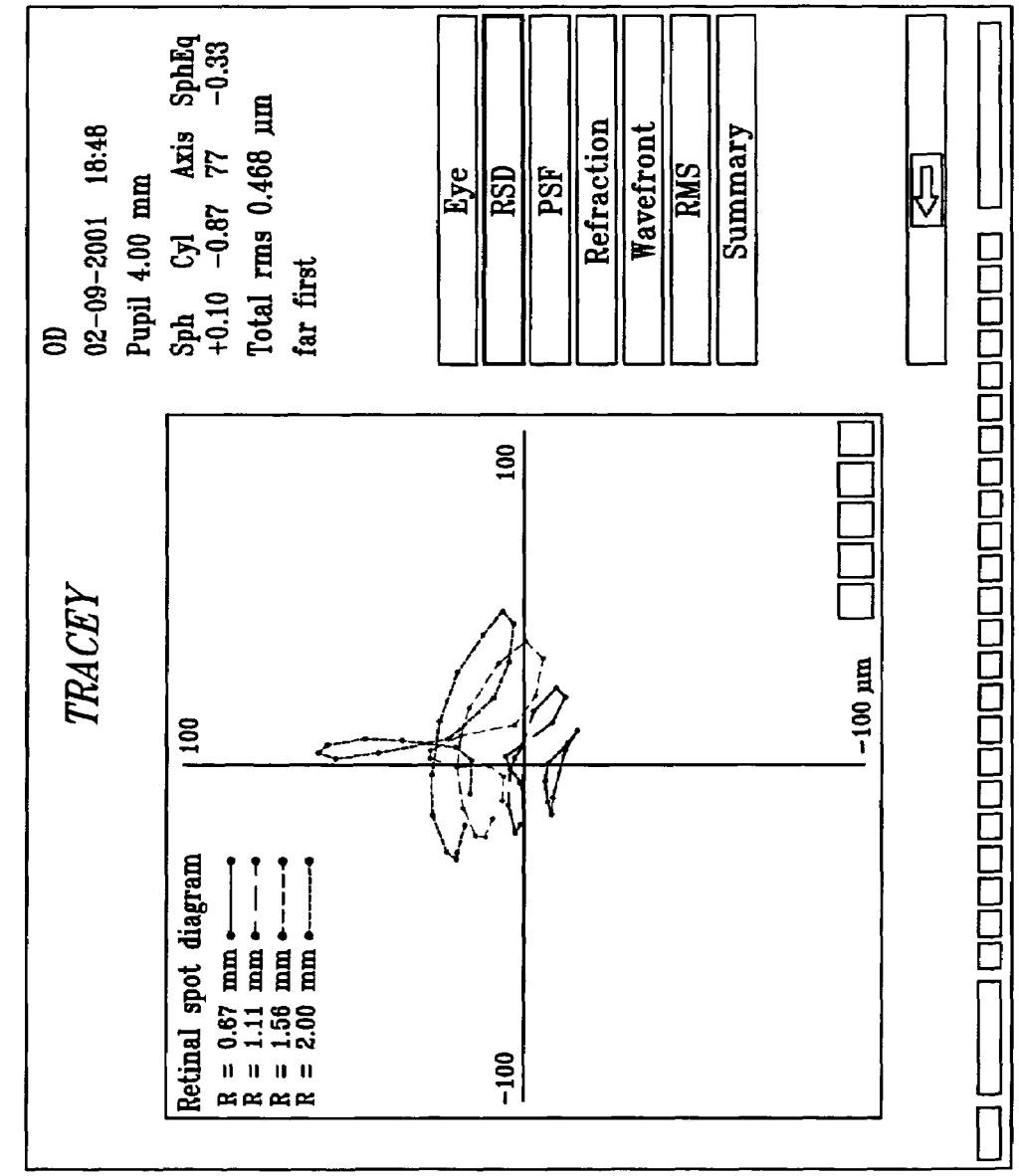
FIG. 23 is a retinal spot diagram of the normal eye at the +0.10 proposed sphero-cylindrical correction showing color coded spots to permit correlation between input beams and the retinal spots.

FIG. 23 is a retinal spot diagram of the normal eye at the +0.10 proposed sphero-cylindrical correction showing color coded spots to permit correlation between input beams and the retinal spots. The spots correlate directly to the beam of light that created the spot and can therefore be traced from the entry location on the pupil as indicated in FIG. 21 above and to the illuminated spot on the retina. By mathematically applying different spherical diopter correction to each beam and spot the retinal spot diagram (i.e. the diagram of spots place on a grid representing the retina with the center of fixation located at the center of the grid) can be effectively moved toward the cornea or away from the cornea. Another way of looking at this is that the pattern of the rays is as they will appear on the retina of an eye that is either longer or shorter. The change in pattern is demonstrated in the series of retinal spot diagrams 25 through 37 for the normal eye.

Figure 24:
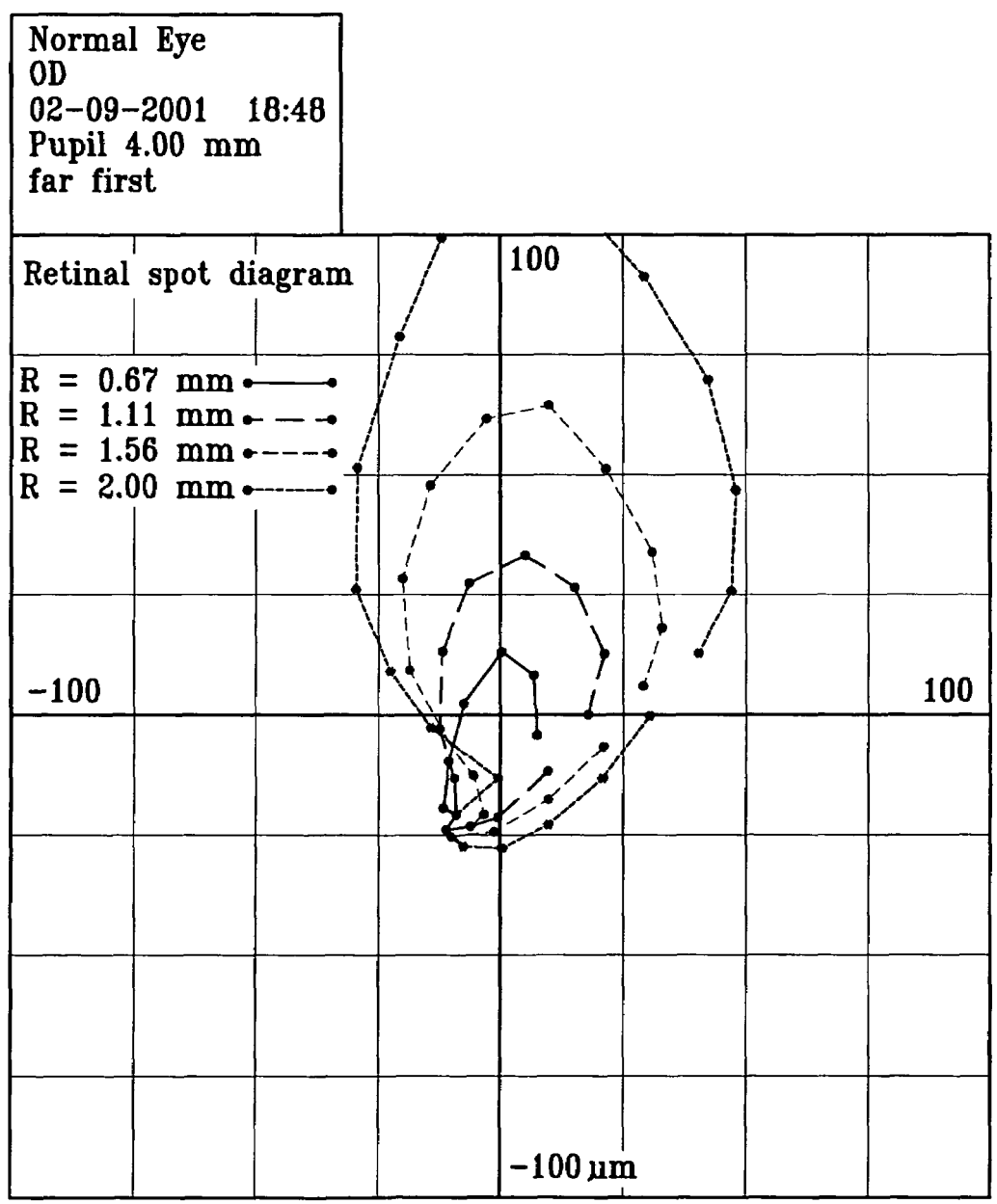
FIG. 24 is a retinal spot diagram of the normal eye at 3×0.5 diopter spherical steps positive correction from the +0.10 proposed sphero-cylindrical correction.

FIG. 24 is a retinal spot diagram of the normal eye at 3×0.5 diopter spherical steps positive correction from the +0.10 proposed sphero-cylindrical correction.

Figure 25:
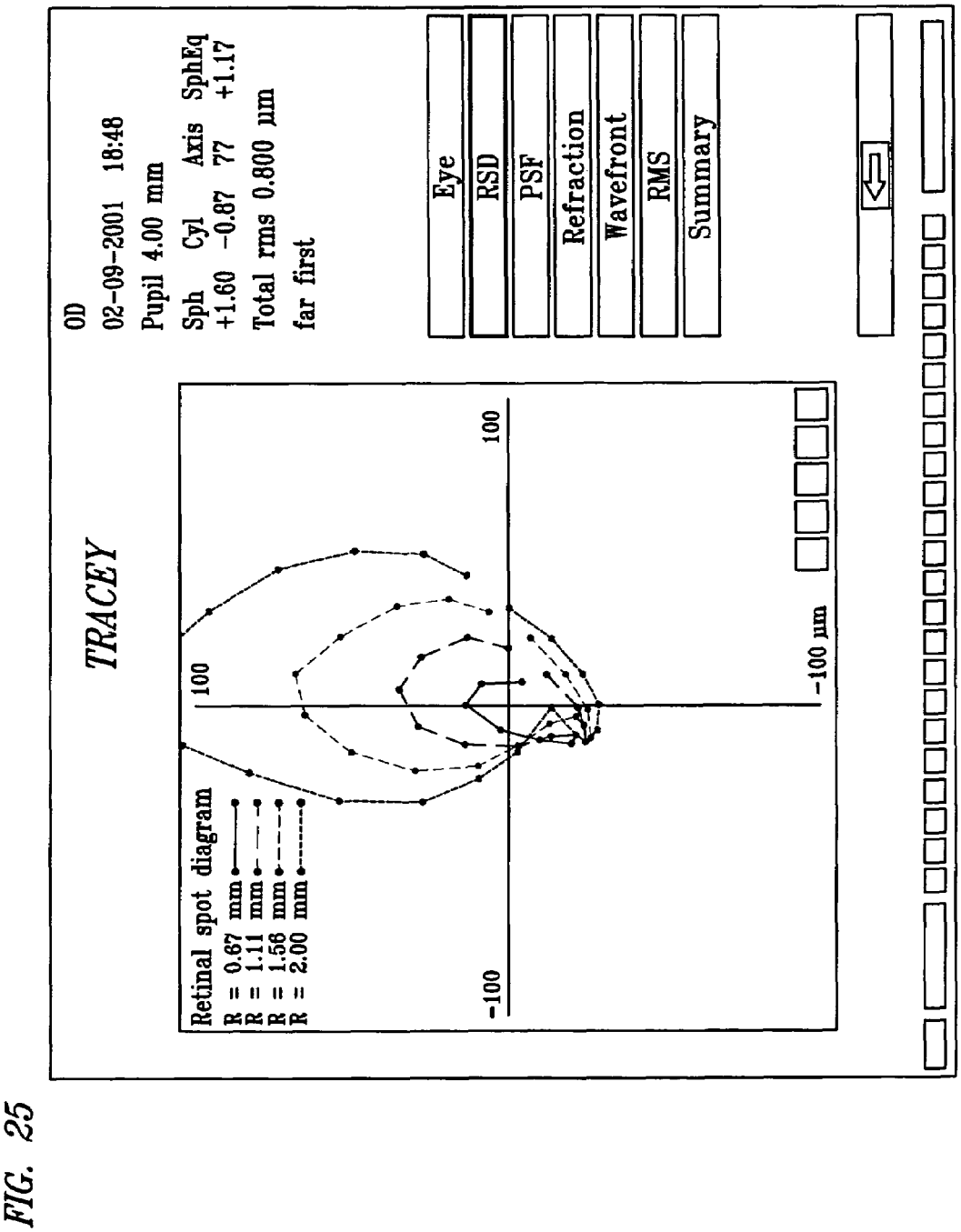
FIG. 25 is a retinal spot diagram of the normal eye at 3×0.5 diopter spherical steps positive correction from the +0.10 proposed sphero-cylindrical correction showing color coded spots to permit correlation between input beams and the retinal spots.

FIG. 25 is a retinal spot diagram of the normal eye at 3×0.5 diopter spherical steps positive correction from the +0.10 proposed sphero-cylindrical correction showing color coded spots to permit correlation between input beams and the retinal spots.

Figure 26:
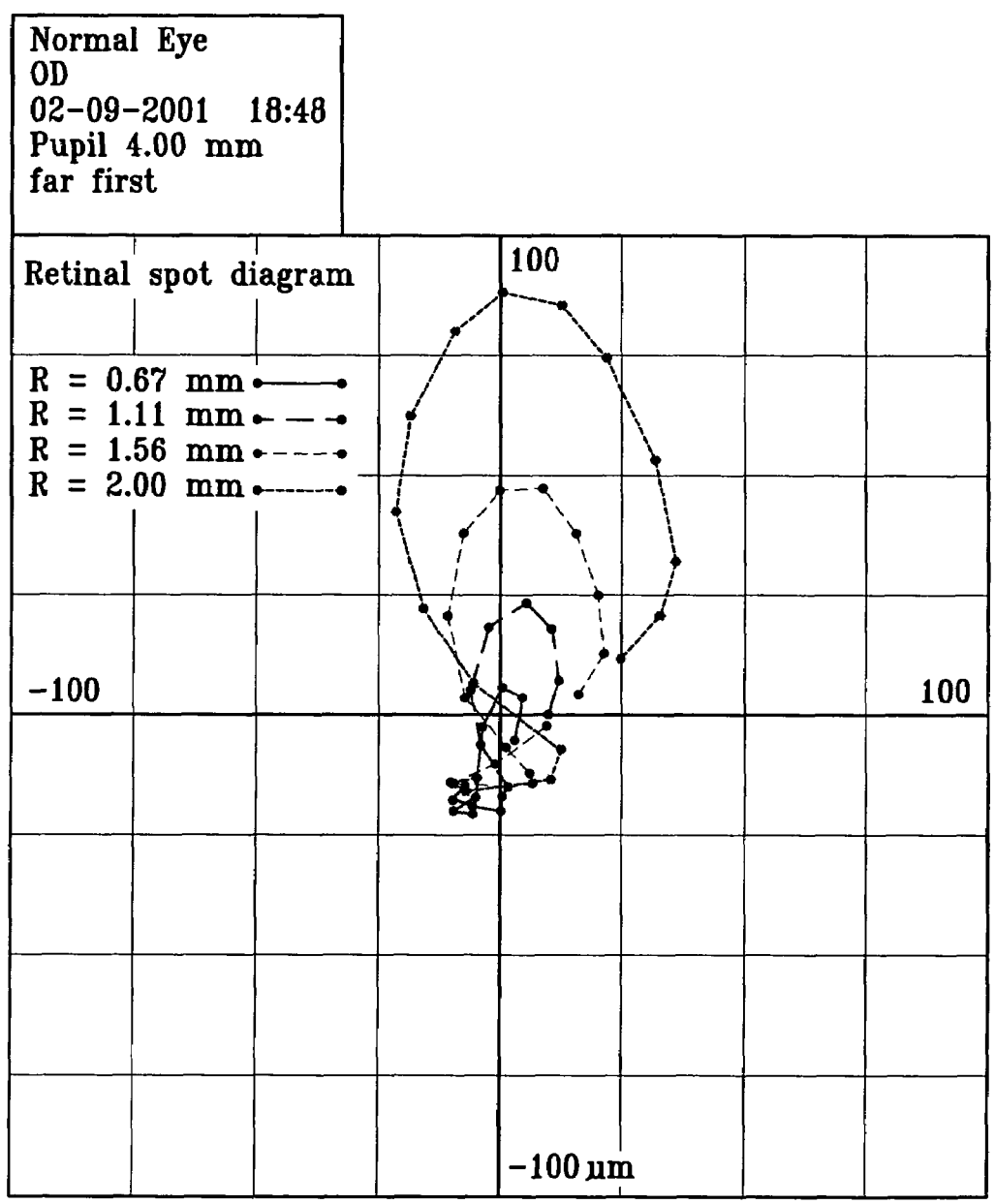
FIG. 26 is a retinal spot diagram of the normal eye at 2×0.5 diopter spherical steps positive correction from the +0.10 proposed sphero-cylindrical correction.

FIG. 26 is a retinal spot diagram of the normal eye at 2×0.5 diopter spherical steps positive correction from the +0.10 proposed sphero-cylindrical correction.

Figure 27:
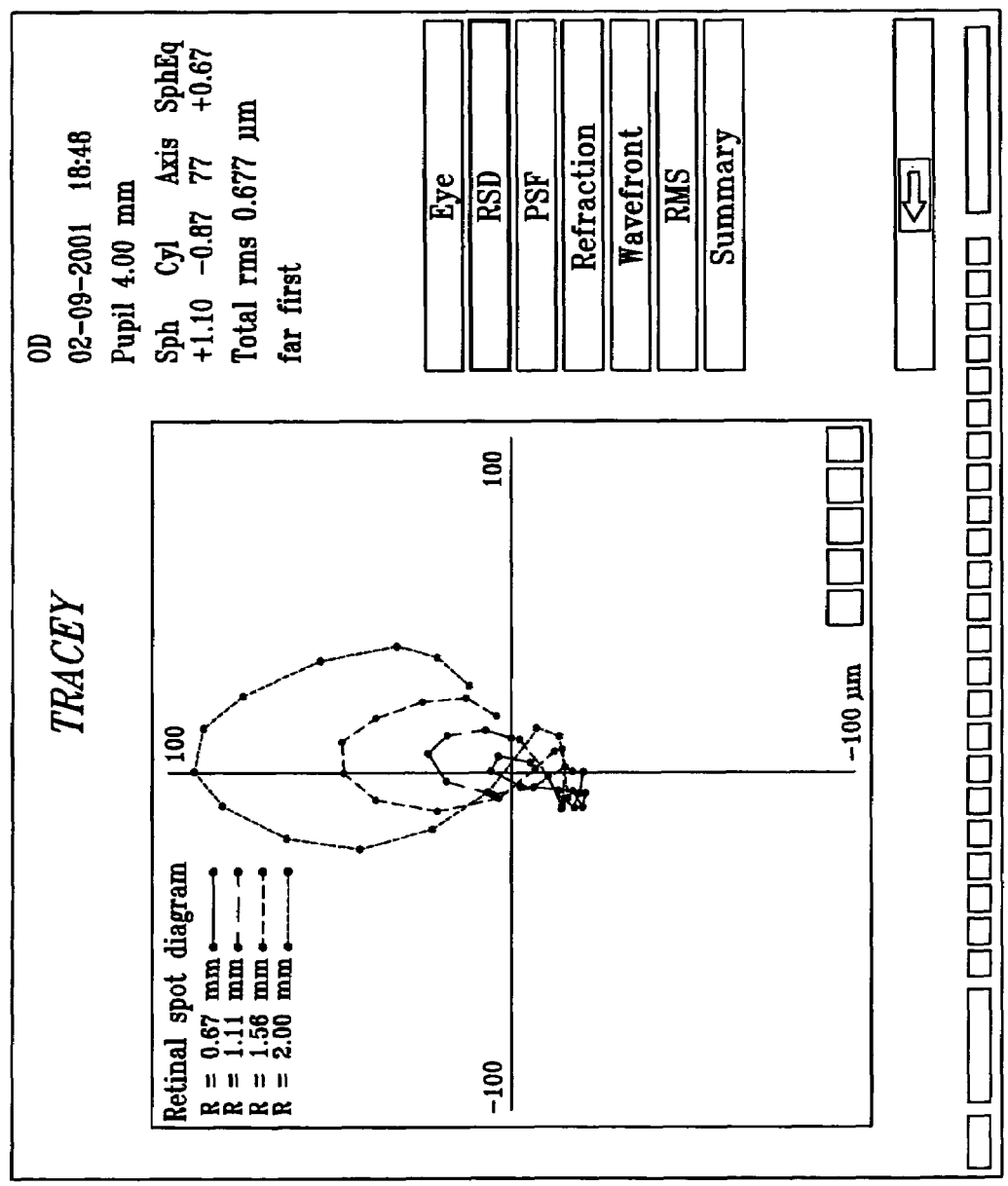
FIG. 27 is a retinal spot diagram of the normal eye at 2×0.5 diopter spherical steps positive correction from the +0.10 proposed sphero-cylindrical correction showing color coded spots to permit correlation between input beams and the retinal spots.

FIG. 27 is a retinal spot diagram of the normal eye at 2×0.5 diopter spherical steps positive correction from the +0.10 proposed sphero-cylindrical correction showing color coded spots to permit correlation between input beams and the retinal spots.

Figure 28:
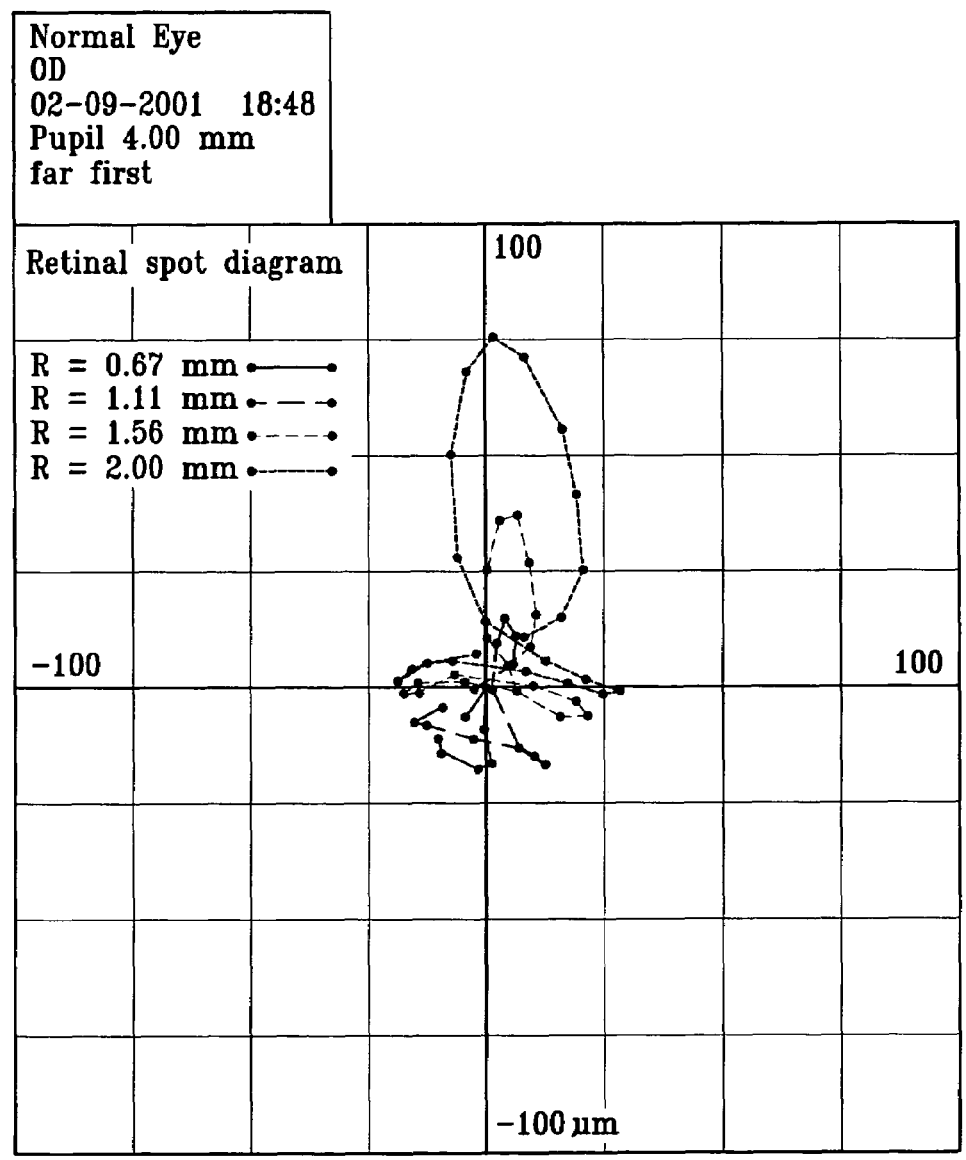
FIG. 28 is a retinal spot diagram of the normal eye at 1×0.5 diopter spherical steps positive correction from the +0.10 proposed sphero-cylindrical correction.

FIG. 28 is a retinal spot diagram of the normal eye at 1×0.5 diopter spherical steps positive correction from the +0.10 proposed sphero-cylindrical correction.

Figure 29:
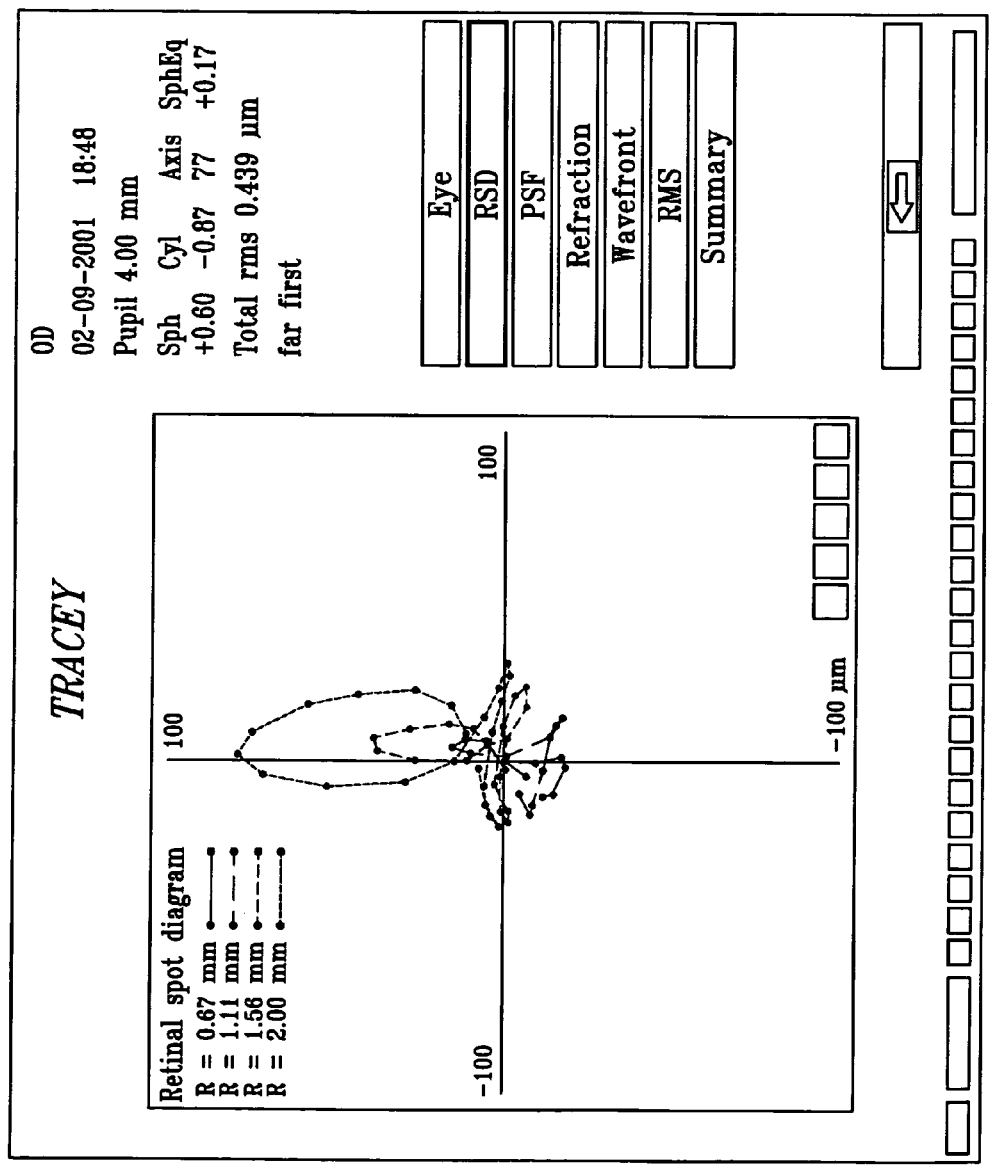
FIG. 29 is a retinal spot diagram of the normal eye at 1×0.5 diopter spherical steps positive correction from the +0.10 proposed sphero-cylindrical correction showing color coded spots to permit correlation between input beams and the retinal spots.

FIG. 29 is a retinal spot diagram of the normal eye at 1×0.5 diopter spherical steps positive correction from the +0.10 proposed sphero-cylindrical correction showing color coded spots to permit correlation between input beams and the retinal spots.

Figure 30:
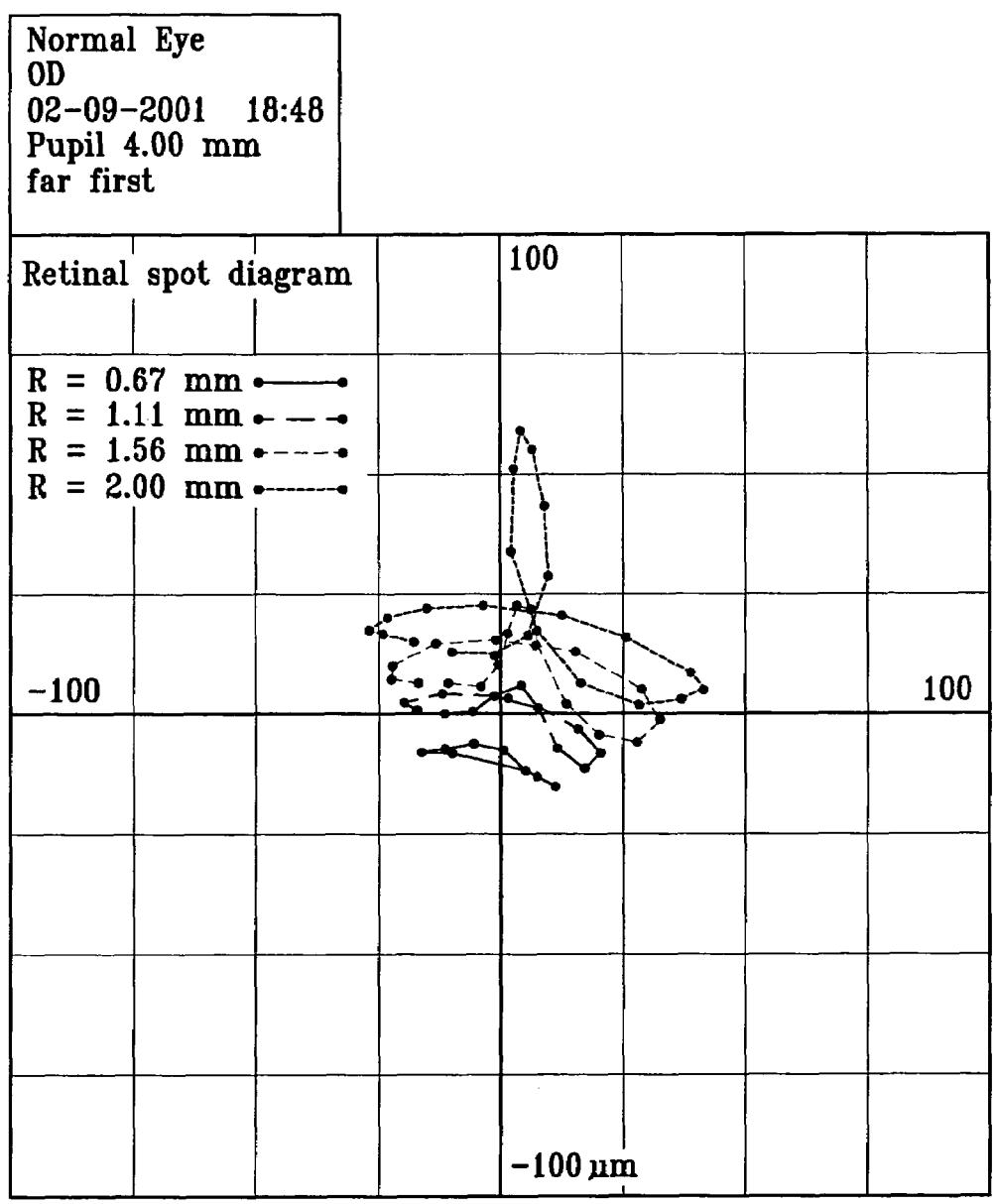
FIG. 30 is a retinal spot diagram of the normal eye at the +0.10 proposed sphero-cylindrical correction.

FIG. 30 is a retinal spot diagram of the normal eye at the +0.10 proposed sphero-cylindrical correction.

Figure 31:
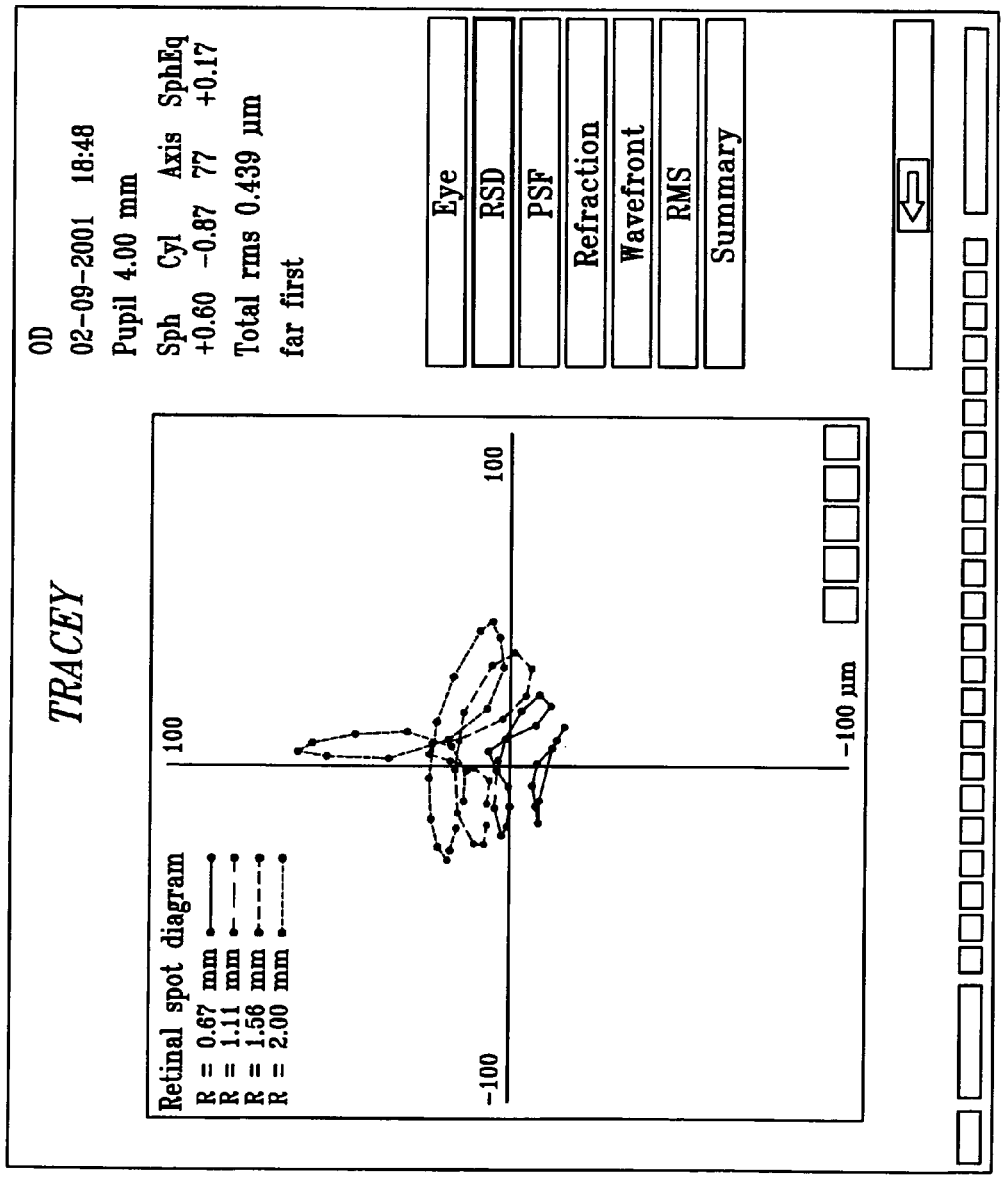
FIG. 31 is a retinal spot diagram of the normal eye at 4×0.5 diopter spherical steps positive correction from the +0.10 proposed sphero-cylindrical correction showing color coded spots to permit correlation between input beams and the retinal spots.

FIG. 31 is a retinal spot diagram of the normal eye at 4×0.5 diopter spherical steps positive correction from the +0.10 proposed sphero-cylindrical correction showing color coded spots to permit correlation between input beams and the retinal spots.

Figure 32:
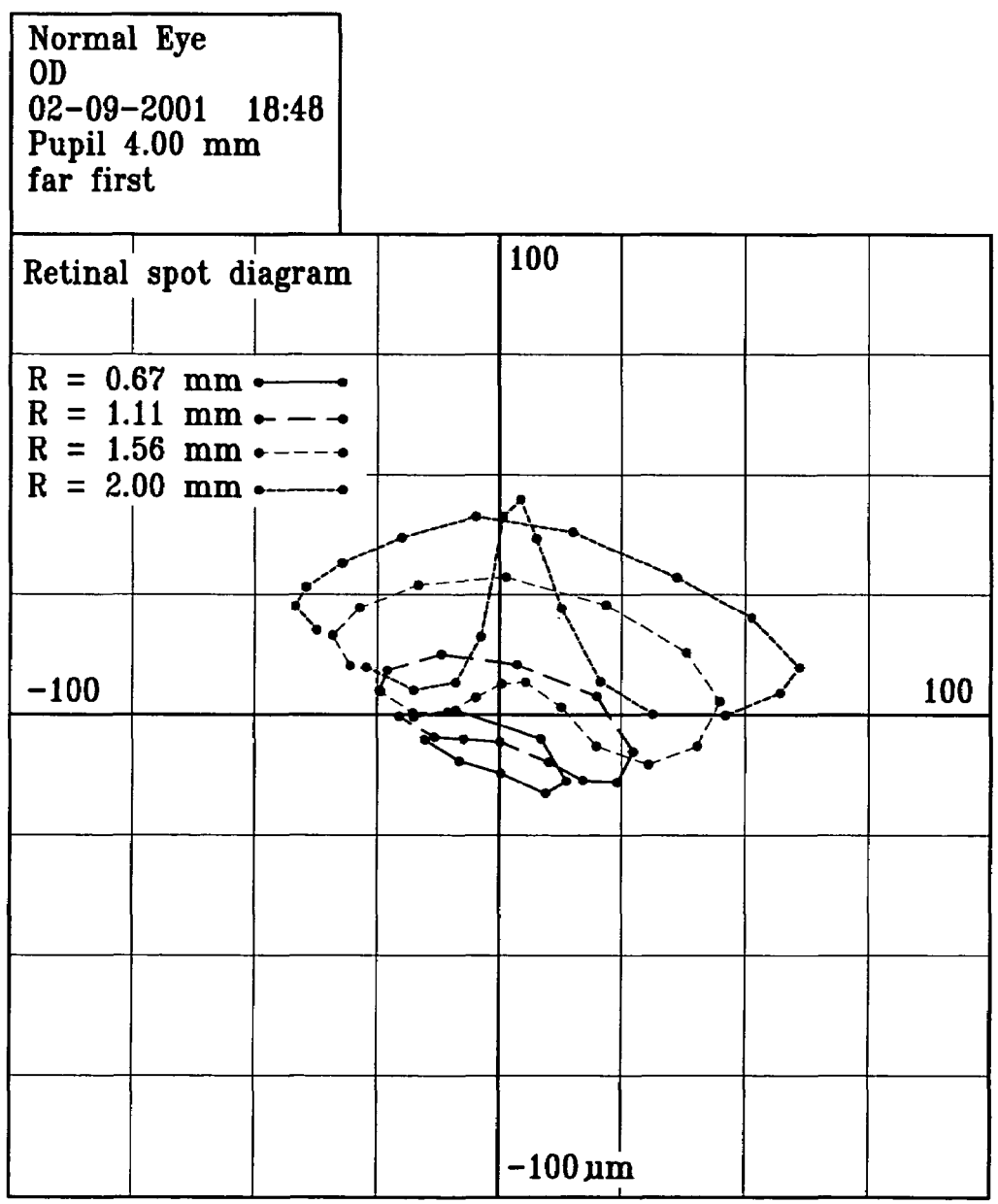
FIG. 32 is a retinal spot diagram of the normal eye at 1×0.5 diopter spherical steps negative correction from the +0.10 proposed sphero-cylindrical correction.

FIG. 32 is a retinal spot diagram of the normal eye at 1×0.5 diopter spherical steps negative correction from the +0.10 proposed sphero-cylindrical correction.

Figure 33:
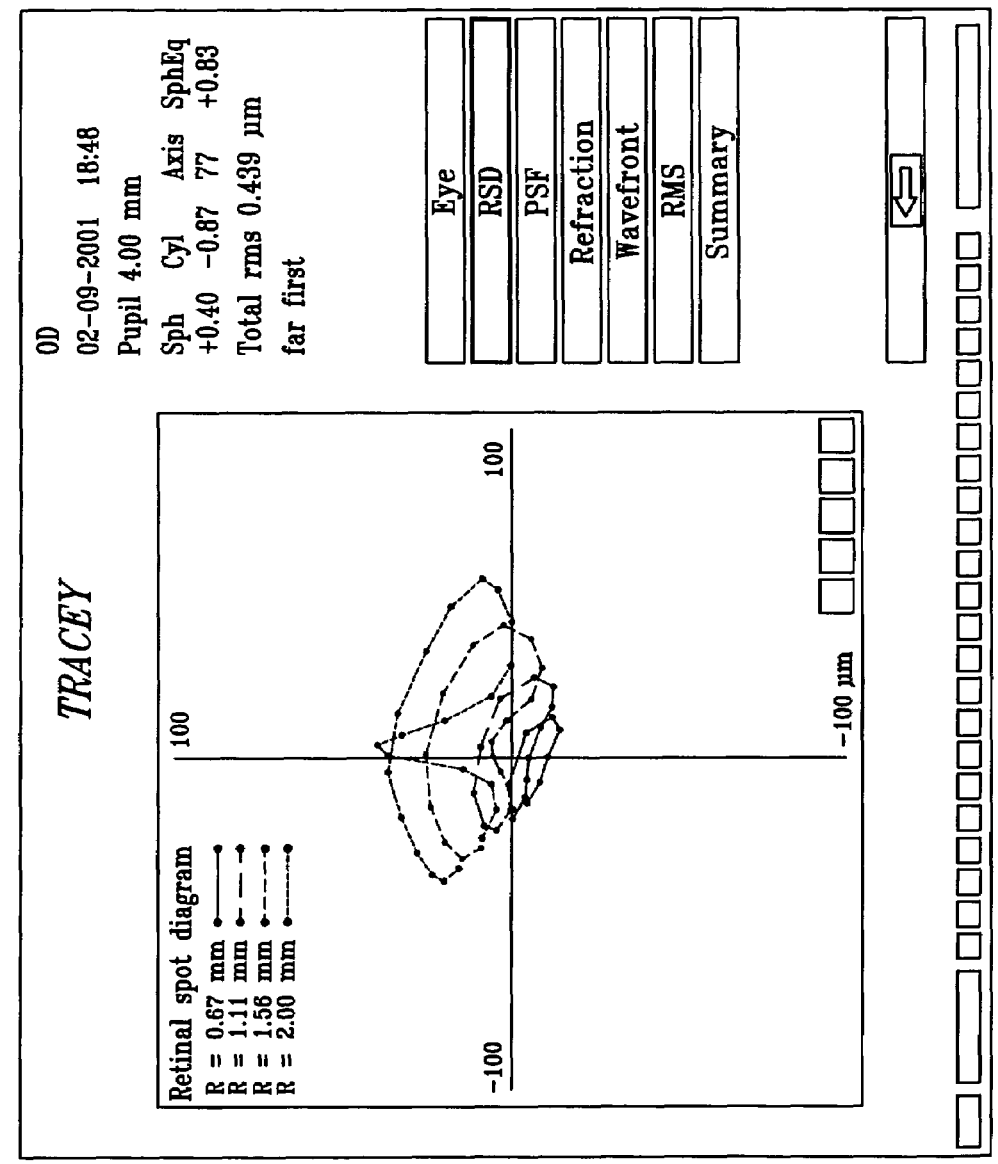
FIG. 33 is a retinal spot diagram of the normal eye at 1×0.5 diopter spherical steps negative correction from the +0.10 proposed sphero-cylindrical correction showing color coded spots to permit correlation between input beams and the retinal spots.

FIG. 33 is a retinal spot diagram of the normal eye at 1×0.5 diopter spherical steps negative correction from the +0.10 proposed sphero-cylindrical correction showing color coded spots to permit correlation between input beams and the retinal spots.

Figure 34:
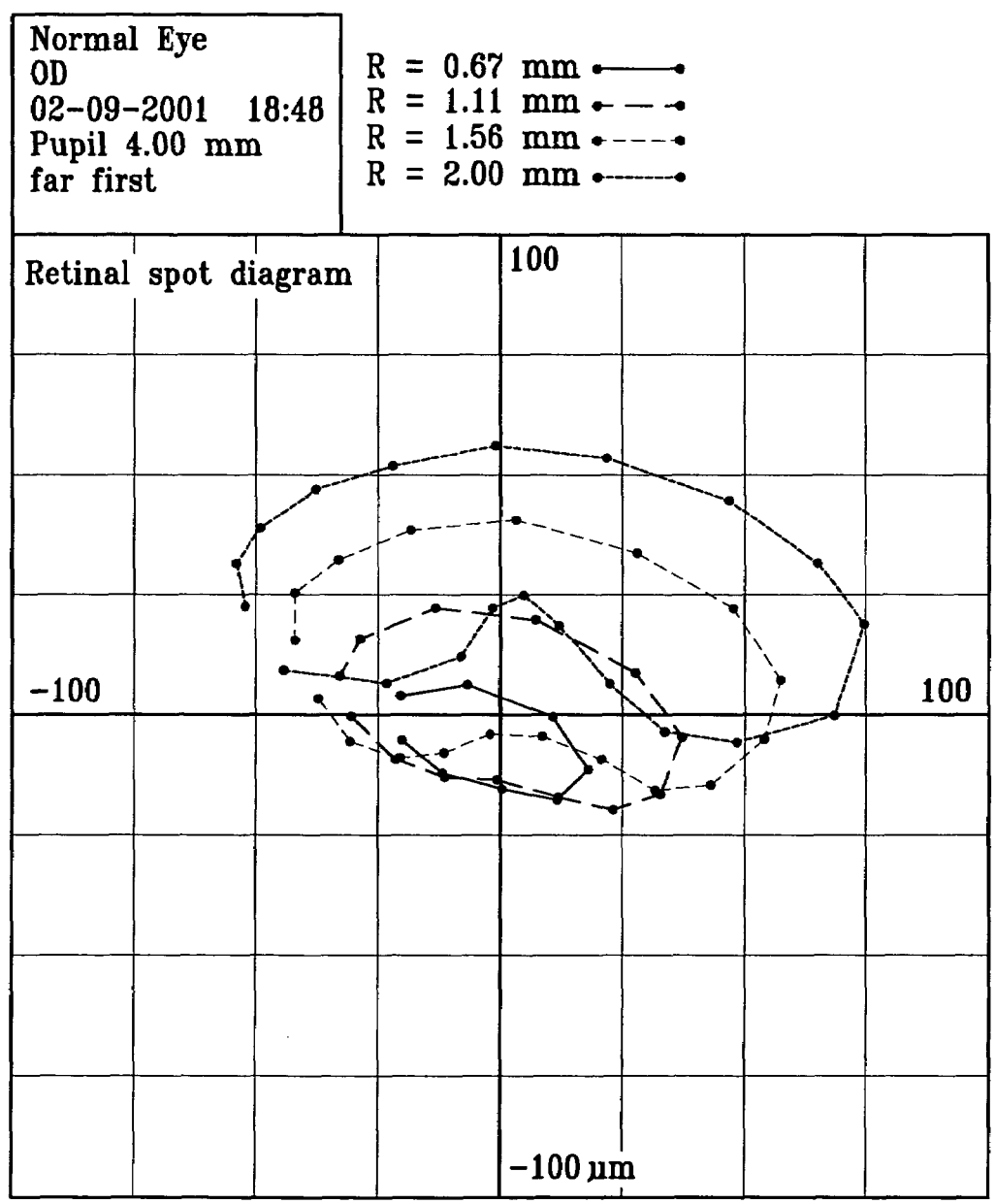
FIG. 34 is a retinal spot diagram of the normal eye at 2×0.5 diopter spherical steps negative correction from the +0.10 proposed sphero-cylindrical correction.

FIG. 34 is a retinal spot diagram of the normal eye at 2×0.5 diopter spherical steps negative correction from the +0.10 proposed sphero-cylindrical correction.

Figure 35:
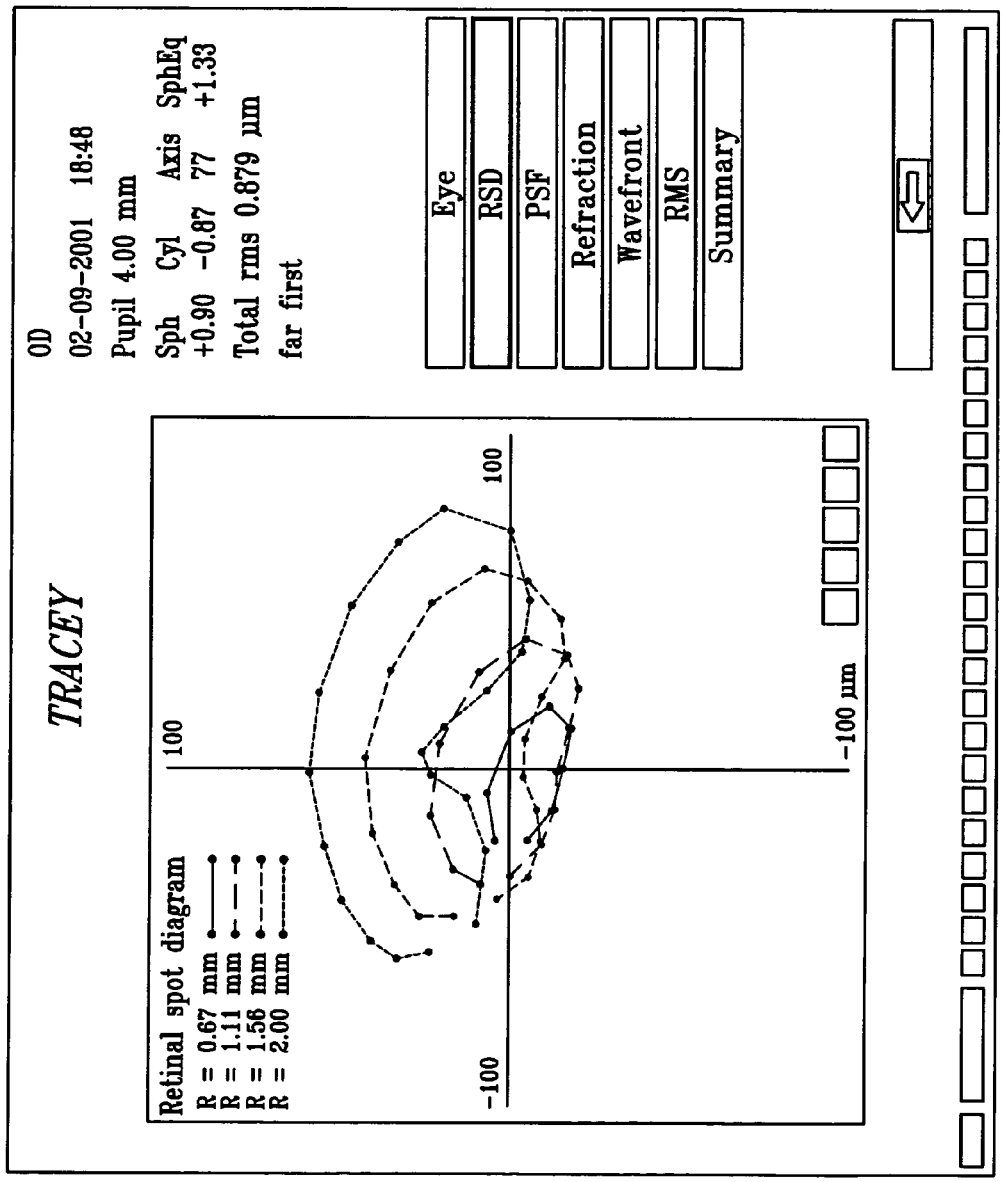
FIG. 35 is a retinal spot diagram of the normal eye at 2×0.5 diopter spherical steps negative correction from the +0.10 proposed sphero-cylindrical correction showing color coded spots to permit correlation between input beams and the retinal spots.

FIG. 35 is a retinal spot diagram of the normal eye at 2×0.5 diopter spherical steps negative correction from the +0.10 proposed sphero-cylindrical correction showing color coded spots to permit correlation between input beams and the retinal spots.

Figure 36:
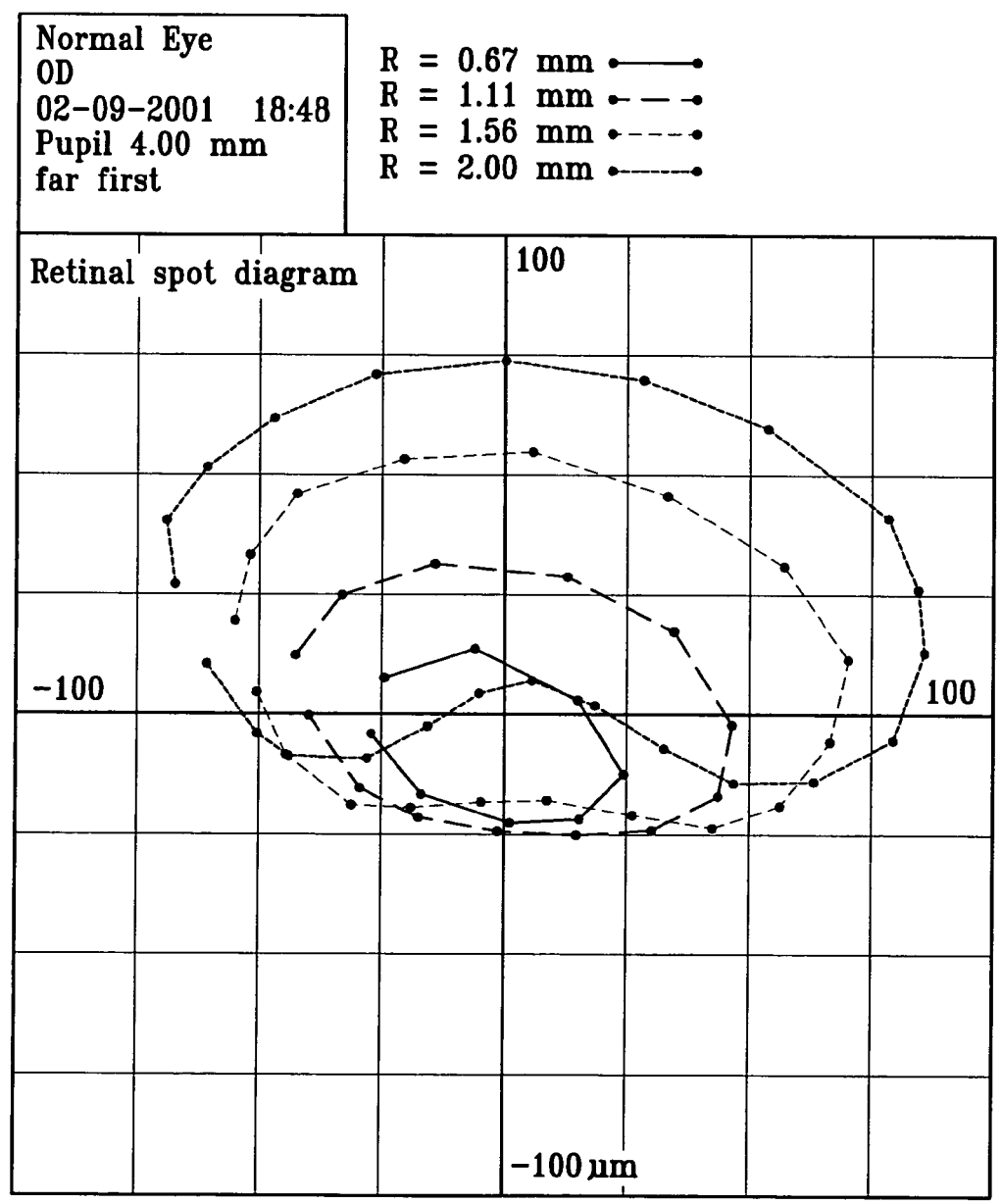
FIG. 36 is a retinal spot diagram of the normal eye at 3×0.5 diopter spherical steps negative correction from the +0.10 proposed sphero-cylindrical correction.

FIG. 36 is a retinal spot diagram of the normal eye at 3×0.5 diopter spherical steps negative correction from the +0.10 proposed sphero-cylindrical correction.

Figure 37:
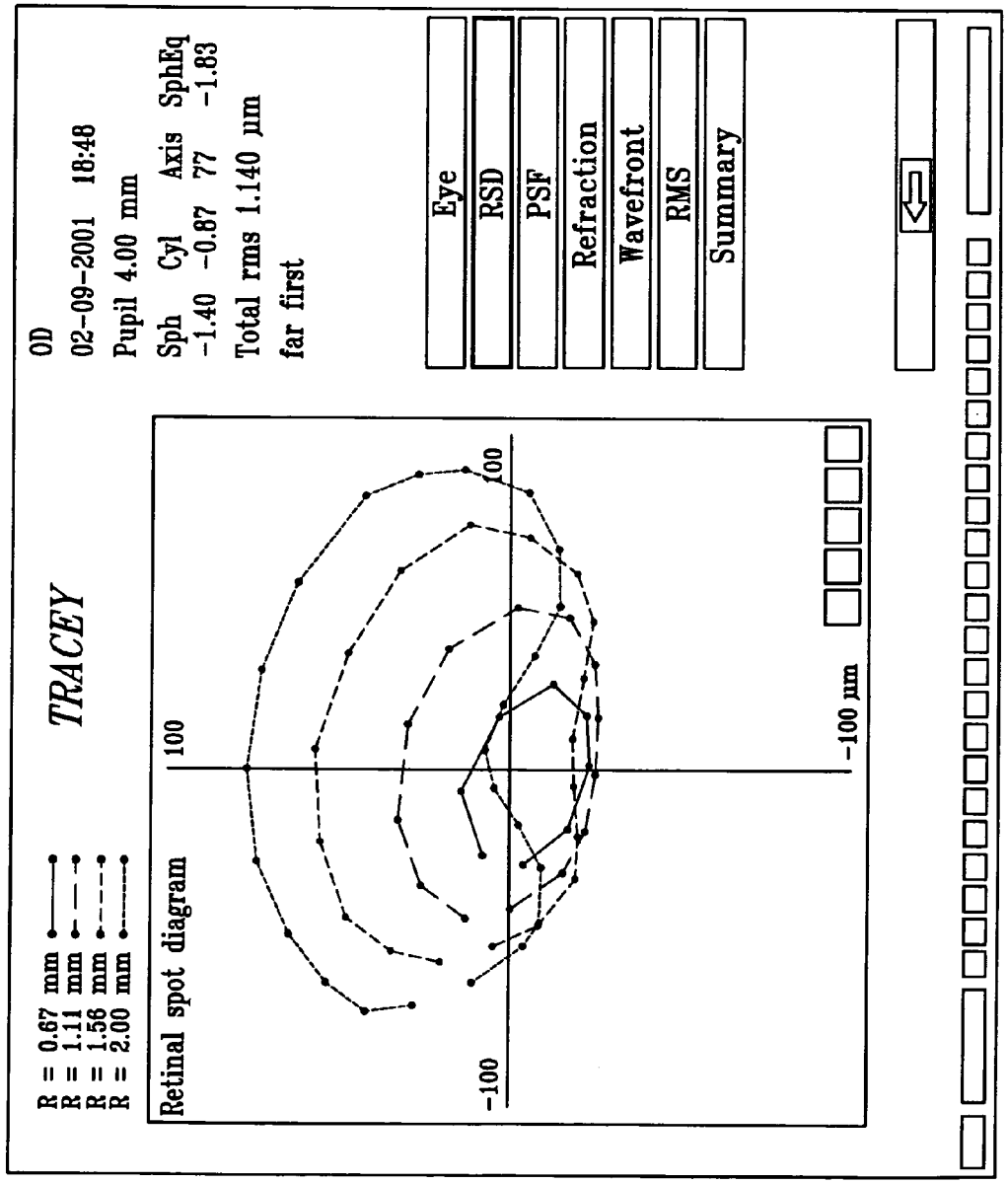
FIG. 37 is a retinal spot diagram of the normal eye at 3×0.5 diopter spherical steps negative correction from the +0.10 proposed sphero-cylindrical correction showing color coded spots to permit correlation between input beams and the retinal spots.

FIG. 37 is a retinal spot diagram of the normal eye at 3×0.5 diopter spherical steps negative correction from the +0.10 proposed sphero-cylindrical correction showing color coded spots to permit correlation between input beams and the retinal spots.

Figure 38:
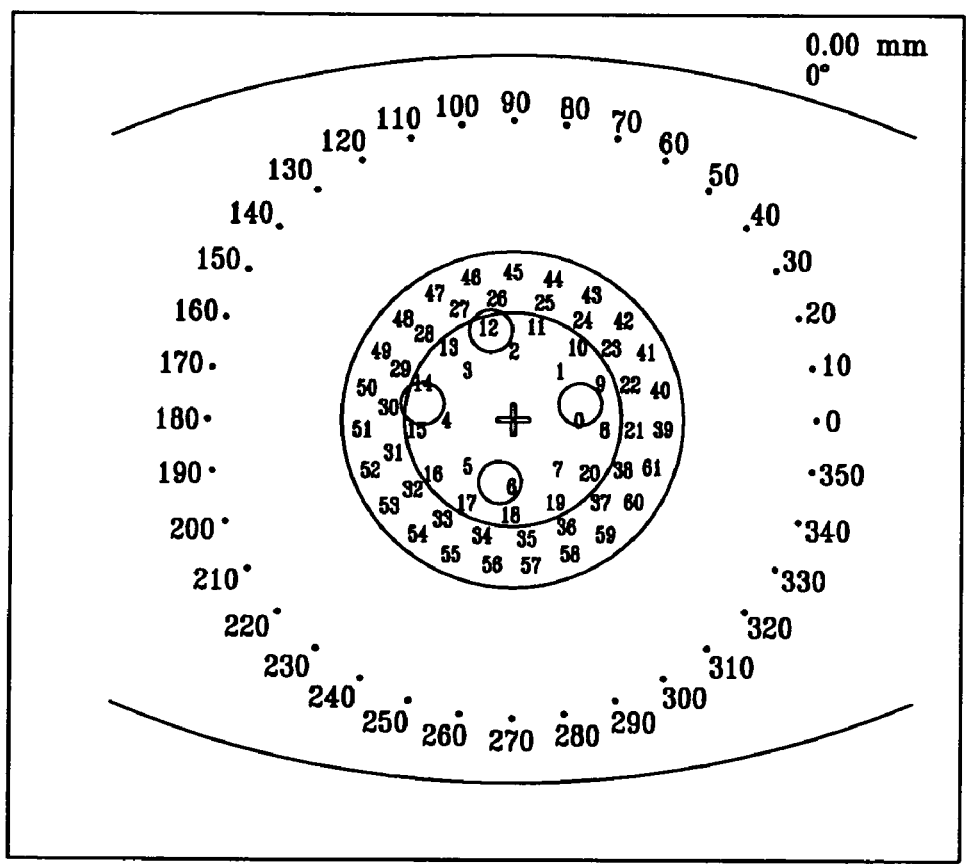
FIG. 38 is the pupil of a poor eye with beam points of entry used to produce retinal spot diagrams with ray tracing technology.

FIG. 38 is the pupil of a poor eye with beam points of entry used to produce retinal spot diagrams with ray tracing technology.

Figure 39:
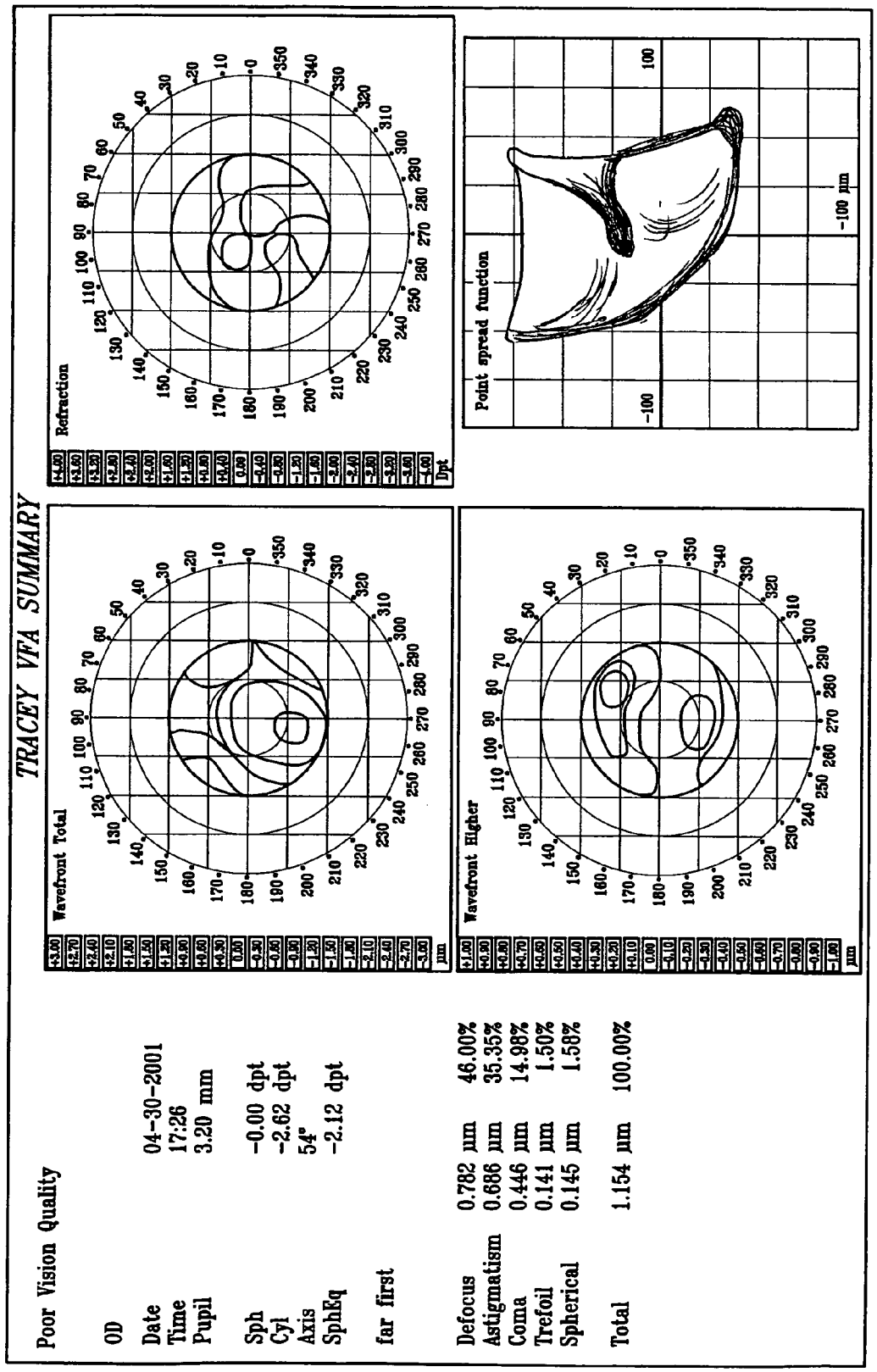
FIG. 39 shows diagrams of wavefront refraction, wavefront total, wavefront higher order distortions, and point spread function.

FIG. 39 shows diagrams of wavefront refraction, wavefront total, wavefront higher order distortions, and point spread function.

Figure 40:
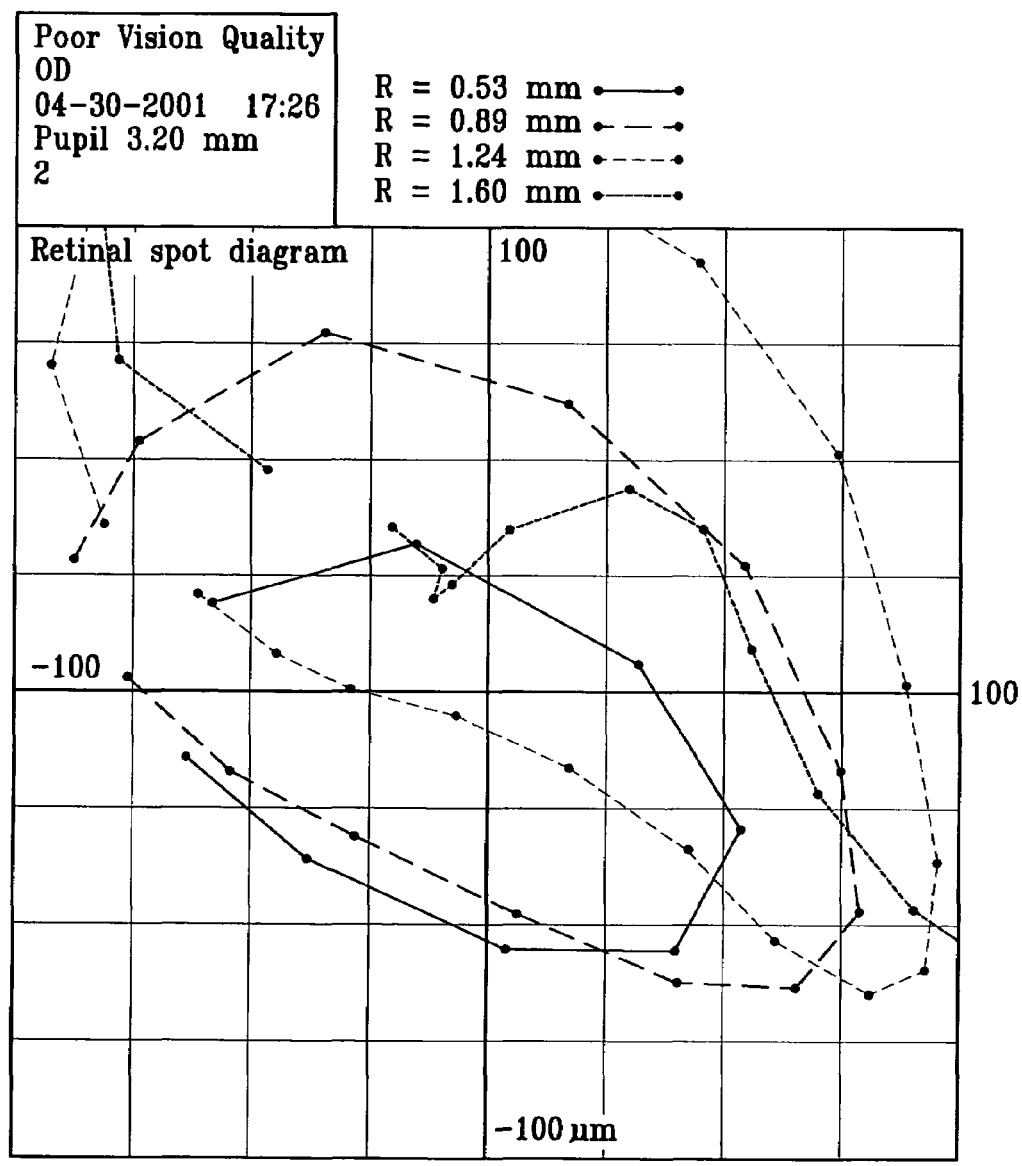
FIG. 40 is a retinal spot diagram of the poor eye at 4×0.5 diopter spherical steps negative correction from the −0.80 proposed sphero-cylindrical correction.

FIG. 40 is a retinal spot diagram of the poor eye at 4×0.5 diopter spherical steps negative correction from the −0.80 proposed sphero-cylindrical correction.

Figure 41:
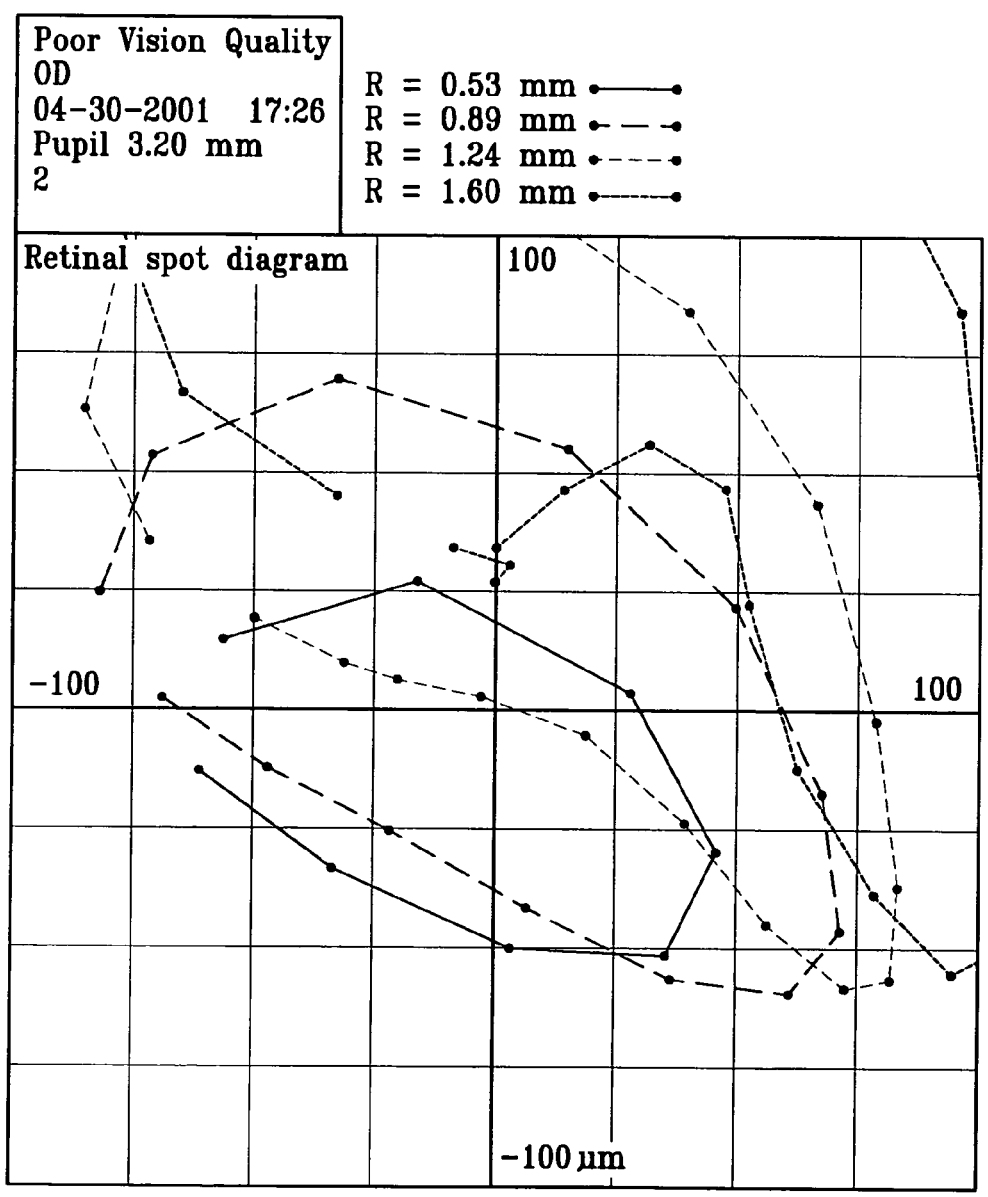
FIG. 41 is a retinal spot diagram of the poor eye at 3×0.5 diopter spherical steps negative correction from the −0.80 proposed sphero-cylindrical correction.

FIG. 41 is a retinal spot diagram of the poor eye at 3×0.5 diopter spherical steps negative correction from the −0.80 proposed sphero-cylindrical correction.

Figure 42:
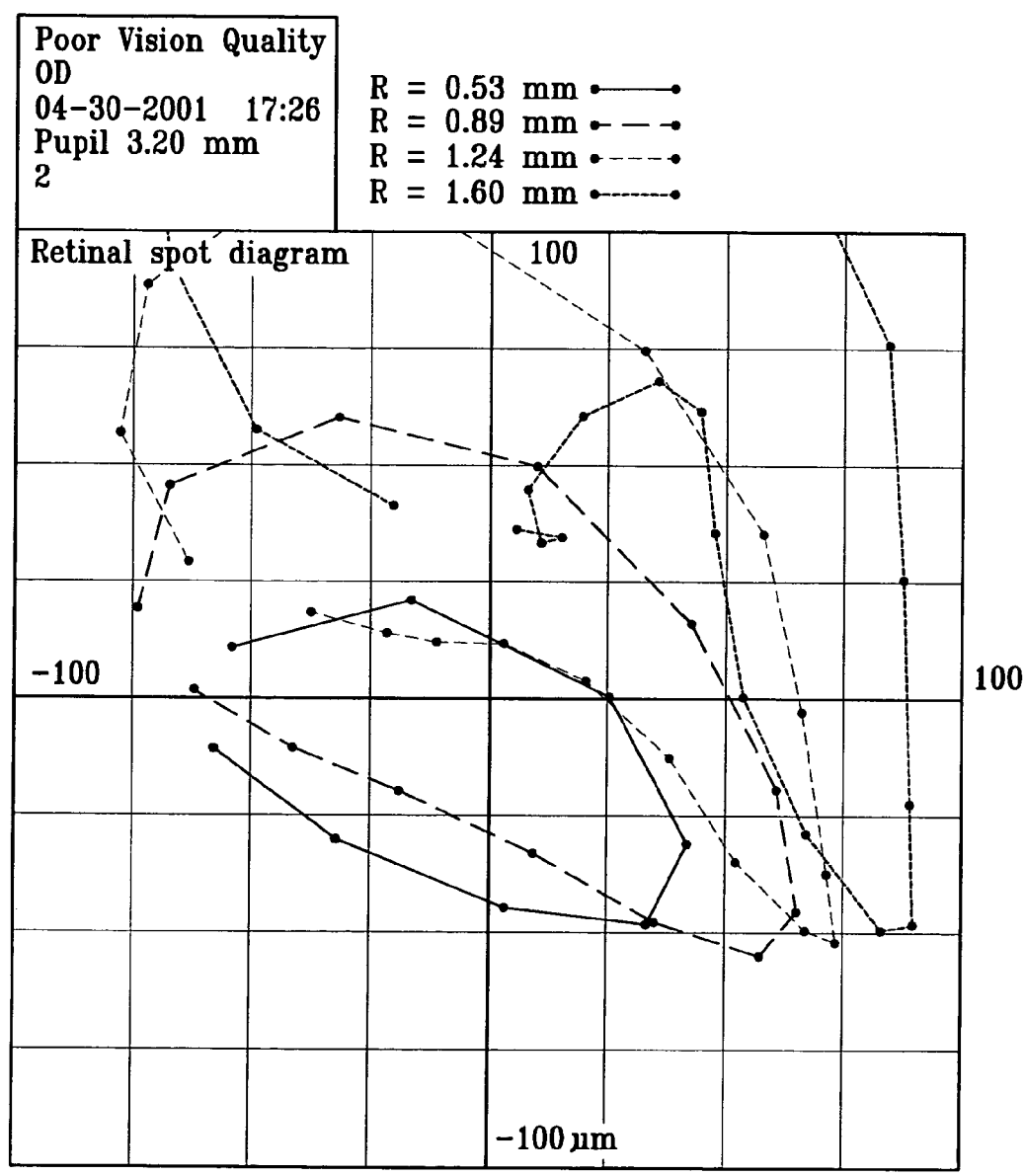
FIG. 42 is a retinal spot diagram of the poor eye at 2×0.5 diopter spherical steps negative correction from the −0.80 proposed sphero-cylindrical correction.

FIG. 42 is a retinal spot diagram of the poor eye at 2×0.5 diopter spherical steps negative correction from the −0.80 proposed sphero-cylindrical correction.

Figure 43:
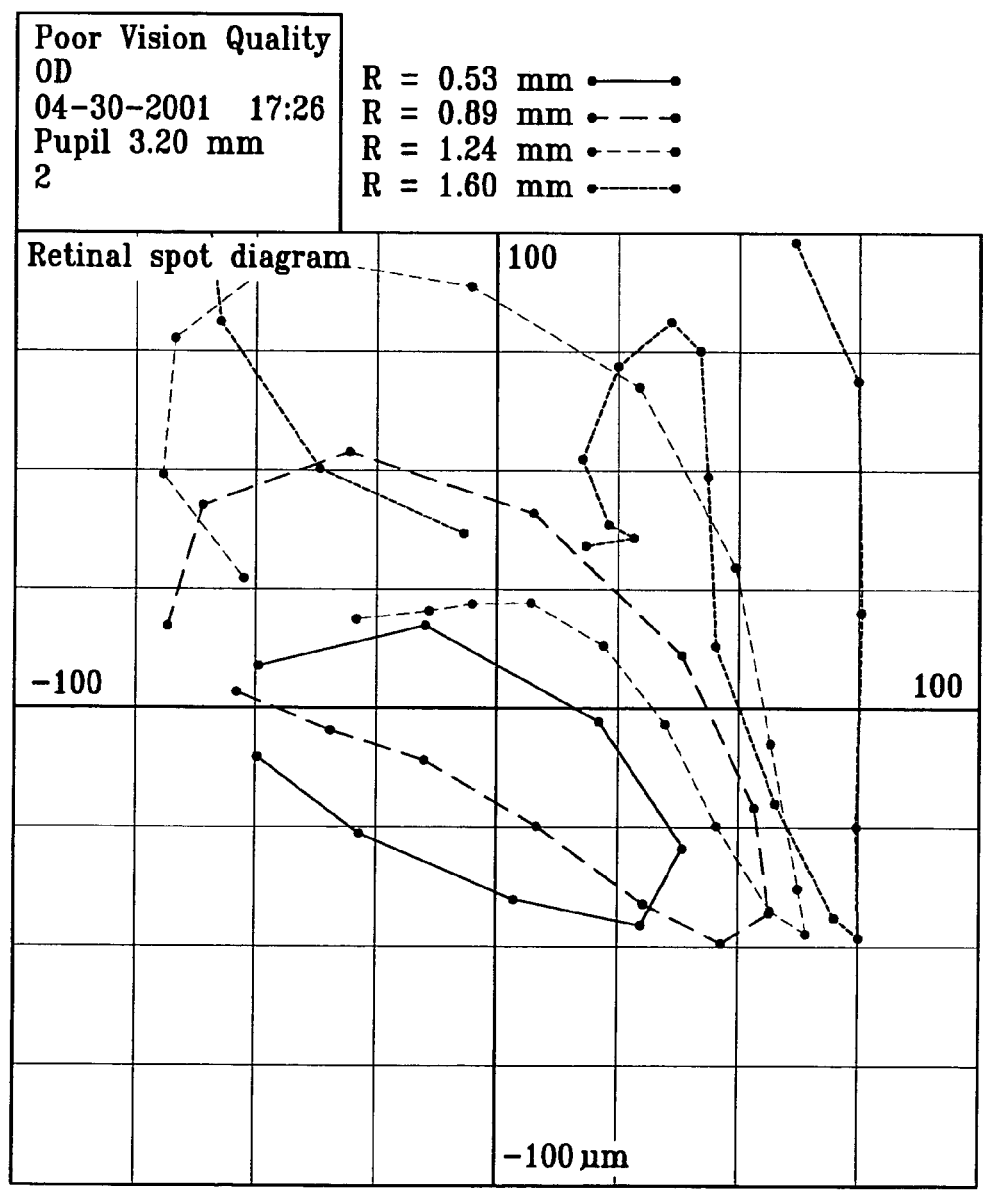
FIG. 43 is a retinal spot diagram of the poor eye at 1×0.5 diopter spherical steps negative correction from the −0.80 proposed sphero-cylindrical correction.

FIG. 43 is a retinal spot diagram of the poor eye at 1×0.5 diopter spherical steps negative correction from the −0.80 proposed sphero-cylindrical correction.

Figure 44:
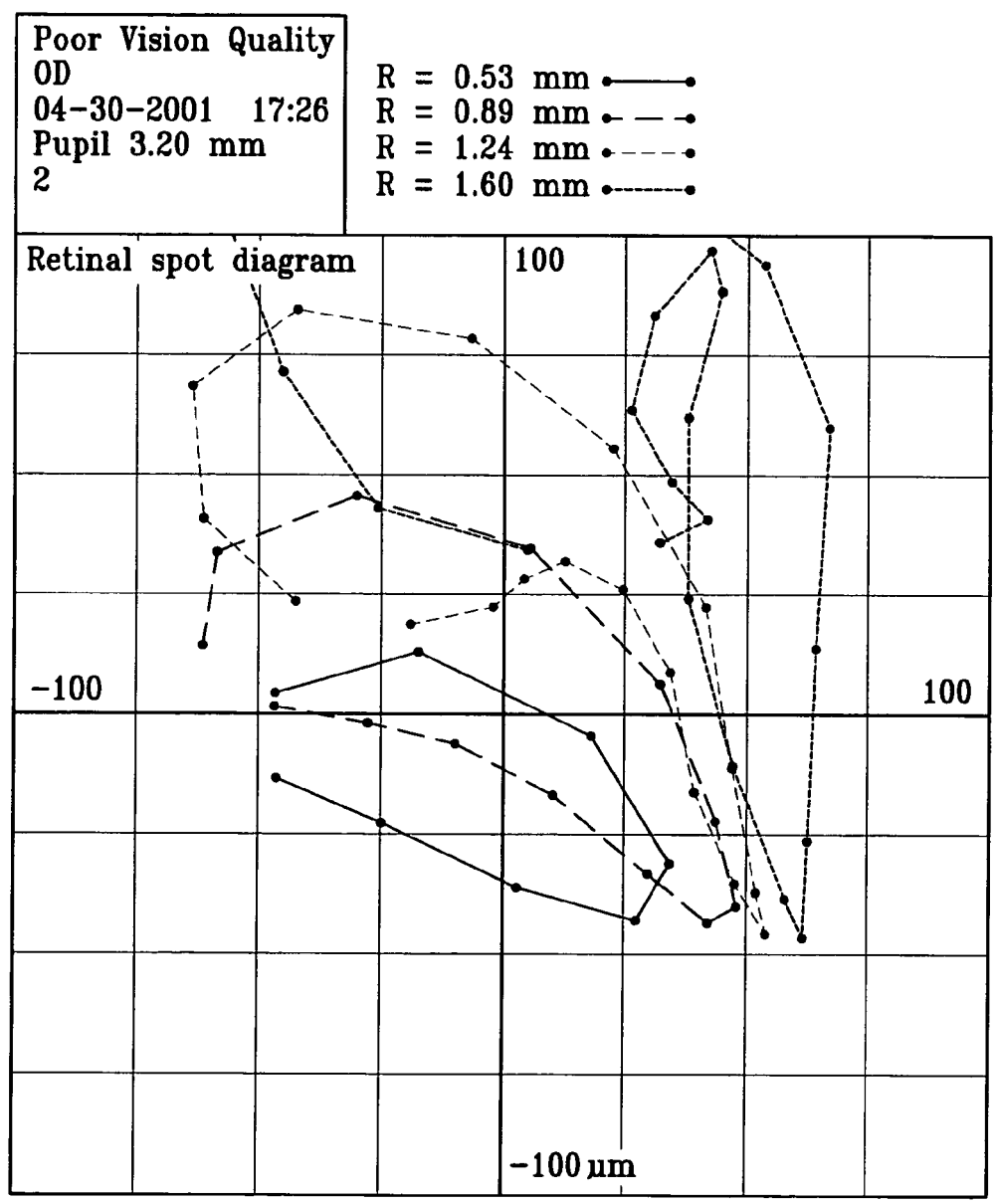
FIG. 44 is a retinal spot diagram of the poor eye at the −0.80 proposed sphero-cylindrical correction.

FIG. 44 is a retinal spot diagram of the poor eye at the −0.80 proposed sphero-cylindrical correction.

Figure 45:
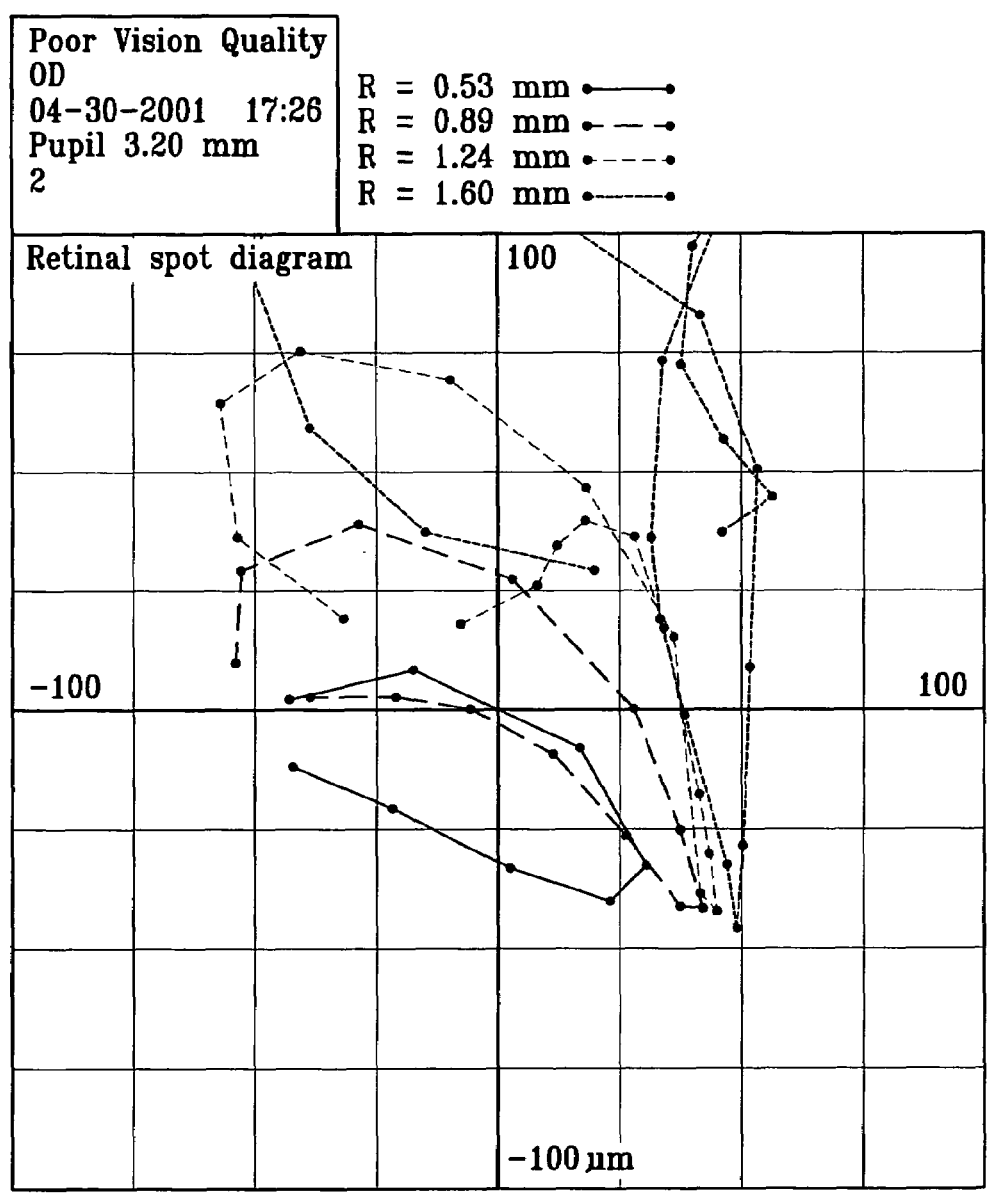
FIG. 45 is a retinal spot diagram of the poor eye at 1×0.5 diopter spherical steps positive correction from the −0.80 proposed sphero-cylindrical correction.

FIG. 45 is a retinal spot diagram of the poor eye at 1×0.5 diopter spherical steps positive correction from the −0.80 proposed sphero-cylindrical correction.

Figure 46:
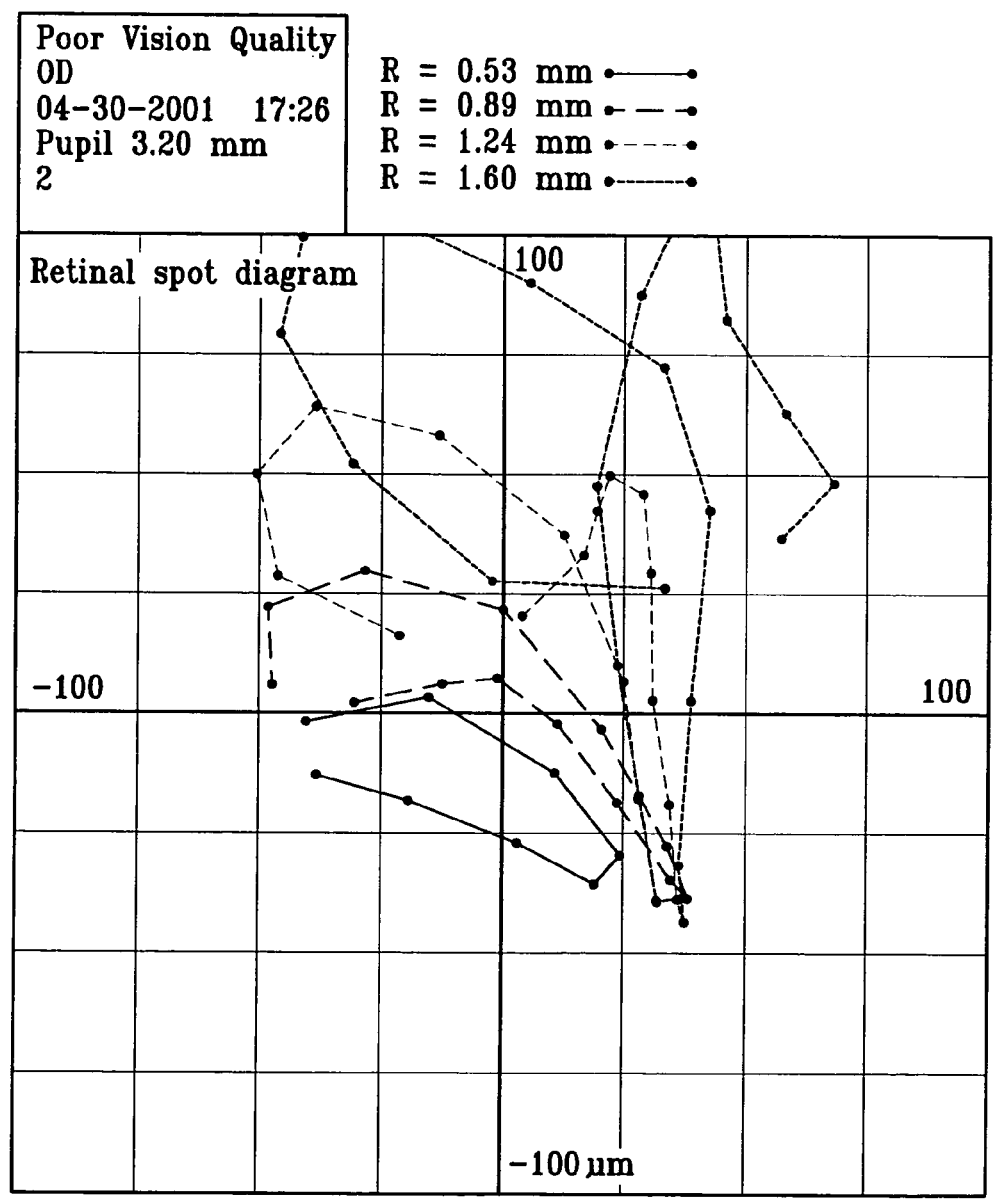
FIG. 46 is a retinal spot diagram of the poor eye at 2×0.5 diopter spherical steps positive correction from the −0.80 proposed sphero-cylindrical correction.

FIG. 46 is a retinal spot diagram of the poor eye at 2×0.5 diopter spherical steps positive correction from the −0.80 proposed sphero-cylindrical correction.

Figure 47:
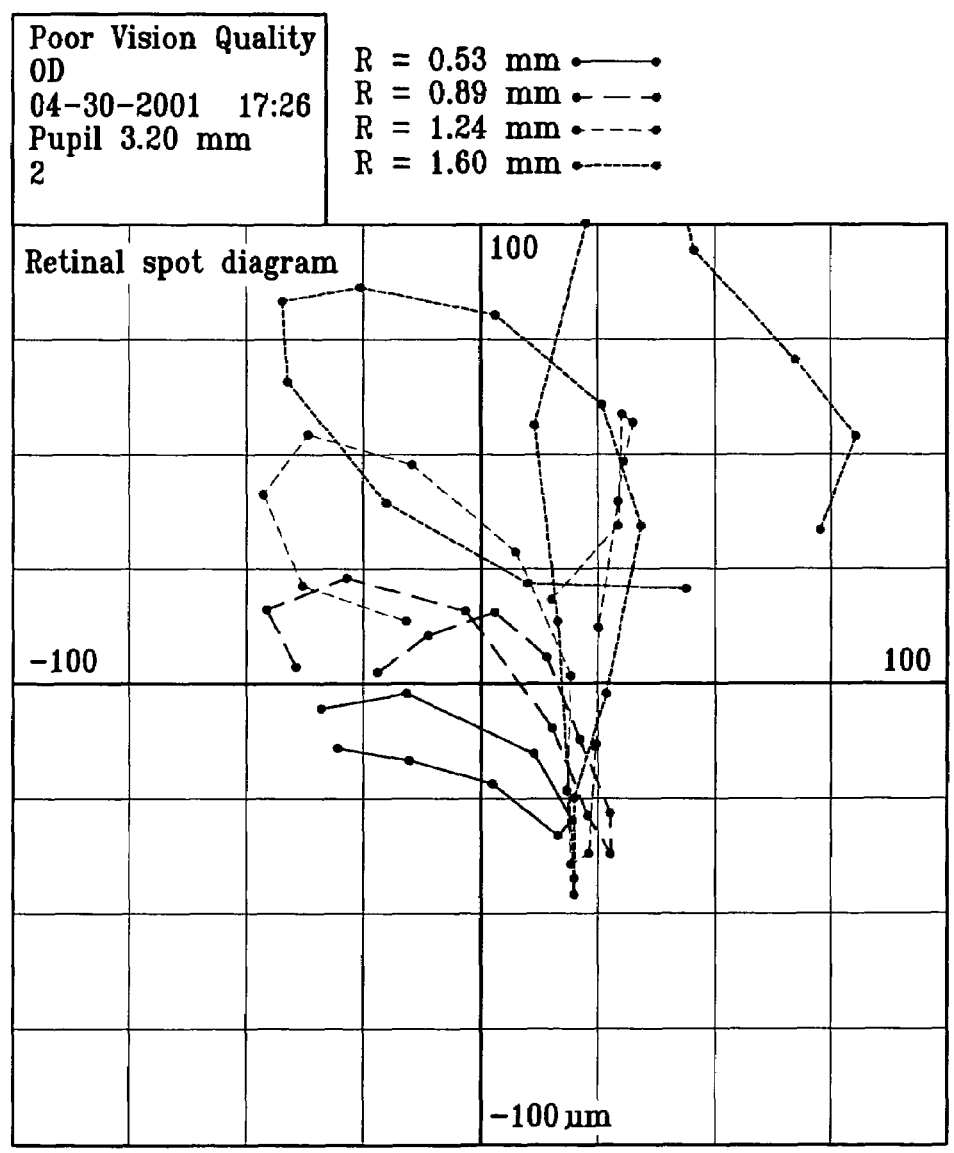
FIG. 47 is a retinal spot diagram of the poor eye at 3×0.5 diopter spherical steps positive correction from the −0.80 proposed sphero-cylindrical correction.

FIG. 47 is a retinal spot diagram of the poor eye at 3×0.5 diopter spherical steps positive correction from the −0.80 proposed sphero-cylindrical correction.

Figure 48:
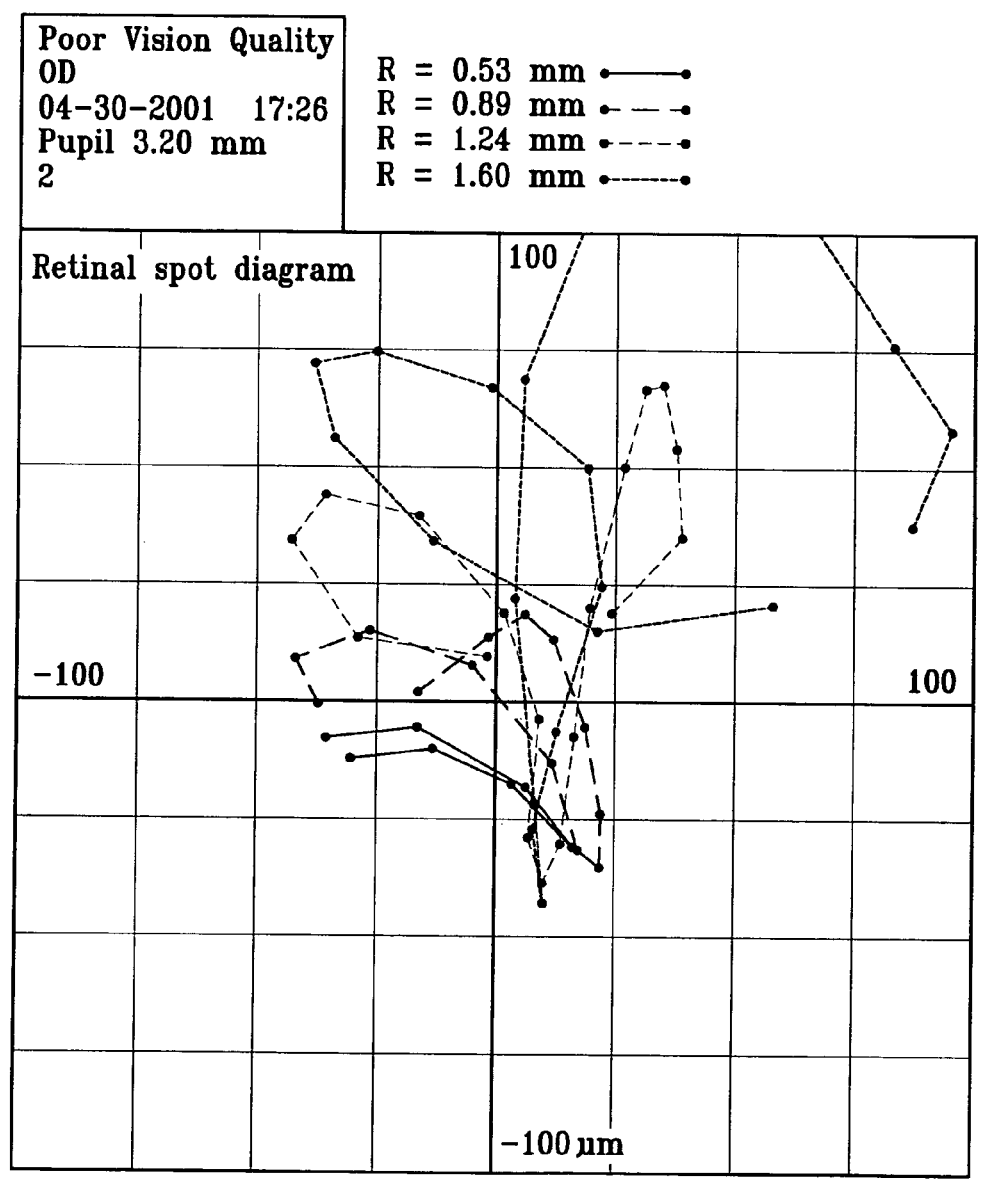
FIG. 48 is a retinal spot diagram of the poor eye at 4×0.5 diopter spherical steps positive correction from the −0.80 proposed sphero-cylindrical correction.

FIG. 48 is a retinal spot diagram of the poor eye at 4×0.5 diopter spherical steps positive correction from the −0.80 proposed sphero-cylindrical correction.

Figure 49:
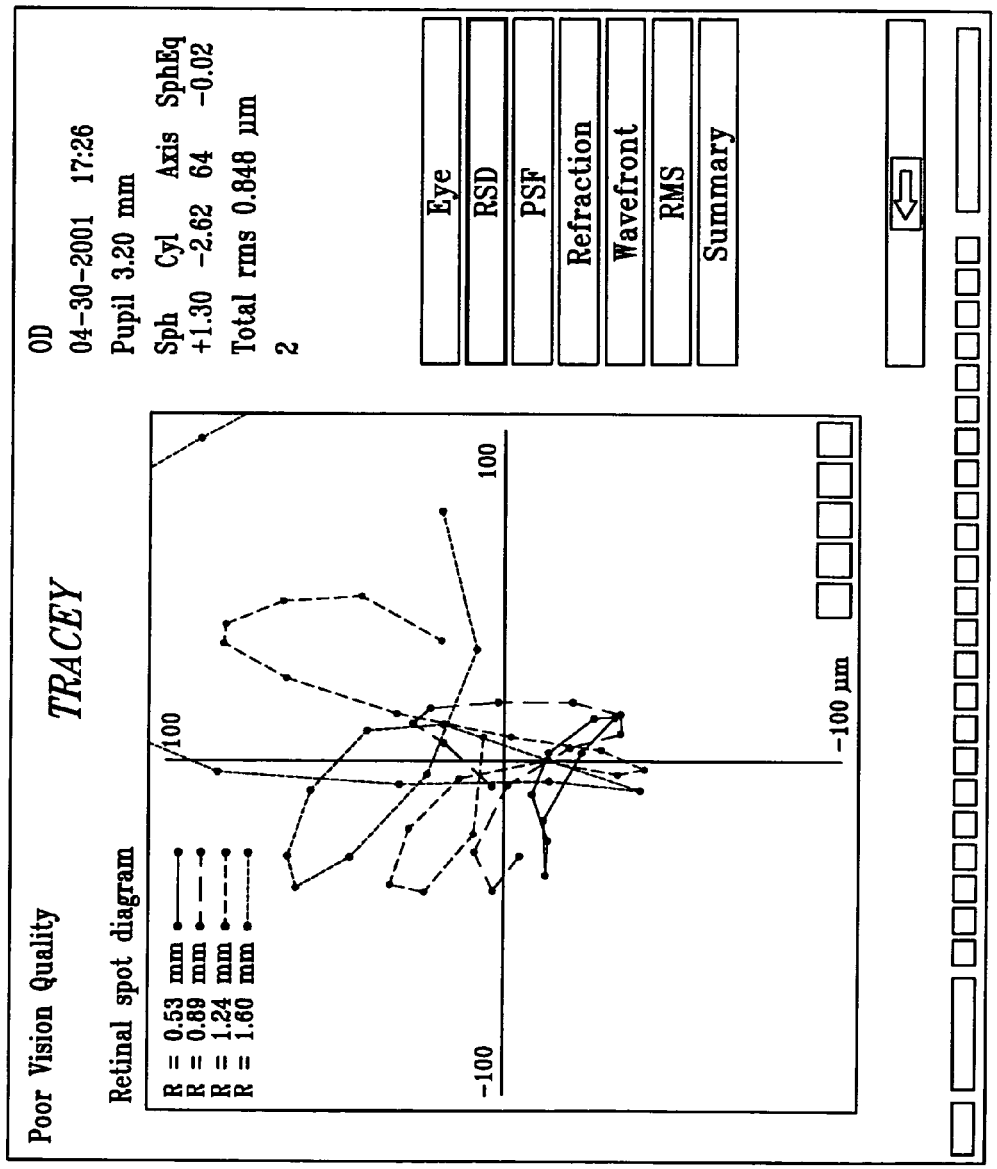
FIG. 49 is a retinal spot diagram of the poor eye at +1.30 proposed sphero-cylindrical correction showing color coded spots to permit correlation between input beams and the retinal spots.

FIG. 49 is a retinal spot diagram of the poor eye at +1.30 proposed sphero-cylindrical correction showing color coded spots to permit correlation between input beams and the retinal spots.

Figure 50:
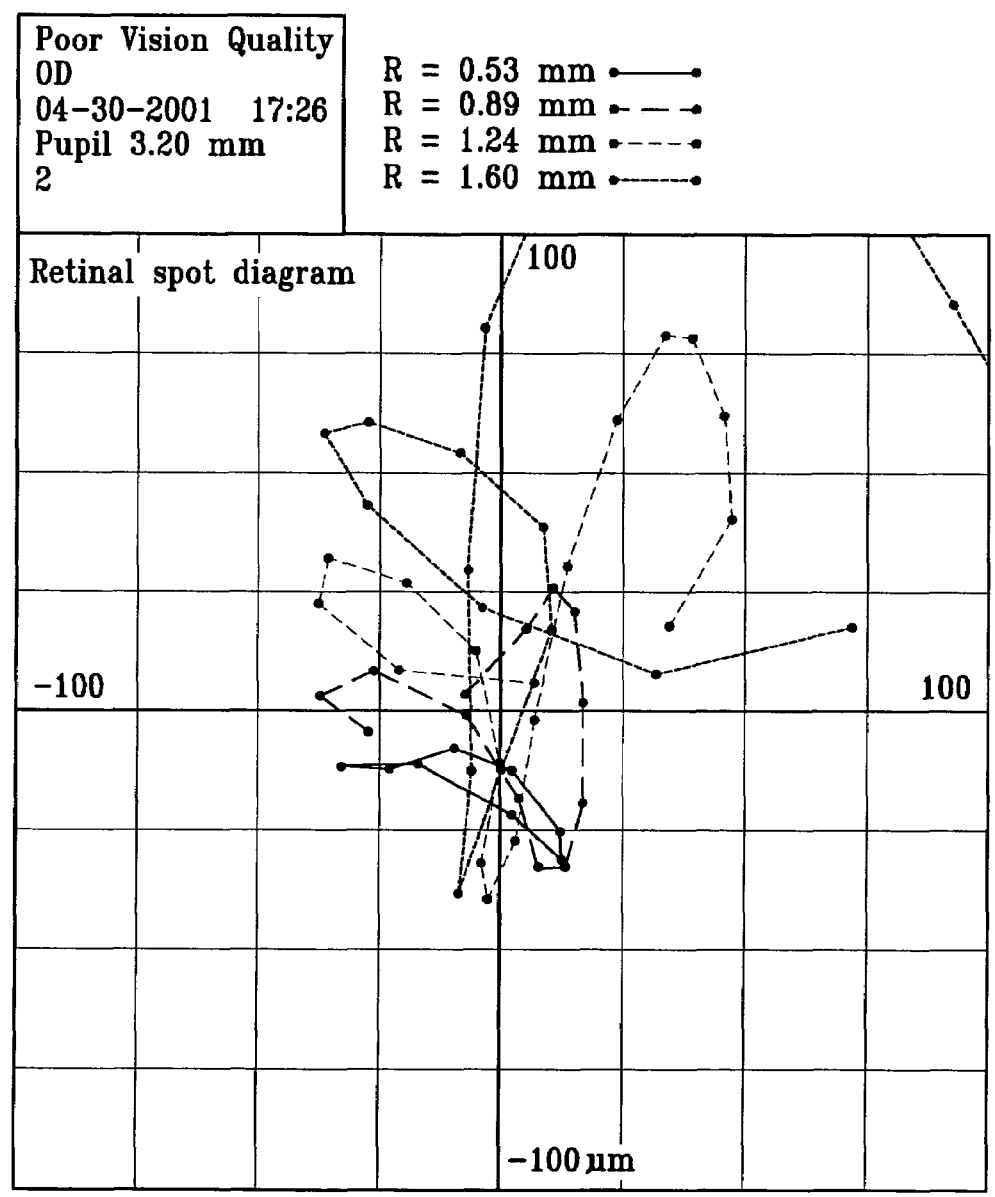
FIG. 50 is a retinal spot diagram of the poor eye at 5×0.5 diopter spherical steps positive correction from the −0.80 proposed sphero-cylindrical correction.

FIG. 50 is a retinal spot diagram of the poor eye at 5×0.5 diopter spherical steps positive correction from the −0.80 proposed sphero-cylindrical correction.

Figure 51:
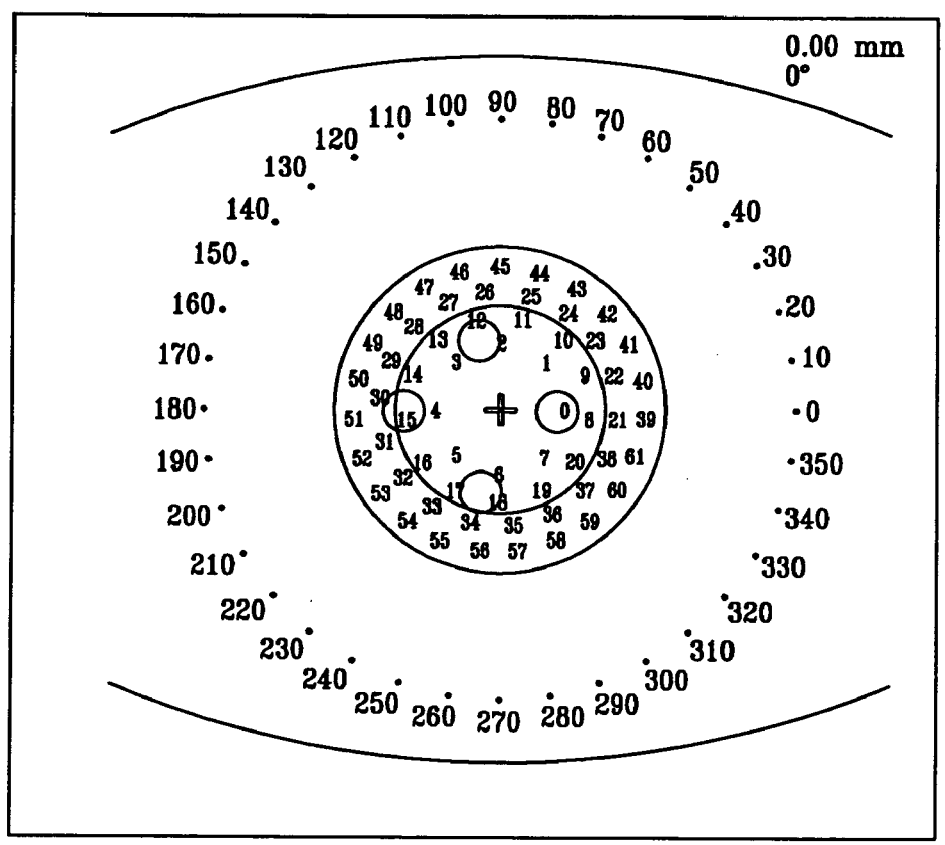
FIG. 51 is the pupil of an excellent eye with beam points of entry used to produce retinal spot diagrams with ray tracing technology.

FIG. 51 is the pupil of an excellent eye with beam points of entry used to produce retinal spot diagrams with ray tracing technology.

Figure 52:
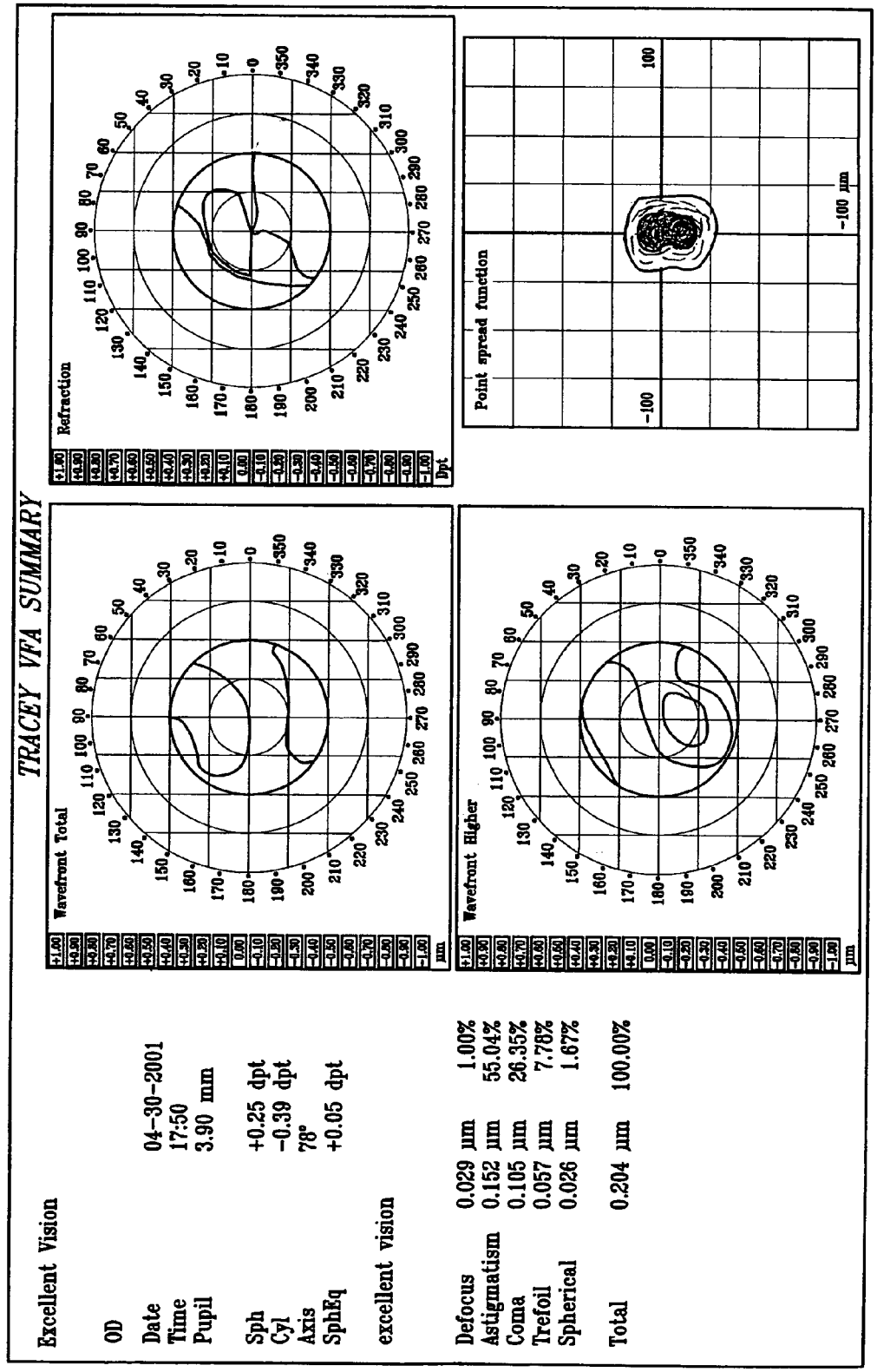
FIG. 52 shows diagrams of wavefront refraction, wavefront total, wavefront higher order distortions, and point spread function.

FIG. 52 shows diagrams of wavefront refraction, wavefront total, wavefront higher order distortions, and point spread function.

Figure 53:
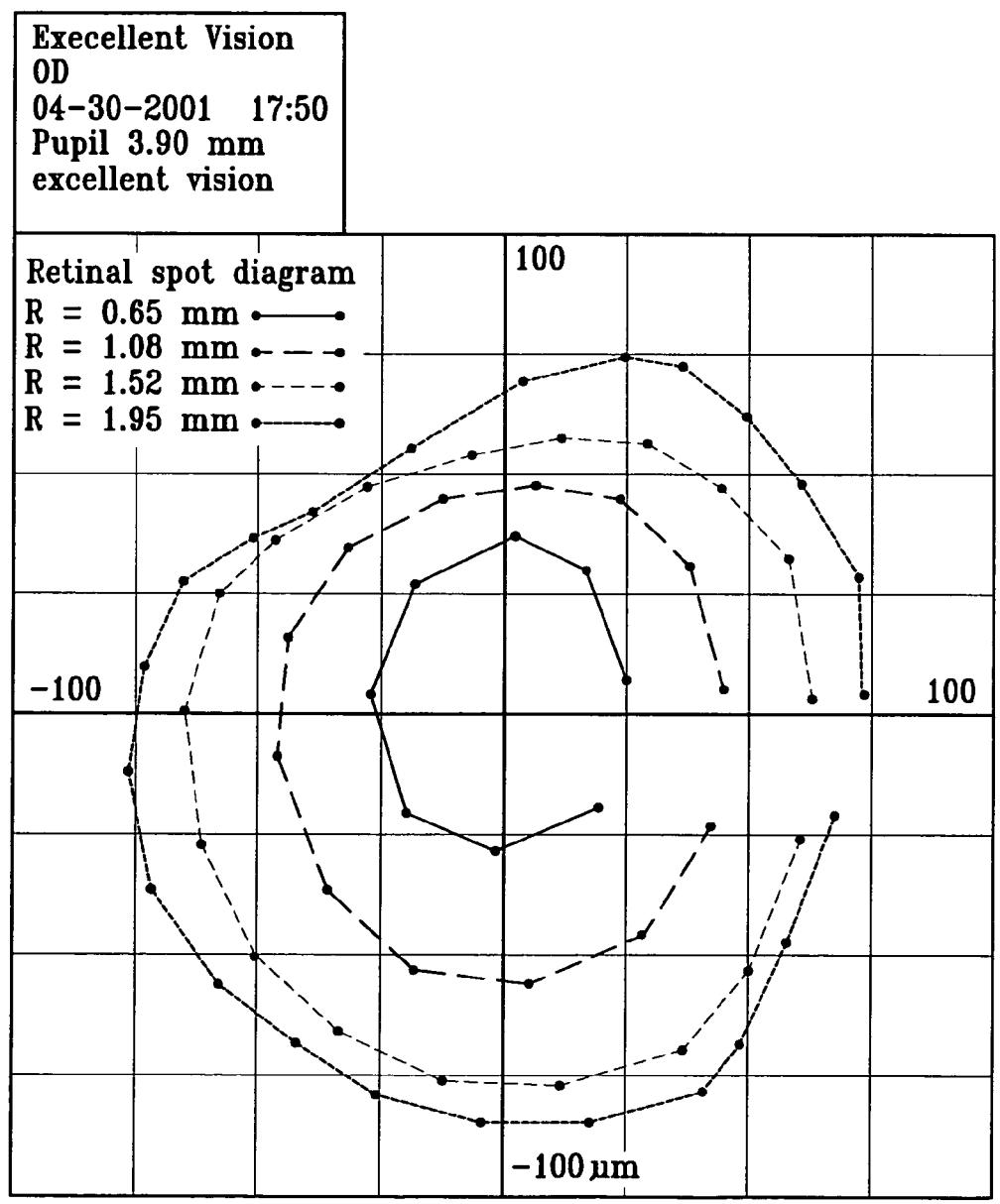
FIG. 53 is a retinal spot diagram of the excellent eye at 4×0.5 diopter spherical steps positive correction from the +0.25 proposed sphero-cylindrical correction.

FIG. 53 is a retinal spot diagram of the excellent eye at 4×0.5 diopter spherical steps positive correction from the +0.25 proposed sphero-cylindrical correction.

Figure 54:
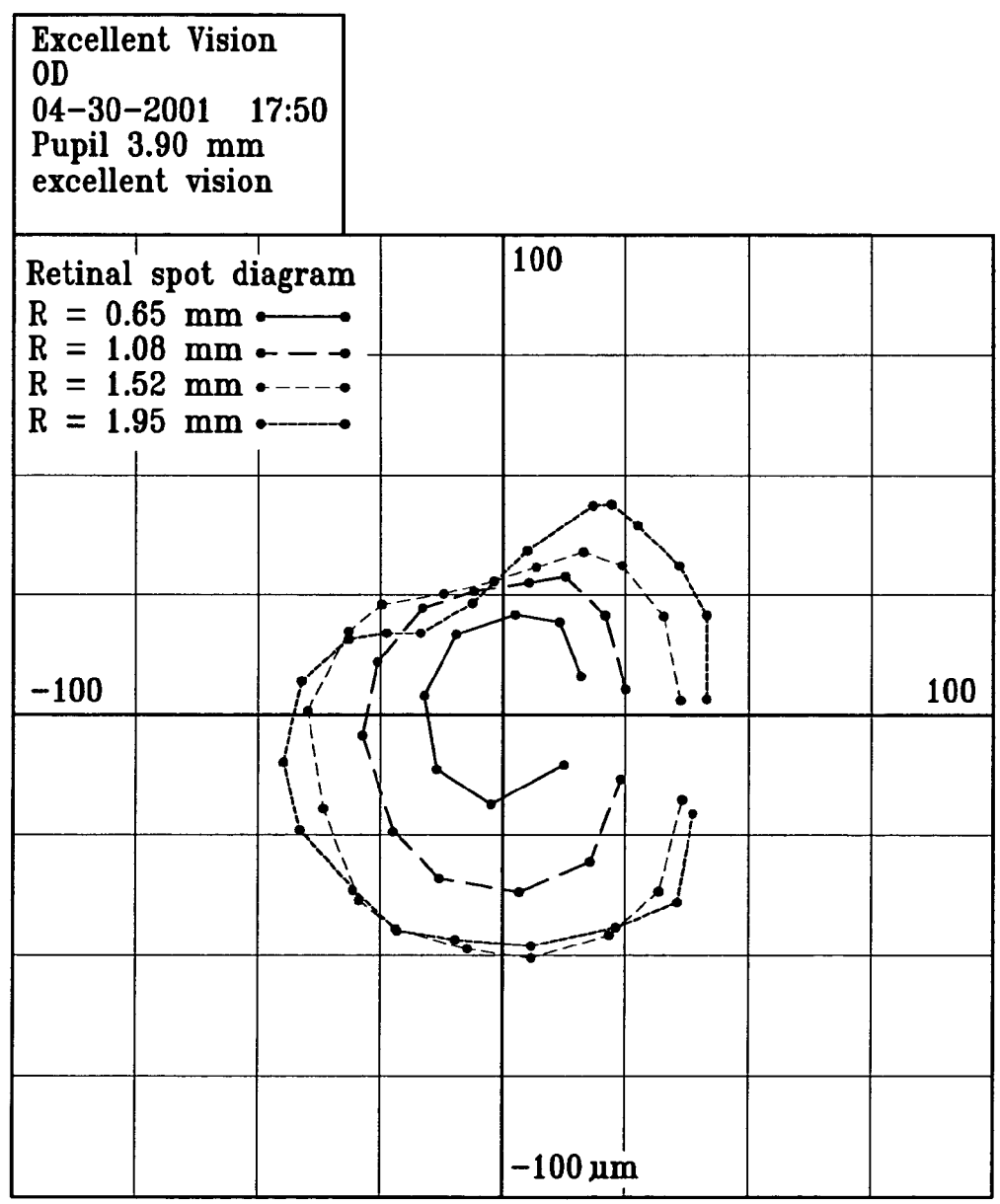
FIG. 54 is a retinal spot diagram of the excellent eye at 3×0.5 diopter spherical steps positive correction from the +0.25 proposed sphero-cylindrical correction.

FIG. 54 is a retinal spot diagram of the excellent eye at 3×0.5 diopter spherical steps positive correction from the +0.25 proposed sphero-cylindrical correction.

Figure 55:
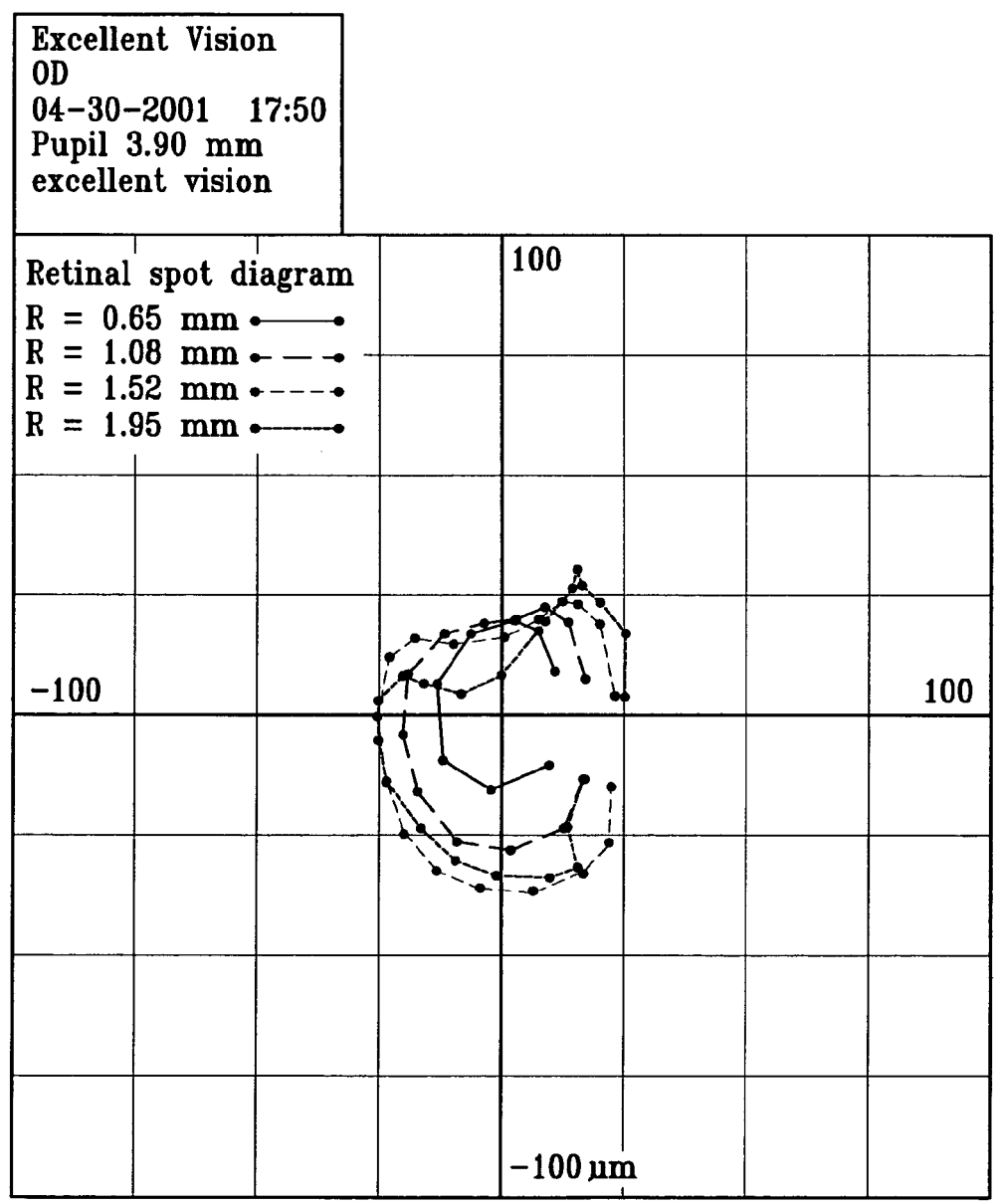
FIG. 55 is a retinal spot diagram of the excellent eye at 2×0.5 diopter spherical steps positive correction from the +0.25 proposed sphero-cylindrical correction.

FIG. 55 is a retinal spot diagram of the excellent eye at 2×0.5 diopter spherical steps positive correction from the +0.25 proposed sphero-cylindrical correction.

Figure 56:
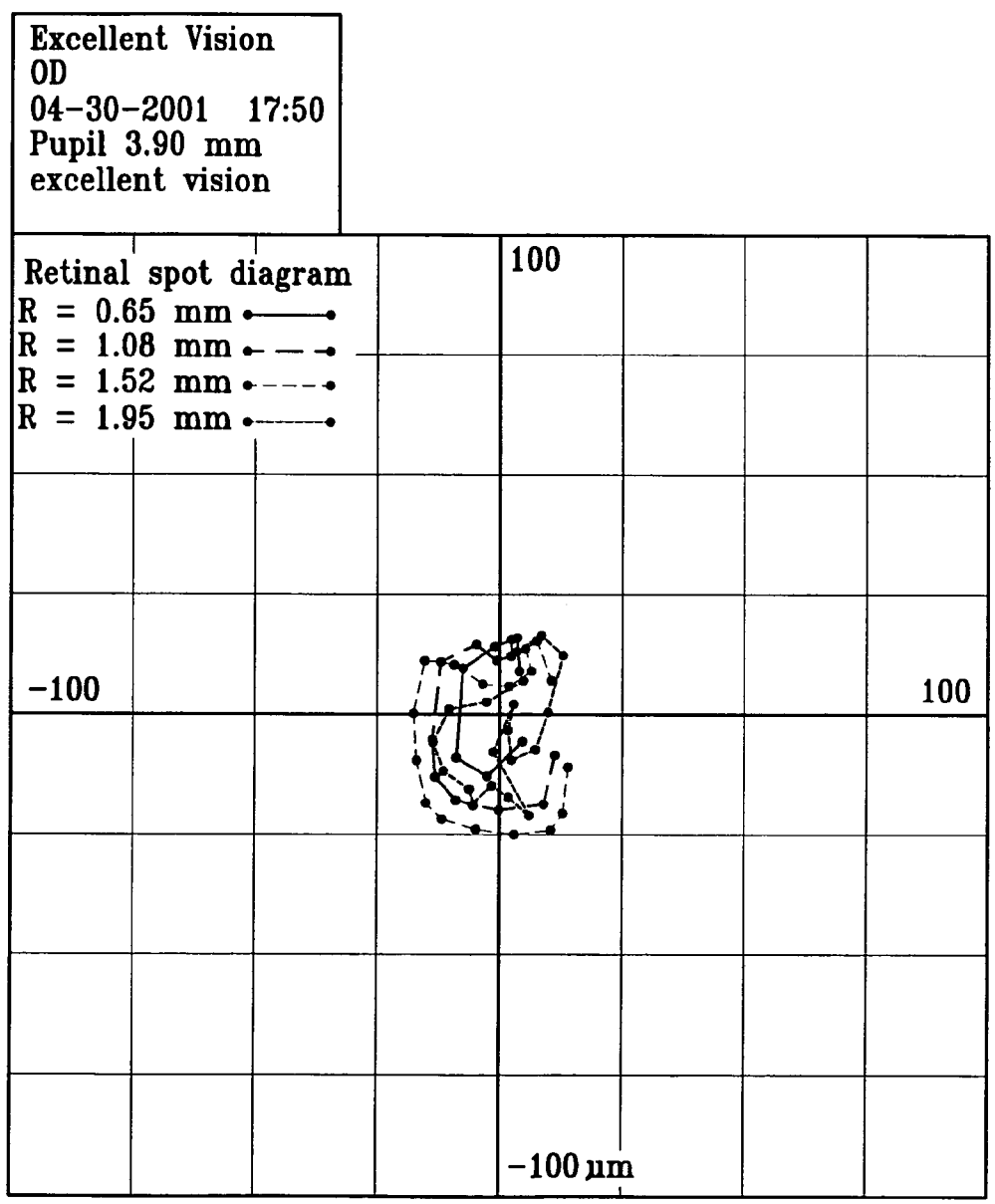
FIG. 56 is a retinal spot diagram of the excellent eye at 1×0.5 diopter spherical steps positive correction from the +0.25 proposed sphero-cylindrical correction.

FIG. 56 is a retinal spot diagram of the excellent eye at 1×0.5 diopter spherical steps positive correction from the +0.25 proposed sphero-cylindrical correction.

Figure 57:
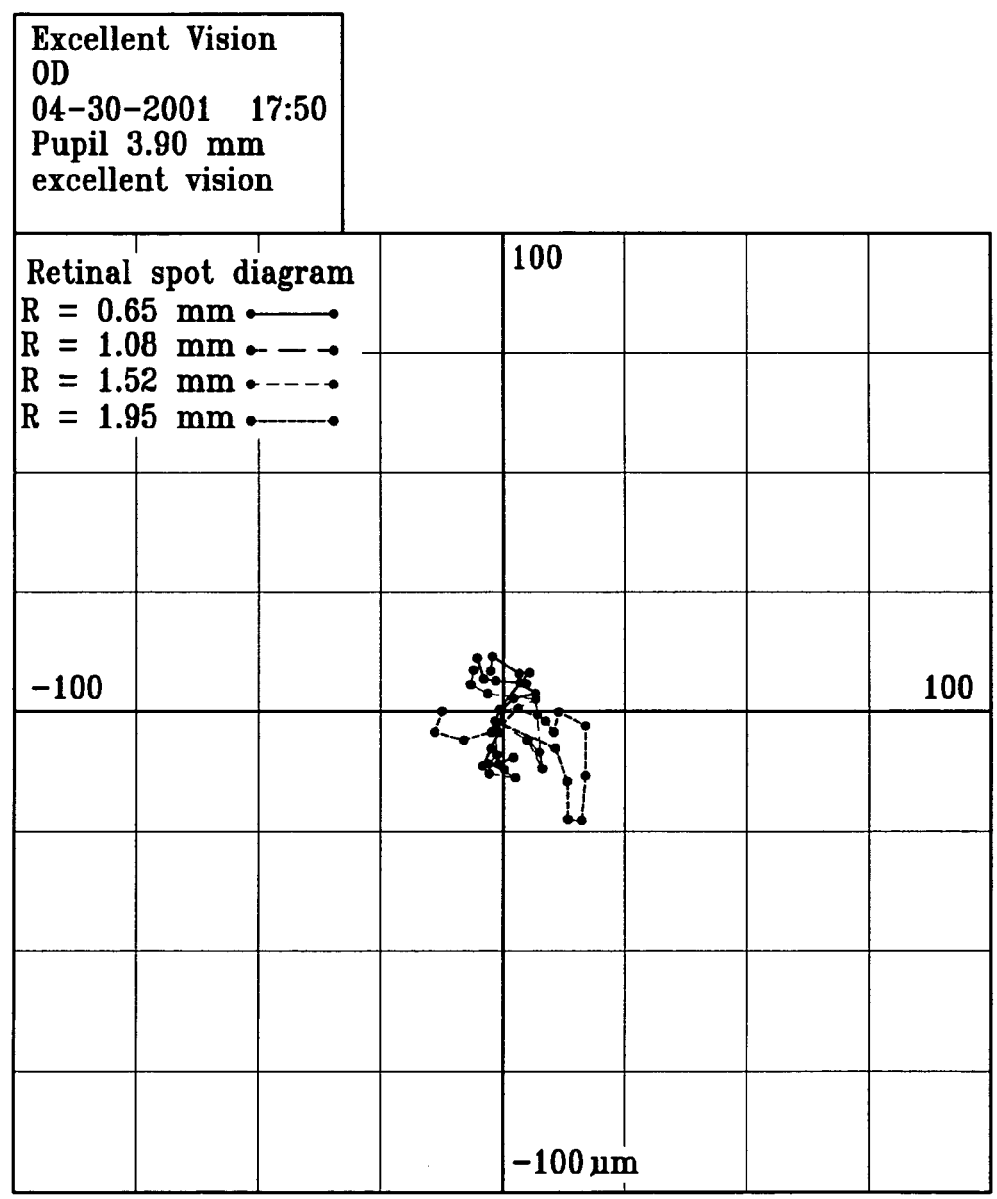
FIG. 57 is a retinal spot diagram of the excellent eye at the +0.25 proposed sphero-cylindrical correction.

FIG. 57 is a retinal spot diagram of the excellent eye at the +0.25 proposed sphero-cylindrical correction.

Figure 58:
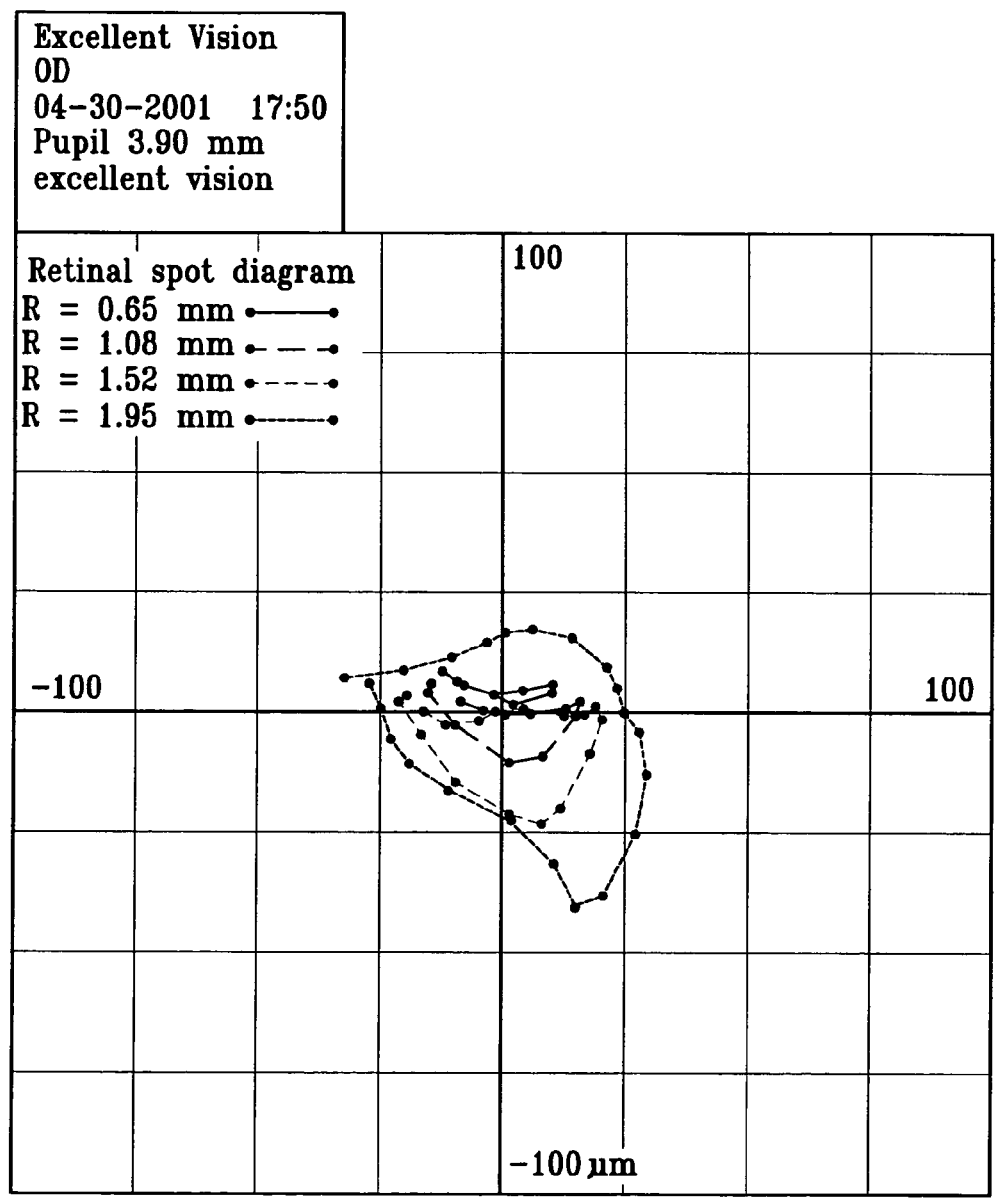
FIG. 58 is a retinal spot diagram of the excellent eye at 1×0.5 diopter spherical steps negative correction from the +0.25 proposed sphero-cylindrical correction.

FIG. 58 is a retinal spot diagram of the excellent eye at 1×0.5 diopter spherical steps negative correction from the +0.25 proposed sphero-cylindrical correction.

Figure 59:
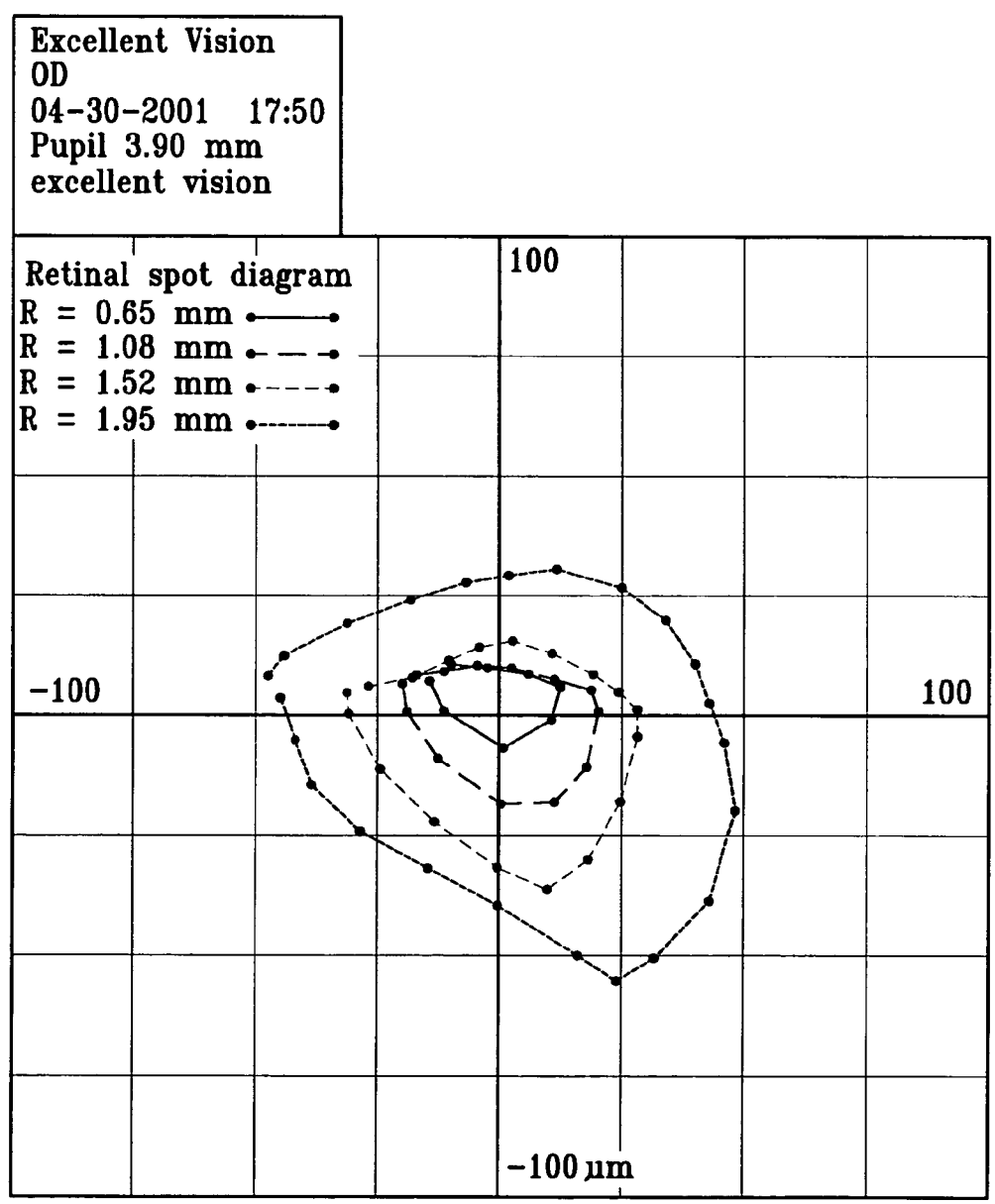
FIG. 59 is a retinal spot diagram of the excellent eye at 2×0.5 diopter spherical steps negative correction from the +0.25 proposed sphero-cylindrical correction.

FIG. 59 is a retinal spot diagram of the excellent eye at 2×0.5 diopter spherical steps negative correction from the +0.25 proposed sphero-cylindrical correction.

Figure 60:
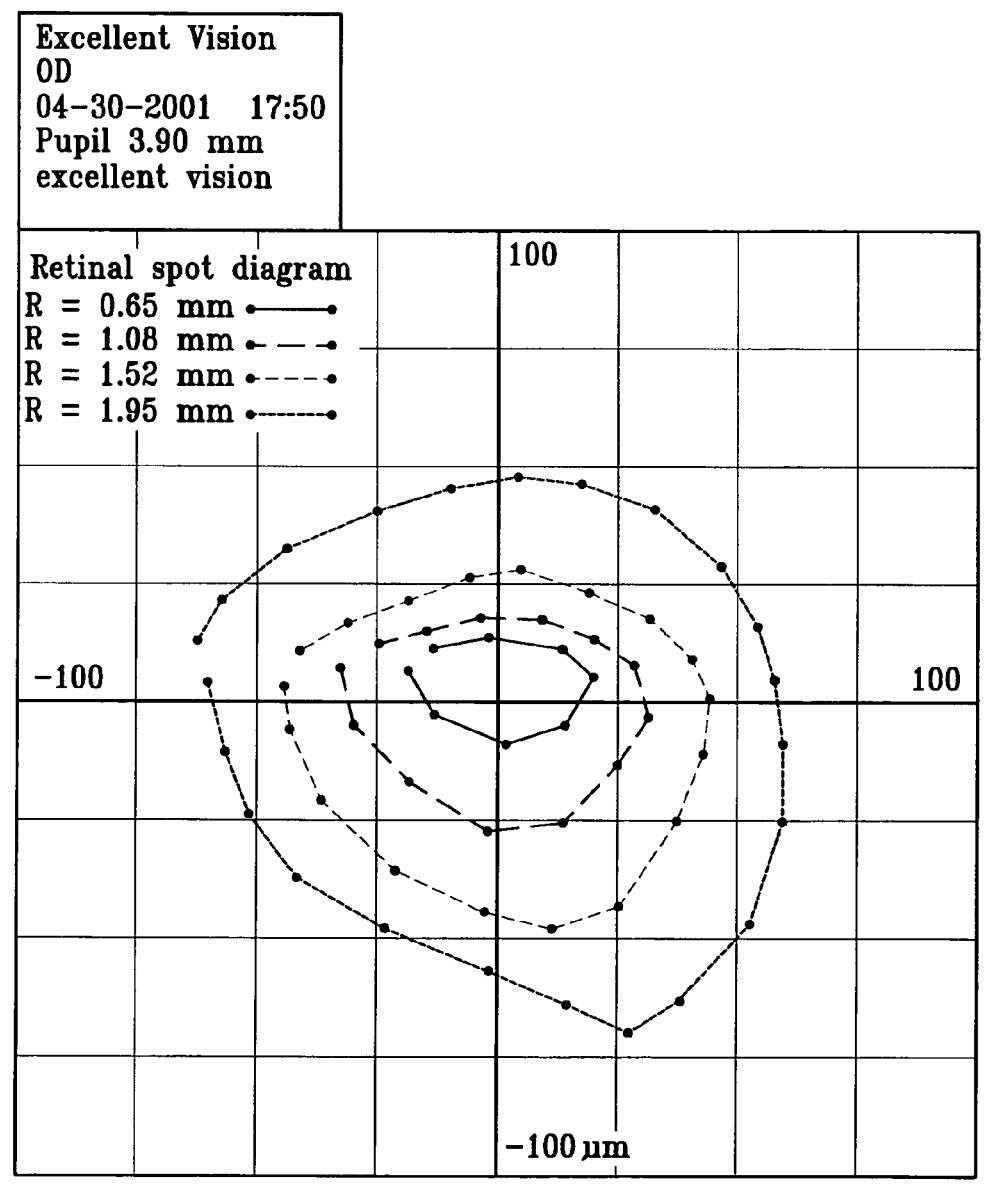
FIG. 60 is a retinal spot diagram of the excellent eye at 3×0.5 diopter spherical steps negative correction from the +0.25 proposed sphero-cylindrical correction.

FIG. 60 is a retinal spot diagram of the excellent eye at 3×0.5 diopter spherical steps negative correction from the +0.25 proposed sphero-cylindrical correction.

Figure 61:
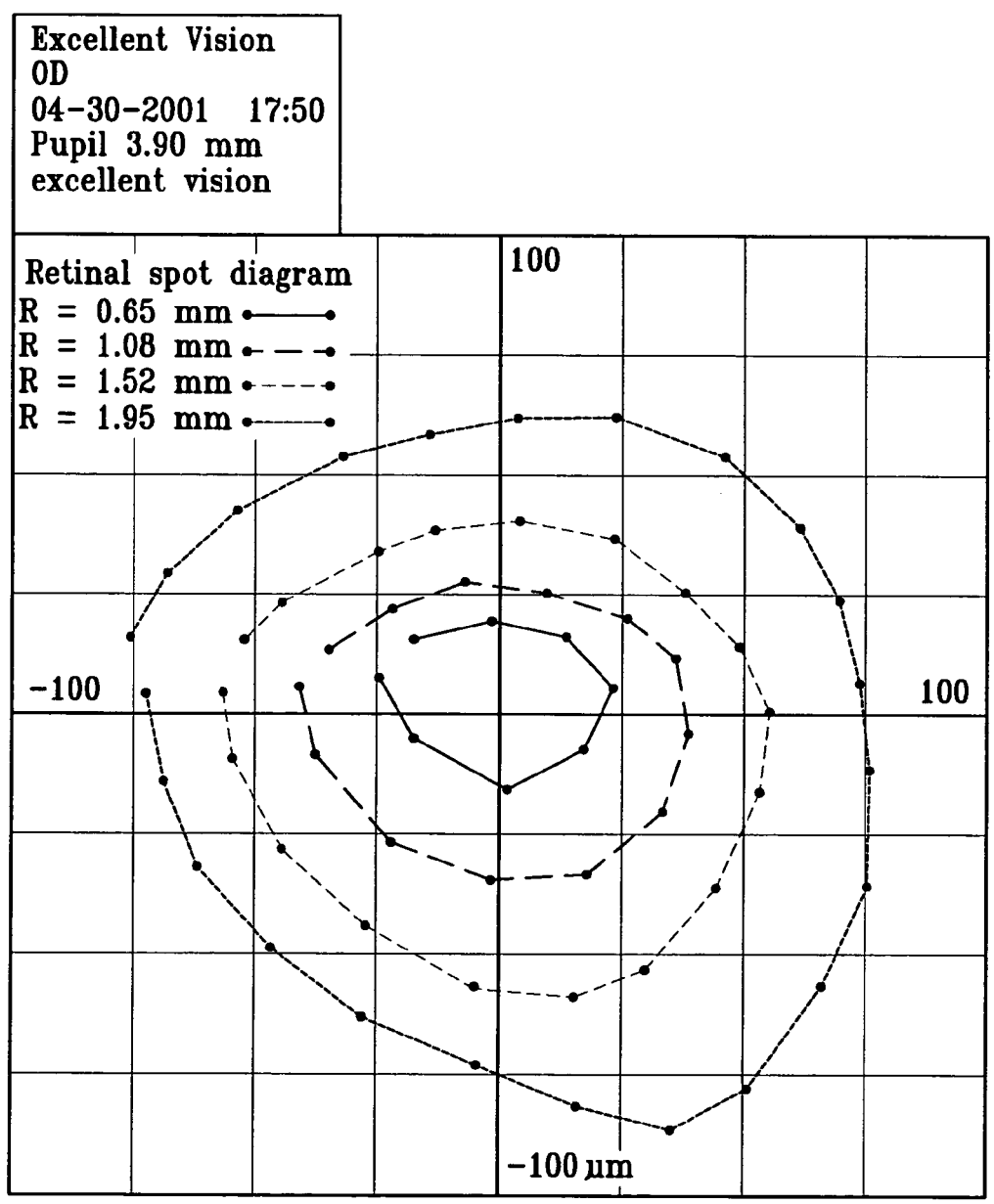
FIG. 61 is a retinal spot diagram of the excellent eye at 4×0.5 diopter spherical steps negative correction from the +0.25 proposed sphero-cylindrical correction.

FIG. 61 is a retinal spot diagram of the excellent eye at 4×0.5 diopter spherical steps negative correction from the +0.25 proposed sphero-cylindrical correction.

By comparing the different retinal spot diagrams it can be seen that in addition to acuity normally improved only using defocus and astigmatism corrections, other refraction characteristics can now be observed, measured and correlated to subjectively determined quality of vision as by using a phoropter. The aberrations can also be expressed in higher order Zernike polynomial term or other mathematical expressions such as spline mathematics or other interpolations methods. From these better expressions of the aberrations corrections can be directed to change the desired characteristics for improving the quality of vision. Test phase plates can also be used to test the corrections before providing more permanent correction such a laser vision correction to the eye.

Figure 62:
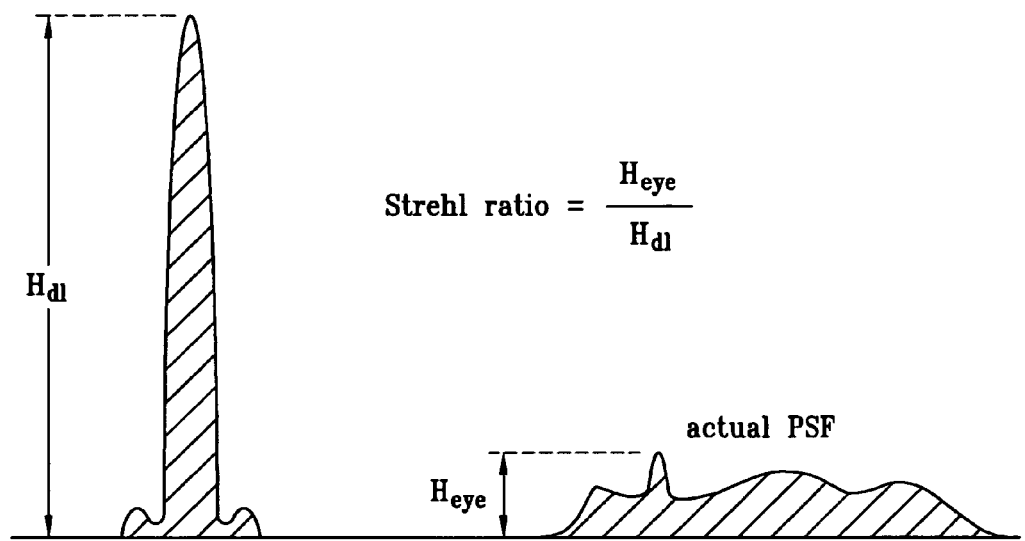
FIG. 62 shows a diagrammatic depiction of a Strehl Ration calculation.

FIG. 62 shows a diagrammatic depiction of a Strehl Ration calculation, the Theoretical maximum intensity of light transmitted trough a lens is indicated at the left as a peak diffraction limit Hdl and the peak light intensity of the spot diagram id represented at the right as Heye. The Strehl ratio might de considered for purposes herein as a ratio of the Hdl/Heye.

Figure 63:
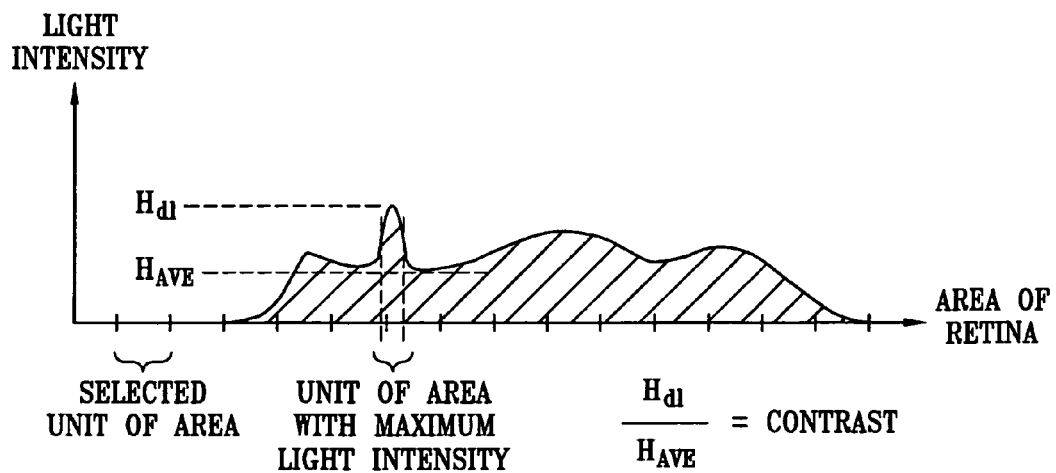
FIG. 63 shows another measure of contrast sensitivity.

FIG. 63 shows another measure of contrast sensitivity in terms of the maximum illumination receive in any predetermined small unit of area H(u) divided by the average illumination over the entire spot diagram H(ave). This gives an indication of how intense the illumination is in the small unit.

Thus what has been developed are several novel algorithms used in a method to determine the ideal manifest refraction of a patient's eye, as is clinically determined today. This determination according to the present invention is made strictly from objective data retrieved from a digital aberroscope device such as the device disclosed in the ray tracing system described in detail above or from another device as may be used to appropriately measure and quantify the wavefront deformations of the human eye. These algorithms assure an extremely high correlation with the preferred sphero-cylindrical correction of the patient as is subjectively determined with a phoropter or trial lens set in standard clinical practice today. These algorithms can lead to even greater quality of vision than only sphero-cylindrical corrections such as customized correction using improved lenses of customized correction generated by laser vision correction. Improve vision performance can be achieved which optimizes subjective refraction and thus quality of vision. The understanding of visual optics and using functions to determine the appropriate endpoints for a satisfactory if not optimized correction from wavefront measurements has provided the desired result. The invention develops algorithms in mostly generated by numerical analysis of RSD as it is modified by known perturbations of the eye length or diopter spherical correction to reveal changes in the RSD by different patterns of light focused on the retina for evaluation in the following fashion:

1) Numerical analysis to determine minimal beam cross-section for ideal acuity.
2) Numerical analysis to determine maximize Strehl ratio and/or to measure the ratio of the area of maximum spot density to the total spot area to maximize the contrast sensitivity.
3) Numerical analysis to determine the depth of focus based upon minimum CLOC.
4) Numerical analysis to determine dynamic refraction characteristics for near to far and far to near focus accommodation over time.
5) Numerical analysis to determine dynamic refraction characteristics for changing illumination over time
6) Numerical analysis to determine binocular refraction including any of the foregoing determined characteristics Other alterations and modifications of the invention will likewise become apparent to those of ordinary skill in the art upon reading the present disclosure, and it is intended that the scope of the invention disclosed herein be limited only by the broadest interpretation to which the inventors are legally entitled.

REFERENCES

1. M. S. Smirnov. Measurement of wave aberration of the eye. *Biofizika (Biophysics USSR)*, 6, pp. 776-794, 1961.
2. Van den Brink. Measurement of the geometrical aberrations of the eye. *Vision Res.* 2, pp. 233-244, 1962.
3. N. M. Sergienko. *Oftalmologicheskaya optika (Ophtalmic Optics)*. Moscow, Meditsina, 1991, 142 pages.
4. R. H. Webb, C. M. Penney, and K. D. Thompson. Measurement of ocular local wavefront distortion with a spatially resolved refractometer. *Applied Optics.* 31, pp. 3678-3686, 1992.
5. S. G. El Hage and Berni F. Contribution of the crystalline lens to the spherical aberration of the eye. J. Opt. Soc. Am. 63, pp. 205-211, 1973.
6. J. Liang. A new method to precisely measure the wave aberrations of the human eye with a Hartmann-Shack wavefront sensor, *Ph. D. Dissertation*, University of Heidelberg, Heidelberg, Germany, 1991.
7. J. Liang, B. Grimm, S. Goelz, and J. F. Bille, Objective measurement of wave aberrations of the human eye with the use of a Hartmann-Shack wave-front sensor. *J Opt. Soc. Am. A* 11, pp.1949-1957, 1994.
8. J. Liang and D. R. Williams. Aberrations and retinal image quality of the normal human eye. *J Opt. Soc. Am.* A 14, pp. 2873-2883, 1997.
9. J. Liang, D. R. Williams, and D. T. Miller. Supernormal vision and high resolution retinal imaging through adaptive optics, *J. Opt. Soc. Am.*, A 14, pp. 2884-2892, 1997.
10. U.S. Pat. No. 5,258,791. Spatially resolved objective autorefractometer, Nov. 2, 1993.
11. T. Seiler, P. J. McDonnell, "Excimer laser photorefractive keratectomy", *Surv. of Ophthalm.*, 40, pp. 89-118, 1995.

What is claimed is:

1. A method of testing vision for diagnosing the refractive state of the eye comprising the steps of:
   a) conducting objective refraction testing of the eyes of a sample of patients to obtain results indicating objective refraction characteristics of each patient's eyes;
   b) conducting subjective eye tests for the same sample of patients, with eye examinations to obtain refractive correction data with and without spherical and/or cylindrical correction in an attempt to achieve each patient's subjectively desired quality of vision;
   c) comparing the objective test results for each sample patient with the subjective test results for each same sample patient to determine a correlation between objectively determined refractive characteristics of the eyes and the subjectively determined desired quality of vision; and
   d) conducting objective refraction test on a new patient and predicting corrective actions for producing subjectively desired qualities of vision based upon the correlation made using the objective and subjective test results for the sample of patients.

2. The method of claim 1 further comprising the step of providing the refractive correction predicted for the new patient.

3. The method of claim 1 wherein the refractive characteristics provided by the objective tests results include refraction expressed in terms of wavefront distortions.

4. The method of claim 1 wherein the refractive characteristics provided by the objective tests results include refraction expressed in terms of a mathematical function.

5. The method of claim 4 wherein the mathematical function comprises a polynomial expansion series.

6. The method of claim 4 wherein the mathematical function comprises Zernicke polynomial expansion terms.

7. The method of claim 4 wherein the mathematical function comprises spline mathematical calculations.

8. The method of claim 1 wherein the refractive characteristics provided by the objective tests results comprise characteristics determined from analysis of a retinal spot diagram (RSD) generated from ray tracing data or other wavefront data.

9. The method of claim 1 wherein the step of conducting objective eye testing comprise the steps of:
   a) using ray tracing to determine the refractive characteristics of each eye at a plurality of spatially resolved locations on the eye; and
   b) calculating from the plurality of refractive characteristics at the plurality of points an estimated expression of the refraction characteristics based upon best fit by a curve fitting algorithim.

10. A method as in claim 9 wherein the curve fitting algorithm comprises a Zernicke polynomial expansion including terms of a higher than the second order that also provide sphere and cylinder components.

11. The method of claim 1 wherein the step of conducting objective eye testing comprise the steps of:
   a) using Hartmann-Shack wavefront sensing to determine the refractive characteristics of each eye; and
   b) calculating from the Hartmann-Shack wavefront analysis an expression of refraction based upon best fit to a curve fitting mathematical function.

12. The method of claim 1 wherein the step of conducting objective eye testing comprise the steps of:
   a) using an aberroscope to determine distortion in a grid projected on the eye to indicate the refractive characteristics of each eye; and
   b) calculating from the aberroscope grid distortions an estimated expression of refraction based upon best fit to a mathematical function.

13. The method of claim 1 wherein the step of objectively measuring refraction comprises a dynamic measurement during eye change of focus at changing target distances.

14. The method of claim 1 wherein the step of objectively measuring refraction comprises a dynamic measurement during pupil dilation and constriction according to of changing light illumination.

15. A method of changing eye refraction to achieve desired vision characteristics comprising the steps of:
   a) objectively measuring the eye refraction that defines the vision characteristic for which change is desired;
   b) preparing a test phase plate to correct refraction of the eye using only second order Zernicke polynomial terms to direct the correction to produce a change in the refraction that will result in the desired change in the vision characteristic;
   c) testing the vision of the eye with the phase plate applied to determine whether the desired quality of vision is achieved with phase plate;
   d) based on test results with the phase plate applied showing desired quality of vision, then programming a laser eye surgery device to reshape the cornea to produce a change in the refraction that will result in the desired change in the vision characteristic;
   e) based on test results with the phase plate applied not showjng desired quality of vision then preparing a next test phase plate to correct refraction of the eye using Zernicke polynomial terms higher than the second order to direct the correction to produce a change in the refraction that will result in the desired change in the vision characteristic;
   f) testing the vision of the eye with the next test phase plate applied to determine whether the desired quality of vision is achieved with next phase plate; and
   g) based on test results with the next phase plate applied showing desired quality of vision, then programming a laser eye surgery device to reshape the cornea using the higher order Zernicke polynomial terms to direct correction to produce a change in the refraction that will result in the desired change in the vision characteristic.

16. The method of claim 15 wherein the desired vision characteristic to be changed is visual acuity.

17. The method of claim 16 wherein the desired visual acuity characteristic is determined using an objectively measured circle of least confusion.

18. The method of claim 15 wherein the desired vision characteristic to be changed is depth of focus.

19. The method of claim 15 wherein the desired vision characteristic to be changed is contrast sensitivity.

20. The method of claim 19 wherein the desired contrast sensitivity characteristic is determined based upon a determination of a maximum Strehl ratio.

21. The method of claim 19 wherein the desired contrast sensitivity characteristic is determined based upon a determination of an index calculate using a ratio of the area of a retinal spot diagram having a predetermined intensity of light illumination to the total area of the retinal spot diagram.

22. The method of claim 15 wherein the desired vision characteristic to be changed is the circle of least confusion determined using ray tracing.

23. The method of claim 15 wherein the desired vision characteristic to be changed is the circle of least confusion determined using wave front aberration technology.

24. A method of measuring eye refraction to achieve desired quality according to a selected vision characteristics comprising the steps of:
   a) selecting a characteristic of vision to correlate to the desired quality of vision from a group of vision characteristics comprising acuity, Strehl ratio, contrast sensitivity, night vision, day vision, and depth of focus, dynamic refraction over a period of time during focus accommodation, and dynamic refraction over a period of time during pupil constriction and dilation;
   b) using wavefront aberration measurements to objectively measure the state of the eye refraction that defines the desired vision characteristic; and
   c) expressing the measured state of refraction with a mathematical function to enable correction of the pre-selected vision characteristic to achieve the desired quality of vision.

25. The method of claim 24 wherein the mathematical function of expression comprises a Zernicke polynomial having both second order and higher order terms or a function determined by spline mathematical calculations.

26. The method of claim 24 wherein the pre-selected desired vision characteristic comprises a circle of least confusion determined using ray tracing.

27. The method of claim 24 wherein the pre-selected desired vision characteristic comprises visual acuity.

28. The method of claim 24 wherein the desired visual acuity characteristic is determined using an objectively measured circle of least confusion.

29. The method of claim 24 wherein the pre-selected desired vision characteristic comprises depth of focus.

30. The method of claim 24 wherein the pre-selected desired vision characteristic comprises contrast sensitivity.

31. The method of claim 30 wherein the desired contrast sensitivity characteristic is determined based upon a determination of a maximum Strehl ratio.

32. The method of claim 24 wherein the pre-selected desired vision characteristic comprises a circle of least confusion determined using ray tracing.

* * * * *